United States Patent
Suzuki et al.

(10) Patent No.: US 6,794,392 B1
(45) Date of Patent: Sep. 21, 2004

(54) CELL DIFFERENTIATION INDUCER

(75) Inventors: Tsuneji Suzuki, Chiba (JP); Tomoyuki Ando, Chiba (JP); Katsutoshi Tsuchiya, Chiba (JP); Osamu Nakanishi, Pasadena, CA (US); Akiko Saito, Chiba (JP); Takashi Yamashita, Chiba (JP); Yoshinori Shiraishi, Kanagawa (JP); Eishi Tanaka, Chiba (JP)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/417,216

(22) Filed: Oct. 13, 1999

Related U.S. Application Data

(62) Division of application No. 08/935,087, filed on Sep. 26, 1997, now Pat. No. 6,174,905.

(30) Foreign Application Priority Data

Sep. 30, 1996 (JP) .............................................. 8/258863

(51) Int. Cl.[7] ...................... A61K 31/505; A61K 31/44; A61K 31/47; C07D 498/00; C07D 277/56
(52) U.S. Cl. ...................... 514/269; 514/340; 514/357; 514/341; 514/374; 514/337; 548/221; 548/195; 546/284.1; 546/280.4
(58) Field of Search ................................. 564/305, 323; 568/306; 514/269, 374, 370, 340, 336, 331, 337, 357; 548/221, 195; 546/272.7, 276.4, 284.1, 280.4, 271.4, 218.4

(56) References Cited

U.S. PATENT DOCUMENTS 5,541,178 A * 7/1996 Betts et al. ................. 514/210

FOREIGN PATENT DOCUMENTS

EP        0490667        6/1992

(List continued on next page.)

OTHER PUBLICATIONS

CA 70: 106484w, Seven –membered heterocyclics. XII. Bibenz-[b,f]-1, 4–oxazepin-11 (10H)–ones and dibenz [b, e]-1, 4–oxazipin-11(5H)–ones, Kuenzle et. al., p. 343, 1969.*

(List continued on next page.)

Primary Examiner—Alan L. Rotman
Assistant Examiner—Binta Robinson
(74) Attorney, Agent, or Firm—Burns, Doane, Swecker & Mathis, LLP

(57) ABSTRACT

The novel benzamide derivative represented by formula (1) and the novel anilide derivative represented by formula (13) of this invention has differentiation-inducing effect, and are, therefore, useful a therapeutic or improving agent for malignant tumors, autoimmune diseases, dermatologic diseases and parasitism. In particular, they are highly effective as an anticancer drug, specifically to a hematologic malignancy and a solid carcinoma.

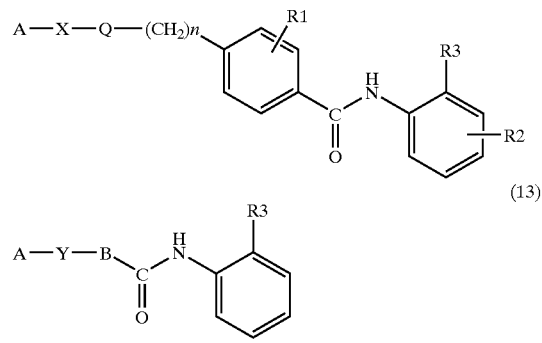

6 Claims, 1 Drawing Sheet

FOREIGN PATENT DOCUMENTS

| | | |
|---|---|---|
| JP | 6-179622 | 6/1994 |
| JP | 6-192073 | 7/1994 |
| JP | 6-256181 | 9/1994 |
| JP | 6-305955 | 11/1994 |
| JP | 6-316520 | 11/1994 |
| JP | 7-206765 | 8/1995 |
| JP | 7-258100 | 10/1995 |
| WO | WO96/21648 | 7/1996 |
| WO | WO97/24328 | 10/1997 |

OTHER PUBLICATIONS

Marston et. al., "On the active principles of teh Euphorbiaceae. VI. Isolation and biological activities of seven milliamines from Euphorbia milii", CA Refrence 100:64966k, p. 327, vol. 100. 1984.

H. Meng–er et al, "Use of All–Trans Retinoic Acid in the Treatment of acute prymyelocytic Leukemia", Blood, vol. 72, No. 2, Aug. 1988, pp. 567–572.

S. Castaigne et al, "All–Trans Retinoic Acid as a Differentiation Therapy for Acute Promyelocytic Leukemia. I. Clinical Results", Blood, vol. 76, No. 9, Nov. 1990, pp. 1704–1709.

R. Warrell, Jr., "Differentiation Therapy of Acute Promyelocytic Leukemia With Tretinoin (All–Trans–Retinoic Acid", The New England Journal of Medicine, vol. 324, No. 20, May 1991, pp. 1385–1393.

I. Olsson et al, "Introduction of Differentiation of the Human Histiocytic Lymphoma Cell Line U–937 b 1α, 25–Dihydroxycholecalciferol", Cancer Research, vol. 43, Dec. 1983, pp. 5862–5867.

M. Clark et al, "Validation of the General Purpose Tripos 5.2 Force Field", Journal of Computational Chemistry, vol. 10, No. 8, 1989, pp. 982–1012.

Chemical Abstracts, vol. 63, No. 13, Dec. 20, 1995, Columbus, OH, US; Abstract No. 18311g, B.S. Portnaya et al; XP002051609 & Zhurnal Nauchnoi I Prikladnoi Fotografii I Kinematografii, vol. 10, No. 4, 1965 Moscow ISSN 0044–4561, pp. 278–287.

Chemical Abstracts, vol. 119, No. 25, Dec. 20, 1993, Columbus, OH, US; Abstract No.270986n, J. Nowakowski: XP002051610 & PL 157 443 B (Uniwersytet Mikolaja Kopernika).

Y.V. Mitin et al, "Rearrangement of ortho–O–aminoacyl, N–acylaminophenol", Tetrahedron Letters, No. 12, 1979, Oxford GB, pp. 1081–1084, XP002051608.

\* cited by examiner

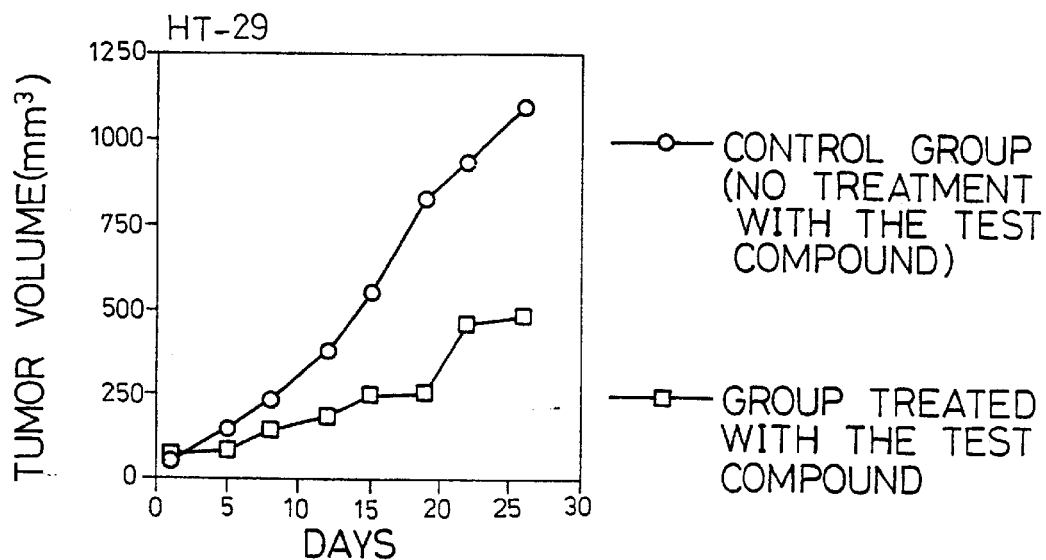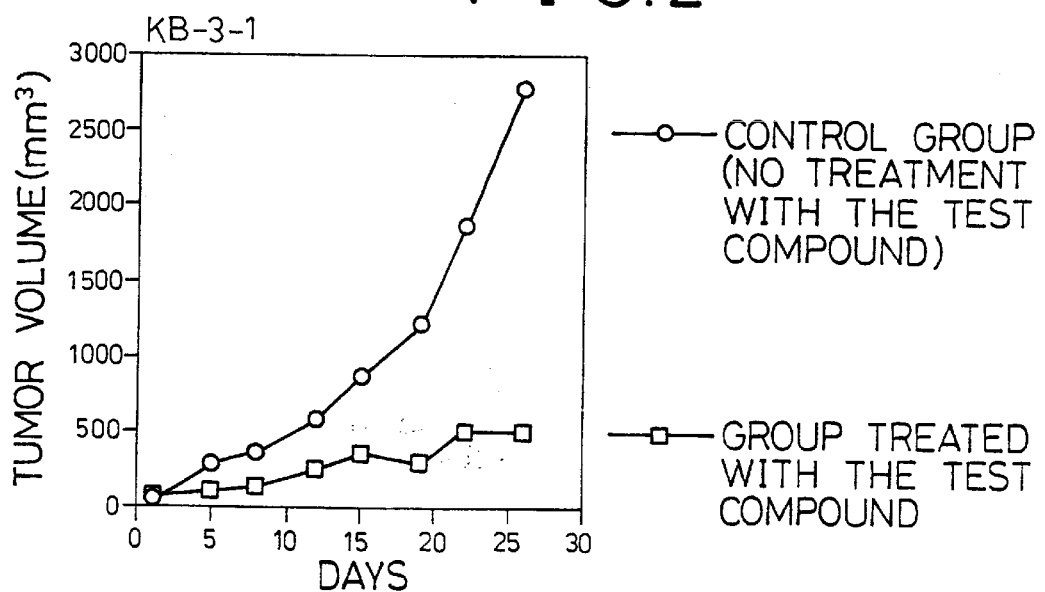

CELL DIFFERENTIATION INDUCER

This application is a divisional, of application Ser. No. 08/935,087, filed Sep. 26, 1997 now U.S. Pat. No. 6,174,905.

FIELD OF THE INVENTION

This invention relates to a differentiation-inducing agent. In particular, this invention relates to the use of a novel benzamide derivative or anilide derivative for an anticancer drug or other drugs based on its differentiation-inducing activity.

DESCRIPTION OF THE RELATED ART

Cancers have now become a top cause of death, exceeding heart and cerebrovascular diseases, and so many studies have been conducted with enormous expense and time to overcome cancers. They have not been, however, overcome in spite of a variety of investigations for therapy such as a surgical operation, a radiation therapy and thermotherapy. Among those therapies, chemotherapy is one of the main area for cancer treatment. To date, however, no satisfactory drugs have been discovered, and thus an anticancer drug with reduced toxicity and high therapeutic effect has been desired. Many of the conventional anticancer drugs show their effect by affecting mainly DNA to express their cytotoxicity and then injuring carcinoma cells. However, since they do not have sufficient selectivity between carcinoma cells and normal cells, adverse reactions expressed in normal cells have limited their use in therapy.

Meanwhile, differentiation-inducing agents among anticancer drugs are intended to induce differentiation of carcinoma cells for controlling their infinite proliferation, rather than directly kill the cells.

The agents may, therefore, be inferior to the anticancer drugs directly killing carcinoma cells, with regard to involution of a carcinoma, but may be expected to have reduced toxicity and different selectivity. In fact, it is well known that retinoic acid, a differentiation-inducing agent, may be used for treatment of acute promyelogenous leukemia to exhibit a higher effect [Huang et al., Blood, 72, 567–572(1988); Castaign et al., Blood, 76, 1704–1709 (1990); Warrell et al., New Engl. J. Med. 324, 1385–1393(1991) etc.]. In addition, vitamin D derivatives exhibit differentiation-inducing effect, and thus their application for anticancer drugs have been investigated [e.g., Olsson et al, Cancer Res. 43, 5862–5867 (1983) etc.].

As the results of these investigations, there have been reported applications for anticancer drugs, of a variety of differentiation-inducing agents such as vitamin D derivatives (JP-A 6-179622), isoprene derivatives (JP-A 6-192073), tocopherol (JP-A 6-256181), quinone derivatives (JP-A 6-305955), noncyclic polyisoprenoids (JP-A 6-316520), benzoic acid derivatives (JP-A 7-206765) and glycolipids (JP-A 7-258100). There have been no agents having sufficient level of effect for cancer treatment in spite of the investigations, and thus there has been greatly desired a highly safe agent effective to a variety of cancers.

SUMMARY OF THE INVENTION

An objective of this invention is to provide a compound which exhibits differentiation-inducing effect and is useful as a pharmaceutical agent such as therapeutic or improving agents for malignant tumors, autoimmune diseases, dermatologic diseases and parasitism.

We have intensely attempted to achieve the above objective and have found that a novel benzamide derivative and a novel anilide derivative having differentiation-inducing effect show antitumor effect, leading to this invention. Specifically, this invention provides a compound represented by formula (1) or a pharmaceutically acceptable salt thereof,

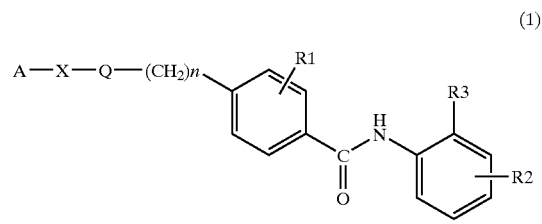

(1)

wherein A is an optionally substituted a phenyl or heterocyclic group which has 1 to 4 substituents selected from the group consisting of a halogen atom, a hydroxyl group, an amino group, a nitro group, a cyano group, an alkyl group having 1 to 4 carbons, an alkoxy group having 1 to 4 carbons, an aminoalkyl group having 1 to 4 carbons, an alkylamino group having 1 to 4 carbons, an acyl group having 1 to 4 carbons, an acylamino group having 1 to 4 carbons, an alkylthio group having 1 to 4 carbons, a perfluoroalkyl group having 1 to 4 carbons, a perfluoroalkyloxy group having 1 to 4 carbons, a carboxyl group, an alkoxycarbonyl group having 1 to 4 carbons, a phenyl group and a heterocyclic group;

X is a bond or a moiety having a structure selected from those illustrated in formula (2)

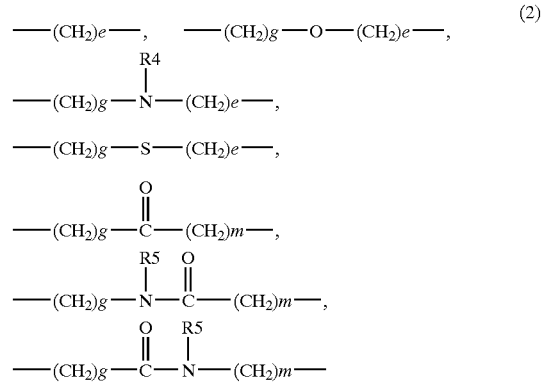

(2)

wherein e is an integer of 1 to 4; g and m are independently an integer of 0 to 4; $R^4$ is hydrogen or an optionally substituted alkyl group having 1 to 4 carbons, or the acyl group represented by formula (3)

(3)

wherein $R^6$ is an optionally substituted alkyl group having 1 to 4 carbons, a perfluoroalkyl group having 1 to 4 carbons, a phenyl group or a heterocyclic group; $R^5$ is hydrogen or an optionally substituted alkyl group having 1 to 4 carbons;

n is an integer of 0 to 4, provided that when X is a bond, n is not zero;

Q is a moiety having a structure selected from those illustrated in formula (4)

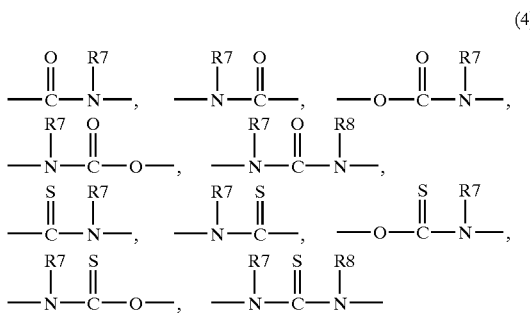
(4)

wherein R[7] and R[8] are independently hydrogen or an optionally substituted alkyl having 1 to 4 carbons;

R[1] and R[2] are independently a hydrogen atom, a halogen atom, a hydroxyl group, amino group, an alkyl group having 1 to 4 carbons, an alkoxy group having 1 to 4 carbons, an aminoalkyl group having 1 to 4 carbons, an alkylamino group having 1 to 4 carbons, an acyl group having 1 to 4 carbons, an acylamino group having 1 to 4 carbons, an alkylthio group having 1 to 4 carbons, a perfluoroalkyl group having 1 to 4 carbons, a perfluoroalkyloxy group having 1 to 4 carbons, a carboxyl group or an alkoxycarbonyl group having 1 to 4 carbons;

R[3] is a hydroxyl or amino group.

This invention also provides an anilide having the structure represented by formula (13)

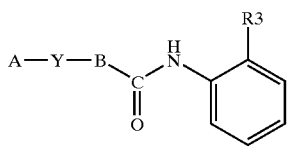
(13)

wherein A and R[3] are as defined above; B is an optionally substituted a phenyl or heterocycle group; Y is a moiety having —CO—, —CS—, —SO— or —SO$_2$— which is linear, cyclic or their combination and links A and B; and in which the distances between the centroid of ring B (W1), the centroid of ring A (W2) and an oxygen or sulfur atom as a hydrogen bond acceptor in the moiety Y (W3) can be as follows; W1–W2=6.0 to 11.0 Å, W1–W3=3.0 to 8.0 Å, and W2–W3=3.0 to 8.0 Å; preferably W1–W2=7.0 to 9.5 Å; W1–W3 is 3.0 to 5.0 Å; and W2–W3 is 5.0–8.0 Å; or a pharmaceutically acceptable salt thereof.

The novel benzamide derivative and the novel anilide derivative of this invention have differentiation-inducing effect and are useful as a drug such as a therapeutic or improving agent for malignant tumors, autoimmune diseases, dermatologic diseases and parasitism. In particular, they are highly effective as a carcinostatic agent, specifically to a hematologic malignancy and a solid carcinoma.

BRIEF DESCRIPTION OF THE DRAWINGS

FIG. 1 shows a change of the volume of the tumor when the compound of Example 48 was administered against the tumor cell HT-29.

FIG. 2 shows a change of the volume of the tumor when the compound of Example 48 was administered against the tumor cell KB-3-1.

DETAILED DESCRIPTION OF THE INVENTION AND PREFERRED EMBODIMENTS

In the above formula (1), n may be zero or an integer of 1 to 4.

Q in the above formula (1) may be any structure illustrated in formula (5);

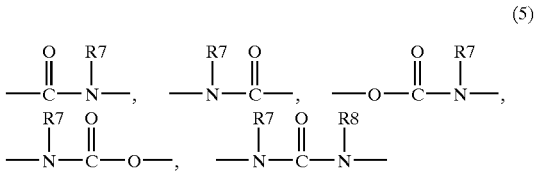
(5)

wherein R[7] and R[8] are as defined above.

X in the above formula (1) may be a moiety having the structure represented by formula (6);

—(CH$_2$)e-              (6)

wherein e is as defined above.

X in the above formula (1) may be also a moiety having any structure illustrated in formula (7);

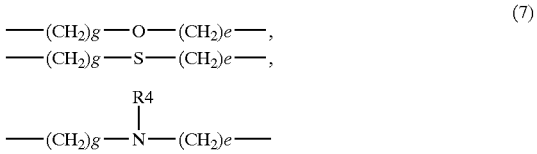
(7)

wherein e, g and R[4] areas defined above.

X in the above formula (1) may be also a moiety having any structure illustrated in formula (8);

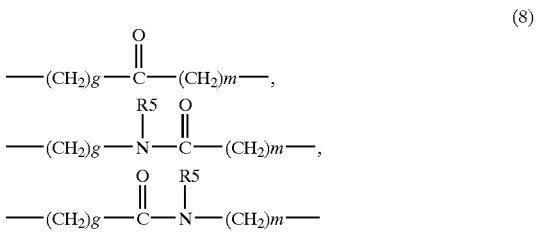
(8)

wherein g, m and R[5] are as defined above.

The anilide represented by formula (13) may be one wherein A is an optionally substituted heterocycle; B is an optionally substituted phenyl; and R[3] is an amino group.

The anilide may be also one wherein Y has —CO— and is linear, cyclic or their combination.

As used herein, "1 to 4 carbons" means a carbon number per a single substituent; for example, for dialkyl substitution it means 2 to 8 carbons.

A heterocycle in the compound represented by formula (1) or (13) is a monocyclic heterocycle having 5 or 6 members containing 1 to 4 nitrogen, oxygen or sulfur atoms or a bicyclic-fused heterocycle. The monocyclic heterocycle includes pyridine, pyrazine, pyrimidine, pyridazine, thiophene, furan, pyrrole, pyrazole, isoxazole, isothiazole, imidazole, oxazole, thiazole, piperidine, piperazine, pyrrolidine, quinuclidine, tetrahydrofuran, morpholine, thiomorpholine and the like. The bicyclic fused heterocycle includes. quinoline; isoquinoline; naphthyridine; fused pyridines such as furopyridine, thienopyridine, pyrrolopyridine, oxazolopyridine, imidazolopyridine and thiazolopyridine; benzofuran; benzothiophene; benzimidazole and the like.

A halogen may be fluorine, chlorine, bromine or iodine.

An alkyl having 1 to 4 carbons includes methyl, ethyl, n-propyl, isopropyl, n-butyl, isobutyl, sec-butyl and tert-butyl.

An alkoxy having 1 to 4 carbons includes methoxy, ethoxy, n-propoxy, isopropoxy, allyloxy, n-butoxy, isobutoxy, sec-butoxy, tert-butoxy and the like.

An aminoalkyl having 1 to 4 carbons includes aminomethyl, 1-aminoethyl, 2-aminopropyl and the like.

An alkylamino having 1 to 4 carbons includes N-methylamino, N,N-dimethylamino, N,N-diethylamino, N-methyl-N-ethylamino, N,N-diisopropylamino and the like.

An acyl having 1 to 4 carbons includes acetyl, propanoyl, butanoyl and like.

An acylamino having 1 to 4 carbons includes acetylamino, propanoylamino, butanoylamino and the like.

An alkylthio having 1 to 4 carbons includes methylthio, ethylthio, propylthio and the like.

A perfluoroalkyl having 1 to 4 carbons includes trifluoromethyl, pentafluoroethyl and the like.

A perfluoroalkyloxy having 1 to 4 carbons includes trifluoromethoxy, pentafluoroethoxy and the like.

An alkoxycarbonyl having 1 to 4 carbons includes methoxycarbonyl and ethoxycarbonyl.

An optionally substituted alkyl having 1 to 4 carbons includes methyl, ethyl, n-propyl, isopropyl, n-butyl, isobutyl, sec-butyl and tert-butyl and these having 1 to 4 substituents selected from the group consisting of a halogen, hydroxyl, amino, nitro, cyano, phenyl and a heterocycle.

As described below, important elements in the compound represented by formula (13) are (a) presence of ring A, ring B and oxygen or sulfur atom as a hydrogen bond acceptor, and (b) the distances between them determined by their steric configurations. There may be, therefore, no limitation as long as the structure of Y has a hydrogen bond accptor and rings A and B have required steric configurations. Specifically, the structure of Y which has —CO—, —CS—, —SO— or —SO$_2$— and links A and B and which is linear, cyclic or their combination, means either (a) one consisting of carbon and/or hetero atoms linking A and B, whose linear or branched moiety has —CO—, —CS—, —SO— or —SO$_2$—; (b) one linking A and B, whose cyclic moiety has —CO—, —CS—, —SO— or —SO$_2$—; and (c) one linking A and B where in a combination of cyclic and linear moieties form a structural unit having —CO—, —CS—, —SO— or —SO$_2$—.

A basic cyclic structure includes cyclic moieties having 4 to 7 members containing carbons and/or hetero atoms or their fused cycles. For example it may be cyclobutane, cyclopentane, cyclohexane, cycloheptane, oxetane, oxolane, oxane, oxepane, pyrrolidine, imidazolidine, pyrazolidine, piperidine, piperazine, indoline, isoindoline, thiolane, thiazolidine and oxazolidine rings, which may contain unsaturated bonds, hydrogen bond acceptors and/or substituents.

Structural analyses considering degree of conformational freedom of the compound represented by formula (13) have indicated that atomic groups possibly involved in an biomolecule-drug interaction such as a hydrophobic interaction and hydrogen bond may have a particular spatial configuration in a compound showing high differentiation-inducing effect.

Specifically, we formed a three-dimensional structure of a high activity compound using a molecular modeling software, SYBYL 6.3, and analyzed conformations for all rotatable bonds to determine the most stable structure, wherein their energy levels were evaluated by using Tripos force field after allocating charge on each atom according to Gasteiger-Huckel method. Then, starting with the most stable structure, we have performed a superimposition taking its conformation into consideration using DISCO/SYBYL and then have found that a particular spatial configuration is necessary for expression of high differentiation-inducing effect.

In the above analyses, other commercially available program packages such as CATALYST(MSI), Cerius 2/QSAR+(MSI) and SYBYL/DISCO(Tripos) may be used, and the information on distance obtained in this invention is not limited to that from a particular calculation program.

The ring centroid used in definition of the spatial configuration may be defined as an average of X, Y and Z axes of the ring-forming atoms. When a ring structure to be calculated is fused-polycyclic, the centroid of either the overall fused ring or of a partial ring may be used as that for defining the space.

"Possibility of formation of a configuration" means that a conformer filling the spatial configuration is within 15 kcal/mol, preferably 8 kcal/mol from the energetically most stable structure.

Specific calculation can be performed as described in the instructions for Sybyl (M. Clark) or J. Comput. Chem. 10, 982(1989).

A pharmaceutically acceptable salt of the compound of this invention includes salts with an inorganic acid, such as hydrochloric acid, hydrobromic acid, sulfuric acid and phosphoric acid; and with an organic acid such as acetic acid, lactic acid, tartaric acid, malic acid, succinic acid, fumaric acid, maleic acid, citric acid, benzoic acid, trifluroacetic acid, p-toluenesulfonic acid and methanesulfonic acid. Such a salt includes N-(2-aminophenyl)-4-[N-(pyridin-3-yl)methoxycarbonylaminomethyl]benzamide hydrochloride, N-(2-aminophenyl)-4-[N-(pyridin-3-yl)methoxycarbonylaminomethyl]benzamide hydrobromide, N-(2-aminophenyl)-4-[N-(pyridin-3-yl)methoxycarbonylaminomethyl]benzamide sulfate, N-(2-aminophenyl)-4-[N-(pyridin-3-yl)methoxycarbonylaminomethyl]benzamide phosphate, N-(2-aminophenyl)-4-[N-(pyridin-3-yl)methoxycarbonylaminomethyl]benzamide acetate, N-(2-aminophenyl)-4-[N-(pyridin-3-yl)methoxycarbonylaminomethyl]benzamide lactate, N-(2-aminophenyl)-4-[N-(pyridin-3-yl)methoxycarbonylaminomethyl)benzamide tartrate, N-(2-aminophenyl)-4-[N-(pyridin-3-yl)methoxycarbonylaminomethyl]benzamide malate, N-(2-aminophenyl)-4-[N-(pyridin-3-yl)methoxycarbonylaminomethyl]benzamide succinate, N-(2-aminophenyl)-4-[N-(pyridin-3-yl)methoxycarbonylaminomethyl]benzamide fumarate, N-(2-aminophenyl)-4-[N-(pyridin-3-yl)methoxycarbonylaminomethyl]benzamide maleate, N-(2-aminophenyl)-4-[N-(pyridin-3-yl)methoxycarbonylaminomethyl]benzamide citrate, N-(2-aminophenyl)-4-[N-(pyridin-3-yl)methoxycarbonylaminomethyl]benzamide trifluoroacetate, N-(2-aminophenyl)-4-[N-(pyridin-3-yl)methoxycarbonylaminomethyl]benzamide p-toluenesulfonate and N-(2-aminophenyl)-4-[N-(pyridin-3-yl)methoxycarbonylaminomethyl]benzamide methanesulfonate.

As used herein, a "drug" includes a therapeutic and/or improving agent to, for example, an autoimmune disease, dermatologic disease or parasitism, in addition to a anticancer drug.

When having asymmetric carbon or carbons, the compound represented by formula (1) or (13) may be obtained as an individual stereoisomer or a mixture of stereoisomers including a racemic modification. This invention encompasses the above-specified different forms, which may be also used as an active ingredient.

Representative compounds of this invention represented by formula (1) or (13) are specifically shown in Tables 1 to 4, but this invention is not intended to be limited to these.

TABLE 1

A—X—Q—(CH$_2$)$_n$—[phenyl with R1]—C(=O)—NH—[phenyl with R2, R3]

| Compound No. | A | X | Q | n | R1 | R2 | R3 |
|---|---|---|---|---|---|---|---|
| 1 | phenyl | Direct bond | —C(=O)—NH— | 1 | H | H | NH$_2$ |
| 2 | phenyl | —CH$_2$— | —C(=O)—NH— | 0 | H | H | NH$_2$ |
| 3 | phenyl | —(CH$_2$)$_2$— | —C(=O)—NH— | 0 | H | H | NH$_2$ |
| 4 | phenyl | —(CH$_2$)$_3$— | —C(=O)—NH— | 0 | H | H | NH$_2$ |
| 5 | phenyl | —(CH$_2$)$_4$— | —C(=O)—NH— | 0 | H | H | NH$_2$ |
| 6 | phenyl | —CH$_2$— | —C(=O)—NH— | 1 | H | H | NH$_2$ |
| 7 | phenyl | —(CH$_2$)$_2$— | —C(=O)—NH— | 1 | H | H | NH$_2$ |
| 8 | phenyl | —CH$_2$— | —NH—C(=O)— | 0 | H | H | NH$_2$ |
| 9 | phenyl | —(CH$_2$)$_2$— | —NH—C(=O)— | 0 | H | H | NH$_2$ |
| 10 | phenyl | Direct bond | —C(=S)—NH— | 1 | H | H | NH$_2$ |
| 11 | phenyl | —CH$_2$— | —O—C(=O)—NH— | 1 | H | H | NH$_2$ |
| 12 | phenyl | Direct bond | —O—C(=O)—NH— | 1 | H | H | NH$_2$ |

TABLE 1-continued
| Compound No. | A | X | Q | n | R1 | R2 | R3 |
|---|---|---|---|---|---|---|---|
| 13 | 4-F-C6H4- | Direct bond | -C(O)-NH- | 1 | H | H | NH$_2$ |
| 14 | 2-Cl-C6H4- | Direct bond | -C(O)-NH- | 1 | H | H | NH$_2$ |
| 15 | 4-Cl-C6H4- | -CH$_2$- | -C(O)-NH- | 0 | H | H | NH$_2$ |
| 16 | 4-Br-C6H4- | Direct bond | -C(O)-NH- | 1 | H | H | NH$_2$ |
| 17 | 4-HO-C6H4- | Direct bond | -C(O)-NH- | 1 | H | H | NH$_2$ |
| 18 | 2-NO$_2$-C6H4- | Direct bond | -C(O)-NH- | 1 | H | H | NH$_2$ |
| 19 | 2-NO$_2$-C6H4- | -CH$_2$- | -C(O)-NH- | 0 | H | H | NH$_2$ |
| 20 | 3-O$_2$N-C6H4- | Direct bond | -NH-C(S)-NH- | 1 | H | H | NH$_2$ |
| 21 | 4-O$_2$N-C6H4- | -CH$_2$- | -C(O)-NH- | 0 | H | H | NH$_2$ |
| 22 | 2-NH$_2$-C6H4- | -CH$_2$- | -C(O)-NH- | 0 | H | H | NH$_2$ |
| 23 | 3-H$_2$N-C6H4- | -CH$_2$- | -C(O)-NH- | 1 | H | H | NH$_2$ |

TABLE 1-continued

A—X—Q—(CH₂)n—[phenyl with R1 at 5,6 positions]—C(=O)—NH—[phenyl with R3 at 2,3 and R2 at 4,5]

| Compound No. | A | X | Q | n | R1 | R2 | R3 |
|---|---|---|---|---|---|---|---|
| 24 | 3-H₂N-phenyl | Direct bond | —NH—C(=O)—NH— | 1 | H | H | NH₂ |
| 25 | 3-H₂N-phenyl | Direct bond | —NH—C(=S)—NH— | 1 | H | H | NH₂ |
| 26 | 4-H₂N-phenyl | —CH₂— | —C(=O)—NH— | 0 | H | H | NH₂ |
| 27 | 4-NC-phenyl | Direct bond | —C(=O)—NH— | 1 | H | H | NH₂ |
| 28 | 4-H₃C-phenyl | Direct bond | —C(=O)—NH— | 1 | H | H | NH₂ |
| 29 | 4-C₂H₅-phenyl | Direct bond | —C(=O)—NH— | 1 | H | H | NH₂ |
| 30 | 3-H₃CO-phenyl | Direct bond | —C(=O)—NH— | 1 | H | H | NH₂ |
| 31 | 4-H₃CO-phenyl | Direct bond | —C(=O)—NH— | 1 | H | H | NH₂ |
| 32 | 4-H₃CO-phenyl | —CH₂— | —C(=O)—NH— | 0 | H | H | NH₂ |
| 33 | 3,4,5-tri(H₃CO)-phenyl | Direct bond | —C(=O)—NH— | 1 | H | H | NH₂ |

TABLE 1-continued

A—X—Q—(CH₂)n-[phenyl with R1 at 5, positions 2,3,4,6]—C(=O)—NH—[phenyl with R3 at 2, R2 at 4, positions 3,5,6]

| Compound No. | A | X | Q | n | R1 | R2 | R3 |
|---|---|---|---|---|---|---|---|
| 34 | 3,4,5-trimethoxyphenyl (H₃CO, H₃CO, H₃CO) | —CH₂— | —O—C(=O)—NH— | 1 | H | H | NH₂ |
| 35 | 4-(H₃CHN)-phenyl | Direct bond | —C(=O)—NH— | 1 | H | H | NH₂ |
| 36 | 4-((H₃C)₂N)-phenyl | Direct bond | —C(=O)—NH— | 1 | H | H | NH₂ |
| 37 | 3-(H₂N-CH₂)-phenyl | Direct bond | —NH—C(=O)—NH— | 1 | H | H | NH₂ |
| 38 | 4-(H₃CHN-C(=O))-phenyl | —CH₂— | —O—C(=O)—NH— | 1 | H | H | NH₂ |
| 39 | 4-(H₃C-C(=O)-NH)-phenyl | —CH₂— | —O—C(=O)—NH— | 1 | H | H | NH₂ |
| 40 | 4-(H₃C-C(=O))-phenyl | Direct bond | —C(=O)—NH— | 1 | H | H | NH₂ |
| 41 | 4-(H₃CS)-phenyl | Direct bond | —C(=O)—NH— | 1 | H | H | NH₂ |
| 42 | 4-(F₃C)-phenyl | Direct bond | —C(=O)—NH— | 1 | H | H | NH₂ |
| 43 | 4-(F₃C)-phenyl | —CH₂— | —C(=O)—NH— | 0 | H | H | NH₂ |
| 44 | 4-(F₃CO)-phenyl | Direct bond | —C(=O)—NH— | 1 | H | H | NH₂ |

TABLE 1-continued

A—X—Q—(CH₂)n— [phenyl ring with R1 at 5,6 positions]—C(O)—NH—[phenyl ring with R3 at 2, R2 at 4]

| Compound No. | A | X | Q | n | R1 | R2 | R3 |
|---|---|---|---|---|---|---|---|
| 45 | 4-(HO₂C)-phenyl- | Direct bond | —C(O)—NH— | 1 | H | H | NH₂ |
| 46 | 4-(H₃CO₂C)-phenyl- | Direct bond | —C(O)—NH— | 1 | H | H | NH₂ |
| 47 | 4-(imidazol-1-yl)-phenyl- | —CH₂— | —O—C(O)—NH— | 1 | H | H | NH₂ |
| 48 | phenyl- | —O—CH₂— | —C(O)—NH— | 1 | H | H | NH₂ |
| 49 | phenyl- | —S—CH₂— | —C(O)—NH— | 1 | H | H | NH₂ |
| 50 | phenyl- | —NH—CH₂— | —C(O)—NH— | 1 | H | H | NH₂ |
| 51 | 2-aminophenyl- | —CH₂— | —O—C(O)—NH— | 1 | H | H | NH₂ |
| 52 | 3-aminophenyl- | —CH₂— | —O—C(O)—NH— | 1 | H | H | NH₂ |
| 53 | 4-((H₃C)₂N)-phenyl- | —CH₂— | —C(O)—NH— | 0 | H | H | NH₂ |
| 54 | 4-(O₂N)-phenyl- | —O—CH₂— | —C(O)—NH— | 0 | H | H | NH₂ |
| 55 | 4-(H₂N)-phenyl- | —O—CH₂— | —C(O)—NH— | 0 | H | H | NH₂ |
| 56 | 3-aminophenyl- | —O—CH₂— | —C(O)—NH— | 1 | H | H | NH₂ |

TABLE 1-continued

| Compound No. | A | X | Q | n | R1 | R2 | R3 |
|---|---|---|---|---|---|---|---|
| 57 | 3-aminophenyl | —O—CH₂— | —C(O)—NH— | 1 | H | 5-F | NH₂ |
| 58 | 3-aminophenyl | —CH₂—O—CH₂— | —C(O)—NH— | 0 | H | H | NH₂ |
| 59 | phenyl | —N(COCH₃)—CH₂— | —C(O)—NH— | 1 | H | H | NH₂ |
| 60 | phenyl | —N(COC₆H₅)—CH₂— | —C(O)—NH— | 1 | H | H | NH₂ |
| 61 | 3-pyridyl | —O—CH₂— | —C(O)—NH— | 1 | H | H | NH₂ |
| 62 | 3-pyridyl | —O—(CH₂)₂— | —C(O)—NH— | 1 | H | H | NH₂ |
| 63 | 3-pyridyl | —NH—CH₂— | —C(O)—NH— | 1 | H | H | NH₂ |
| 64 | 3-pyridyl | —S—CH₂— | —C(O)—NH— | 1 | H | H | NH₂ |
| 65 | 3-pyridyl | —O—CH₂— | —C(O)—NH— | 0 | H | H | NH₂ |
| 66 | 3-pyridyl | —O—(CH₂)₂— | —C(O)—NH— | 0 | H | H | NH₂ |
| 67 | 3-pyridyl | —O—(CH₂)₂— | —O—C(O)—NH— | 0 | H | H | NH₂ |

TABLE 1-continued
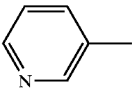
| Compound No. | A | X | Q | n | R1 | R2 | R3 |
|---|---|---|---|---|---|---|---|
| 68 | 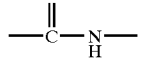 | —CH$_2$— | 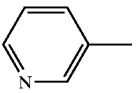 | 0 | H | H | NH$_2$ |
| 69 |  | —(CH$_2$)$_2$— | 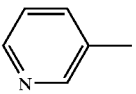 | 0 | H | H | NH$_2$ |
| 70 | 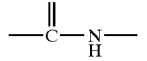 | —(CH$_2$)$_2$— | 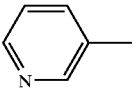 | 0 | H | H | NH$_2$ |
| 71 | 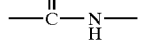 | Direct bond | 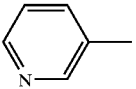 | 1 | H | H | NH$_2$ |
| 72 | 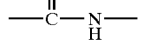 | Direct bond | 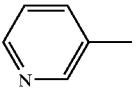 | 2 | H | H | NH$_2$ |
| 73 | 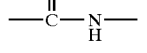 | Direct bond | 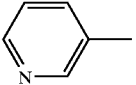 | 3 | H | H | NH$_2$ |
| 74 | 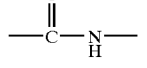 | —CH$_2$— | 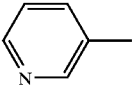 | 1 | H | H | NH$_2$ |
| 75 | 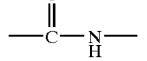 | —(CH$_2$)$_2$— | 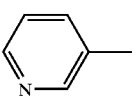 | 1 | H | H | NH$_2$ |
| 76 | 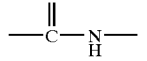 | —(CH$_2$)$_3$— | 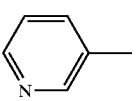 | 1 | H | H | NH$_2$ |
| 77 | 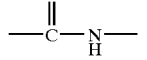 | —CH$_2$— | 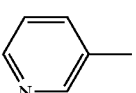 | 2 | H | H | NH$_2$ |
| 78 | 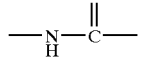 | —CH$_2$— | 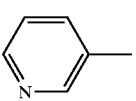 | 1 | H | H | NH$_2$ |
| 79 | 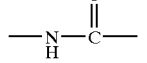 | Direct bond | | 2 | H | H | NH$_2$ |

TABLE 1-continued
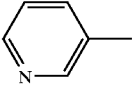
| Compound No. | A | X | Q | n | R1 | R2 | R3 |
|---|---|---|---|---|---|---|---|
| 80 | 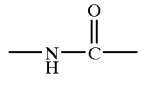 | —CH₂— | 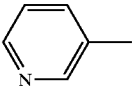 | 2 | H | H | NH₂ |
| 81 | 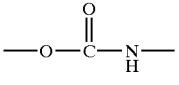 | Direct bond | 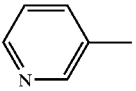 | 1 | H | H | NH₂ |
| 82 | 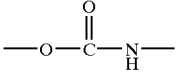 | —CH₂— | 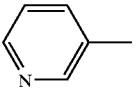 | 1 | H | H | NH₂ |
| 83 | 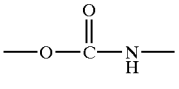 | —(CH₂)₂— | 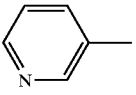 | 1 | H | H | NH₂ |
| 84 | 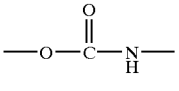 | —(CH₂)₃— | 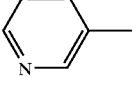 | 1 | H | H | NH₂ |
| 85 | 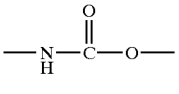 | —CH₂— | 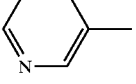 | 1 | H | H | NH₂ |
| 86 | 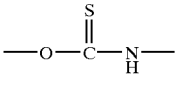 | —CH₂— | 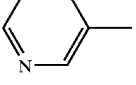 | 1 | H | H | NH₂ |
| 87 | 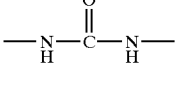 | Direct bond | 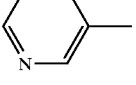 | 1 | H | H | NH₂ |
| 88 | 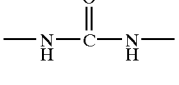 | —CH₂— | 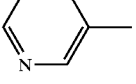 | 1 | H | H | NH₂ |
| 89 | 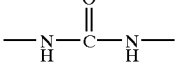 | —(CH₂)₂— | 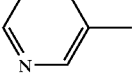 | 1 | H | H | NH₂ |
| 90 | 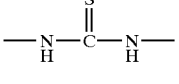 | —CH₂— | | 1 | H | H | NH₂ |

TABLE 1-continued

A—X—Q—(CH$_2$)$_n$-[phenyl with R1 at 5,6 positions]-C(=O)-NH-[phenyl with R3 at 2,3 and R2 at 4]

| Compound No. | A | X | Q | n | R1 | R2 | R3 |
|---|---|---|---|---|---|---|---|
| 91 | 3-pyridyl | —O—CH$_2$— | —C(=O)—N(—(CH$_2$)$_3$-3-pyridyl)— | 1 | H | H | NH$_2$ |
| 92 | 3-pyridyl | —O—CH$_2$— | —C(=O)—N(CH$_3$)— | 1 | H | H | NH$_2$ |
| 93 | 3-pyridyl | —O—CH$_2$— | —C(=O)—NH— | 1 | H | H | OH |
| 94 | 3-pyridyl | —NH—C(=O)—CH$_2$— | —C(=O)—NH— | 0 | H | H | NH$_2$ |
| 95 | 3-pyridyl | —NH—C(=O)— | —C(=O)—NH— | 1 | H | H | NH$_2$ |
| 96 | 3-pyridyl | —NH—CH$_2$— | —C(=O)—NH— | 1 | H | H | NH$_2$ |
| 97 | 3-pyridyl | —C(=O)—NH—CH$_2$— | —C(=O)—NH— | 0 | H | H | NH$_2$ |
| 98 | 3-pyridyl | —C(=O)—CH$_2$— | —C(=O)—NH— | 1 | H | H | NH$_2$ |
| 99 | 3-pyridyl | —C(=O)—(CH$_2$)$_2$— | —C(=O)—NH— | 0 | H | H | NH$_2$ |
| 100 | 3-pyridyl | —C(=O)—(CH$_2$)$_2$— | —C(=O)—NH— | 1 | H | H | NH$_2$ |
| 101 | 3-pyridyl | —CH$_2$—O—CH$_2$— | —C(=O)—NH— | 0 | H | H | NH$_2$ |

TABLE 1-continued

| Compound No. | A | X | Q | n | R1 | R2 | R3 |
|---|---|---|---|---|---|---|---|
| 102 | 3-pyridyl | —CH₂—O—CH₂— | —C(O)—NH— | 0 | 3-CH₃ | H | NH₂ |
| 103 | 3-pyridyl | —CH₂—O—CH₂— | —C(O)—N(CH₃)— | 0 | H | H | NH₂ |
| 104 | 3-pyridyl | —CH₂—NH—C(O)— | —C(O)—NH— | 0 | H | H | NH₂ |
| 105 | 3-pyridyl | —CH₂—NH—CH₂— | —C(O)—NH— | 0 | H | H | NH₂ |
| 106 | 3-pyridyl | —CH₂—N(nicotinoyl)—CH₂— | —C(O)—NH— | 0 | H | H | NH₂ |
| 107 | 3-pyridyl | —CH₂—N(COCF₃)—CH₂— | —C(O)—NH— | 1 | H | H | NH₂ |
| 108 | 3-pyridyl | —CH₂—N(CH₃)—CH₂— | —C(O)—NH— | 0 | H | H | NH₂ |
| 109 | 3-pyridyl | —CH₂— | —O—C(O)—N(CH₂-3-pyridyl)— | 1 | H | H | NH₂ |
| 110 | 3-pyridyl | —CH₂— | —O—C(O)—NH— | 1 | H | 5-F | NH₂ |
| 111 | 3-pyridyl | —CH₂— | —O—C(O)—NH— | 1 | H | H | OH |
| 112 | 3-pyridyl | —CH₂— | —NH—C(O)—NH— | 1 | H | 5-F | NH₂ |

TABLE 1-continued

A—X—Q—(CH$_2$)$n$—[phenyl with R1]—C(O)NH—[phenyl with R2, R3]

| Compound No. | A | X | Q | n | R1 | R2 | R3 |
|---|---|---|---|---|---|---|---|
| 113 | 3-pyridyl | —CH$_2$— | —O—C(O)—NH— | 1 | H | 4-Cl | NH$_2$ |
| 114 | 3-pyridyl | —CH$_2$— | —NH—C(O)—NH— | 1 | H | H | OH |
| 115 | 3-pyridyl | —CH$_2$— | —O—C(O)—N(CH$_2$-3-pyridyl)— | 1 | H | H | OH |
| 116 | 3-pyridyl | —CH$_2$— | —O—C(O)—NH— | 1 | H | 4-OH | OH |
| 117 | 3-pyridyl | —CH$_2$— | —C(O)—NH— | 1 | H | H | OH |
| 118 | 3-pyridyl | —CH$_2$— | —O—C(O)—NH— | 1 | H | 5-CH$_3$ | OH |
| 119 | 3-pyridyl | —CH$_2$— | —O—C(O)—NH— | 1 | H | 5-OCH$_3$ | OH |
| 120 | 3-pyridyl | —CH$_2$— | —O—C(O)—N((CH$_2$)$_3$-3-pyridyl)— | 1 | H | H | NH$_2$ |
| 121 | 3-pyridyl | —CH$_2$— | —O—C(O)—NH— | 1 | H | 5-OCH$_3$ | NH$_2$ |
| 122 | 3-pyridyl | —(CH$_2$)$_2$— | —O—C(O)—NH— | 0 | H | 5-F | NH$_2$ |

TABLE 1-continued

| Compound No. | A | X | Q | n | R1 | R2 | R3 |
|---|---|---|---|---|---|---|---|
| 123 | 3-pyridyl | —(CH₂)₂— | —C(O)—NH— | 0 | 3-Cl | H | NH₂ |
| 124 | 3-pyridyl | —(CH₂)₂— | —O—C(O)—NH— | 0 | H | H | NH₂ |
| 125 | 3-pyridyl | —(CH₂)₂— | —C(O)—NH— | 1 | H | H | OH |
| 126 | 3-pyridyl | —C(O)— | —NH—C(O)—NH— | 1 | H | H | NH₂ |
| 127 | 3-pyridyl | —C(O)— | —C(O)—NH— | 1 | H | H | NH₂ |
| 128 | 3-pyridyl | —O—CH₂— | —C(O)—NH— | 1 | 2-Cl | H | NH₂ |
| 129 | 3-pyridyl | —O—CH₂— | —C(O)—NH— | 1 | H | 5-F | NH₂ |
| 130 | 3-pyridyl | —O—CH₂— | —C(O)—NH— | 1 | H | 5-OCH₃ | NH₂ |
| 131 | 4-amino-3-pyridyl | —CH₂— | —O—C(O)—NH— | 1 | H | H | NH₂ |
| 132 | 4-amino-3-pyridyl | —O—CH₂— | —C(O)—NH— | 1 | H | H | NH₂ |
| 133 | 4-amino-3-pyridyl | —CH₂—O—CH₂— | —C(O)—NH— | 1 | H | H | NH₂ |

TABLE 1-continued

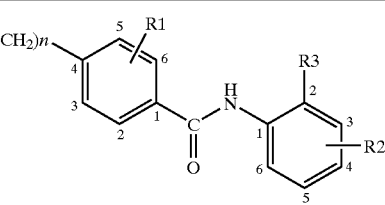

| Compound No. | A | X | Q | n | R1 | R2 | R3 |
|---|---|---|---|---|---|---|---|
| 134 | 4-N(CH₃)₂, 3-methyl pyridine | —CH₂— | —O—C(=O)—NH— | 1 | H | H | NH₂ |
| 135 | 4-N(CH₃)₂, 3-methyl pyridine | —O—CH₂— | —C(=O)—NH— | 1 | H | H | NH₂ |
| 136 | 4-N(CH₃)₂, 3-methyl pyridine | —CH₂—O—CH₂— | —C(=O)—NH— | 1 | H | H | NH₂ |
| 137 | 4-OCH₃, 3-methyl pyridine | —CH₂— | —O—C(=O)—NH— | 1 | H | H | NH₂ |
| 138 | 4-OCH₃, 3-methyl pyridine | —O—CH₂— | —C(=O)—NH— | 1 | H | H | NH₂ |
| 139 | 4-OCH₃, 3-methyl pyridine | —CH₂—O—CH₂— | —C(=O)—NH— | 1 | H | H | NH₂ |
| 140 | 4-OCH₃, 3-methyl pyridine | —CH₂— | —O—C(=O)—NH— | 1 | H | 5-F | NH₂ |
| 141 | 2-CH₃, 3-methyl pyridine | Direct bond | —C(=O)—NH— | 1 | H | H | NH₂ |
| 142 | 2-CH₃, 3-methyl pyridine | —CH₂— | —O—C(=O)—NH— | 1 | H | H | NH₂ |

TABLE 1-continued

A—X—Q—(CH₂)n-[phenyl with R1]—C(O)NH—[phenyl with R2, R3]

| Compound No. | A | X | Q | n | R1 | R2 | R3 |
|---|---|---|---|---|---|---|---|
| 143 | 2-methyl-5-pyridyl (H₃C on pyridine) | Direct bond | —C(O)—NH— | 1 | H | H | NH₂ |
| 144 | 2-methyl-5-pyridyl | —CH₂— | —O—C(O)—NH— | 1 | H | H | NH₂ |
| 145 | 4-methyl-3-pyridyl | —CH₂— | —O—C(O)—NH— | 1 | H | H | NH₂ |
| 146 | 4-methyl-3-pyridyl | —CH₂— | —NH—C(O)—NH— | 1 | H | H | NH₂ |
| 147 | 5-methyl-3-pyridyl | —CH₂— | —O—C(O)—NH— | 1 | H | H | NH₂ |
| 148 | 5-methyl-3-pyridyl | —CH₂— | —NH—C(O)—O— | 1 | H | H | NH₂ |
| 149 | 5-methyl-3-pyridyl | —CH₂— | —NH—C(O)—NH— | 1 | H | H | NH₂ |
| 150 | 5-methyl-3-pyridyl | —(CH₂)₂— | —C(O)—NH— | 1 | H | H | NH₂ |
| 151 | 5-methyl-3-pyridyl | —(CH₂)₂— | —C(O)—NH— | 1 | H | H | NH₂ |

TABLE 1-continued

A—X—Q—(CH₂)n— [aryl-C(O)NH-aryl core structure with positions labeled]

| Compound No. | A | X | Q | n | R1 | R2 | R3 |
|---|---|---|---|---|---|---|---|
| 152 | 3-methyl-5-methylpyridine | —(CH₂)₂— | —NH—C(O)— | 0 | H | H | NH₂ |
| 153 | 3-methyl-5-methylpyridine | —CH₂— | —NH—C(O)— | 2 | H | H | NH₂ |
| 154 | 2-chloro-3-methylpyridine | Direct bond | —C(O)—NH— | 1 | H | H | NH₂ |
| 155 | 2-chloro-3-methylpyridine | —CH₂— | —O—C(O)—NH— | 1 | H | H | NH₂ |
| 156 | 2-chloro-5-methylpyridine | Direct bond | —C(O)—NH— | 1 | H | H | NH₂ |
| 157 | 2-chloro-5-methylpyridine | —CH₂— | —O—C(O)—NH— | 1 | H | H | NH₂ |
| 158 | 3-chloro-5-methylpyridine | —O—CH₂— | —C(O)—NH— | 1 | H | H | NH₂ |
| 159 | 3-chloro-5-methylpyridine | —O—CH₂— | —O—C(O)—NH— | 1 | H | H | NH₂ |
| 160 | 3-bromo-5-methylpyridine | —CH₂— | —O—C(O)—NH— | 1 | H | H | NH₂ |

TABLE 1-continued

A—X—Q—(CH₂)n-[phenyl(R1)]-C(O)NH-[phenyl(R2,R3)]

| Compound No. | A | X | Q | n | R1 | R2 | R3 |
|---|---|---|---|---|---|---|---|
| 161 | H₃CO-pyridyl | —CH₂— | —O—C(=O)—NH— | 1 | H | H | NH₂ |
| 162 | H₃CO-pyridyl | —CH₂— | —NH—C(=O)—O— | 1 | H | H | NH₂ |
| 163 | H₃CO-pyridyl | —CH₂— | —NH—C(=O)—NH— | 1 | H | H | NH₂ |
| 164 | H₃CO-pyridyl | —(CH₂)₂— | —C(=O)—NH— | 1 | H | H | NH₂ |
| 165 | H₃CO-pyridyl | —(CH₂)₂— | —C(=O)—NH— | 1 | H | H | NH₂ |
| 166 | H₃CO-pyridyl | —(CH₂)₂— | —NH—C(=O)— | 0 | H | H | NH₂ |
| 167 | H₃CO-pyridyl | —CH₂— | —NH—C(=O)— | 2 | H | H | NH₂ |
| 168 | C₂H₅O-pyridyl | —CH₂— | —O—C(=O)—NH— | 1 | H | H | NH₂ |
| 169 | H₃CS-pyridyl | —CH₂— | —O—C(=O)—NH— | 1 | H | H | NH₂ |

TABLE 1-continued

A—X—Q—(CH₂)n-[phenyl with R1]-C(=O)-NH-[phenyl with R3, R2]

| Compound No. | A | X | Q | n | R1 | R2 | R3 |
|---|---|---|---|---|---|---|---|
| 170 | 5-amino-3-pyridyl (H₂N-pyridine) | —CH₂— | —O—C(=O)—NH— | 1 | H | H | NH₂ |
| 171 | 2-pyridyl | —CH₂— | —O—C(=O)—NH— | 1 | H | H | NH₂ |
| 172 | 2-pyridyl | —(CH₂)₂— | —O—C(=O)—NH— | 1 | H | H | NH₂ |
| 173 | 2-pyridyl | Direct bond | —C(=O)—NH— | 1 | H | H | NH₂ |
| 174 | 2-pyridyl | —CH₂— | —C(=O)—NH— | 0 | H | H | NH₂ |
| 175 | 2-pyridyl | —O—CH₂— | —C(=O)—NH— | 1 | H | 5-OCH₃ | NH₂ |
| 176 | 2-pyridyl | —CH₂—O—CH₂— | —C(=O)—NH— | 0 | H | H | NH₂ |
| 177 | 6-methyl-2-pyridyl | —CH₂— | —C(=O)—NH— | 0 | H | H | NH₂ |
| 178 | 6-methyl-2-pyridyl | Direct bond | —C(=O)—NH— | 1 | H | H | NH₂ |
| 179 | 6-methyl-2-pyridyl | —CH₂— | —O—C(=O)—NH— | 1 | H | H | NH₂ |
| 180 | 6-chloro-2-pyridyl | —CH₂— | —O—C(=O)—NH— | 1 | H | H | NH₂ |

TABLE 1-continued

A—X—Q—(CH₂)n-[benzamide core with R1, R2, R3]

| Compound No. | A | X | Q | n | R1 | R2 | R3 |
|---|---|---|---|---|---|---|---|
| 181 | 4-pyridyl | —CH₂— | —O—C(O)—NH— | 1 | H | H | NH₂ |
| 182 | 4-pyridyl | —(CH₂)₂— | —O—C(O)—NH— | 1 | H | H | NH₂ |
| 183 | 4-pyridyl | Direct bond | —C(O)—NH— | 1 | H | H | NH₂ |
| 184 | 4-pyridyl | —CH₂— | —C(O)—NH— | 0 | H | H | NH₂ |
| 185 | 4-pyridyl | —CH₂— | —NH—C(O)— | 0 | H | H | NH₂ |
| 186 | 4-pyridyl | —CH₂— | —NH—C(O)—O— | 1 | H | H | NH₂ |
| 187 | 2-methyl-4-pyridyl | —CH₂— | —C(O)—NH— | 0 | H | H | NH₂ |
| 188 | 2-methyl-4-pyridyl | Direct bond | —C(O)—NH— | 1 | H | H | NH₂ |
| 189 | 2-methyl-4-pyridyl | —CH₂— | —O—C(O)—NH— | 1 | H | H | NH₂ |
| 190 | 2-chloro-4-pyridyl | —CH₂— | —O—C(O)—NH— | 1 | H | H | NH₂ |
| 191 | pyrazinyl | Direct bond | —C(O)—NH— | 1 | H | H | NH₂ |

TABLE 1-continued

A—X—Q—(CH$_2$)$_n$— ... —C(O)NH— ... (R1, R2, R3 substituted benzanilide)

| Compound No. | A | X | Q | n | R1 | R2 | R3 |
|---|---|---|---|---|---|---|---|
| 192 | pyrazin-2-yl | —CH$_2$— | —O—C(O)—NH— | 1 | H | H | NH$_2$ |
| 193 | pyrazin-2-yl | —CH$_2$—O—CH$_2$— | —C(O)—NH— | 1 | H | H | NH$_2$ |
| 194 | pyrazin-2-yl | —CH$_2$—O—CH$_2$— | —C(O)—NH— | 0 | H | H | NH$_2$ |
| 195 | pyrimidin-2-yl | Direct bond | —C(O)—NH— | 1 | H | H | NH$_2$ |
| 196 | pyrimidin-2-yl | —CH$_2$— | —O—C(O)—NH— | 1 | H | H | NH$_2$ |
| 197 | pyridazin-3-yl | Direct bond | —C(O)—NH— | 1 | H | H | NH$_2$ |
| 198 | pyridazin-3-yl | —CH$_2$— | —O—C(O)—NH— | 1 | H | H | NH$_2$ |
| 199 | pyridazin-3-yl | —CH$_2$—O—CH$_2$— | —C(O)—NH— | 1 | H | H | NH$_2$ |
| 200 | pyridazin-3-yl | —CH$_2$—O—CH$_2$— | —C(O)—NH— | 0 | H | H | NH$_2$ |
| 201 | thien-2-yl | Direct bond | —C(O)—NH— | 1 | H | H | NH$_2$ |
| 202 | thien-2-yl | —CH$_2$— | —O—C(O)—NH— | 1 | H | H | NH$_2$ |
| 203 | thien-3-yl | —(CH$_2$)$_2$— | —O—C(O)—NH— | 1 | H | H | NH$_2$ |

TABLE 1-continued

A—X—Q—(CH₂)n— [benzamide core with R1, R2, R3 substituents]

| Compound No. | A | X | Q | n | R1 | R2 | R3 |
|---|---|---|---|---|---|---|---|
| 204 | 3-thienyl | —CH₂—O—CH₂— | —C(O)—NH— | 0 | H | H | NH₂ |
| 205 | 2-furyl | Direct bond | —C(O)—NH— | 1 | H | H | NH₂ |
| 206 | 2-furyl | —CH₂— | —O—C(O)—NH— | 1 | H | H | NH₂ |
| 207 | 2-furyl | —CH₂—O—CH₂— | —C(O)—NH— | 1 | H | H | NH₂ |
| 208 | 2-furyl | —CH₂—O—CH₂— | —C(O)—NH— | 0 | H | H | NH₂ |
| 209 | 2-pyrrolyl (NH) | Direct bond | —C(O)—NH— | 1 | H | H | NH₂ |
| 210 | 1-methyl-2-pyrrolyl | Direct bond | —C(O)—NH— | 1 | H | H | NH₂ |
| 211 | 3-phenyl-5-isoxazolyl | —CH₂— | —O—C(O)—NH— | 1 | H | H | NH₂ |
| 212 | 5-isoxazolyl | Direct bond | —C(O)—NH— | 1 | H | H | NH₂ |
| 213 | 3-methyl-5-isothiazolyl | Direct bond | —C(O)—NH— | 1 | H | H | NH₂ |
| 214 | 5-imidazolyl (NH) | Direct bond | —C(O)—NH— | 1 | H | H | NH₂ |
| 215 | 1-imidazolyl | —(CH₂)₃— | —NH—C(O)—O— | 1 | H | H | NH₂ |

TABLE 1-continued

| Compound No. | A | X | Q | n | R1 | R2 | R3 |
|---|---|---|---|---|---|---|---|
| 216 | 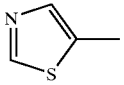 5-thiazolyl | —CH₂— | 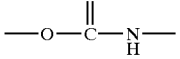 —O—C(=O)—NH— | 1 | H | H | NH₂ |
| 217 | 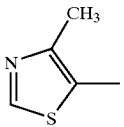 4,5-dimethylthiazolyl | —(CH₂)₂— |  —O—C(=O)—NH— | 1 | H | H | NH₂ |
| 218 | 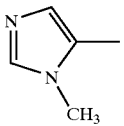 1,5-dimethylimidazolyl | —CH₂— |  —O—C(=O)—NH— | 1 | H | H | NH₂ |
| 219 | 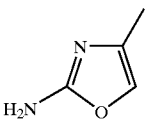 2-amino-4-methyloxazolyl | —CH₂— | 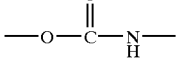 —O—C(=O)—NH— | 1 | H | H | NH₂ |
| 220 | 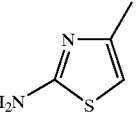 2-amino-4-methylthiazolyl | —CH₂— | 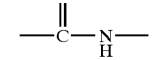 —C(=O)—NH— | 1 | H | H | NH₂ |
| 221 | 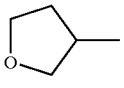 tetrahydrofuranyl | —CH₂— | 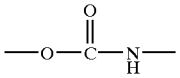 —O—C(=O)—NH— | 1 | H | H | NH₂ |
| 222 | 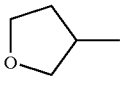 tetrahydrofuranyl | —CH₂—O—CH₂— | 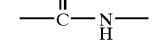 —C(=O)—NH— | 1 | H | H | NH₂ |
| 223 | 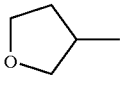 tetrahydrofuranyl | —CH₂—O—CH₂— | 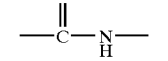 —C(=O)—NH— | 1 | H | H | NH₂ |
| 224 | 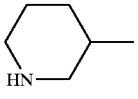 piperidinyl | Direct bond | 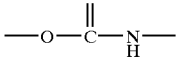 —O—C(=O)—NH— | 1 | H | H | NH₂ |
| 225 | 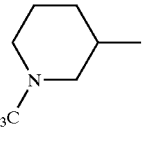 N-methylpiperidinyl | —CH₂— | 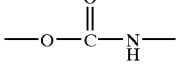 —O—C(=O)—NH— | 1 | H | H | NH₂ |
| 226 | 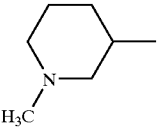 N-methylpiperidinyl | —CH₂—O—CH₂— |  —C(=O)—NH— | 1 | H | H | NH₂ |

TABLE 1-continued

A—X—Q—(CH₂)n— [benzamide core with R1, R2, R3 substituents]

| Compound No. | A | X | Q | n | R1 | R2 | R3 |
|---|---|---|---|---|---|---|---|
| 227 | 4-methylpiperazin-1-yl (H₃C—N⟨piperazine⟩N—) | —(CH₂)₃— | —O—C(=O)—NH— | 1 | H | H | NH₂ |
| 228 | 3-methylquinuclidinyl | Direct bond | —O—C(=O)—NH— | 1 | H | H | NH₂ |
| 229 | 3-methylquinuclidinyl | —CH₂— | —O—C(=O)—NH— | 1 | H | H | NH₂ |
| 230 | 3-methylquinuclidinyl | CH₂—O—CH₂— | —C(=O)—NH— | 1 | H | H | NH₂ |
| 231 | quinolin-6-yl | Direct bond | —C(=O)—NH— | 1 | H | H | NH₂ |
| 232 | quinolin-6-yl | Direct bond | —C(=O)—NH— | 1 | H | H | NH₂ |
| 233 | benzofuran-2-yl | Direct bond | —C(=O)—NH— | 1 | H | H | NH₂ |
| 234 | furo[2,3-c]pyridin-2-yl | Direct bond | —C(=O)—NH— | 1 | H | H | NH₂ |
| 235 | furo[3,2-c]pyridin-2-yl | Direct bond | —C(=O)—NH— | 1 | H | H | NH₂ |
| 236 | thieno[2,3-c]pyridin-2-yl | Direct bond | —C(=O)—NH— | 1 | H | H | NH₂ |
| 237 | 1H-pyrrolo[2,3-c]pyridin-2-yl | Direct bond | —C(=O)—NH— | 1 | H | H | NH₂ |
| 238 | 6-amino-benzofuran-2-yl | Direct bond | —C(=O)—NH— | 1 | H | H | NH₂ |

TABLE 1-continued

A—X—Q—(CH₂)n— [benzamide core with R1, R2, R3 substituents]

| Compound No. | A | X | Q | n | R1 | R2 | R3 |
|---|---|---|---|---|---|---|---|
| 239 | H₂N-(2-methylbenzothiophen-6-yl) | Direct bond | —C(O)—NH— | 1 | H | H | NH₂ |
| 240 | H₂N-(2-methyl-1H-indol-6-yl) | Direct bond | —C(O)—NH— | 1 | H | H | NH₂ |

TABLE 2

| Compound No. | Structural formula |
|---|---|
| 1 | [phenoxymethyl-oxazolidinone-phenyl-C(O)NH-(2-aminophenyl)] |
| 2 | [(4-aminophenoxy)methyl-oxazolidinone-phenyl-C(O)NH-(2-aminophenyl)] |
| 3 | [benzyloxymethyl-oxazolidinone-phenyl-C(O)NH-(2-aminophenyl)] |
| 4 | [(pyridin-3-yloxy)methyl-oxazolidinone-phenyl-C(O)NH-(2-aminophenyl)] |

TABLE 2-continued

| Compound No. | Structural formula |
| --- | --- |
| 5 | |
| 6 | |
| 7 | |
| 8 | |
| 9 | |
| 10 | |

TABLE 2-continued
| Compound No. | Structural formula |
|---|---|
| 11 | 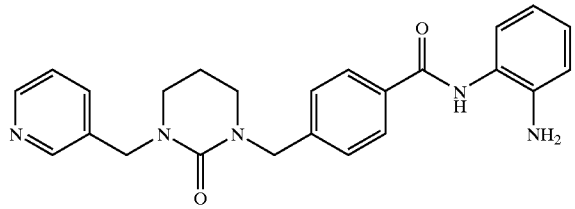 |
| 12 | 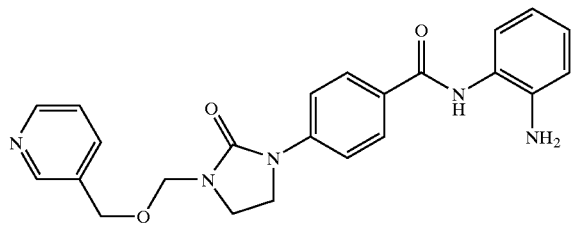 |
| 13 | 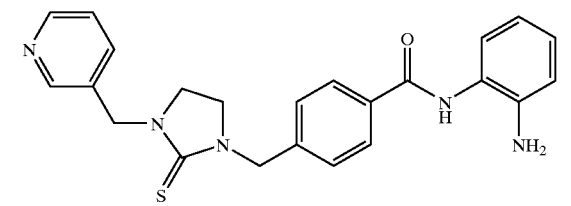 |
| 14 | 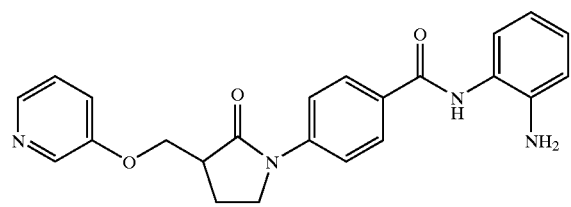 |
| 15 | 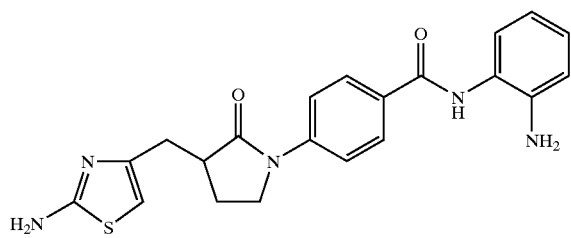 |
| 16 | 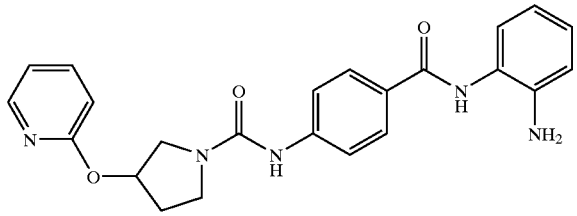 |
| 17 | 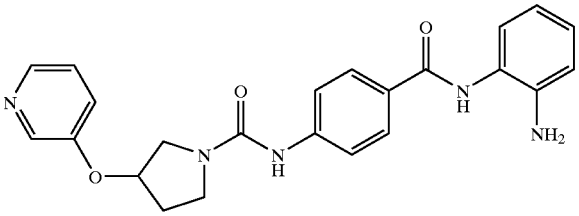 |

TABLE 2-continued

| Compound No. | Structural formula |
|---|---|
| 18 | |
| 19 | |
| 20 | |

TABLE 3

| Compound No. | Structural formula |
|---|---|
| 1 | |
| 2 | |
| 3 | |

TABLE 3-continued

| Compound No. | Structural formula |
|---|---|
| 4 | |
| 5 | |
| 6 | |
| 7 | |
| 8 | |
| 9 | |
| 10 | |
| 11 | |

TABLE 3-continued

| Compound No. | Structural formula |
| --- | --- |
| 12 | |
| 13 | |
| 14 | |
| 15 | |
| 16 | |

TABLE 4

| Compound No. | Structural formula |
| --- | --- |
| 1 | |

TABLE 4-continued

| Compound No. | Structural formula |
| --- | --- |
| 2 | |
| 3 | |
| 4 | |
| 5 | |
| 6 | |
| 7 | |
| 8 | |

TABLE 4-continued

| Compound No. | Structural formula |
|---|---|
| 9 | |
| 10 | |
| 11 | |
| 12 | |
| 13 | |
| 14 | |

The compound of this invention may be prepared as described below.

(a) A compound represented by formula (14);

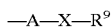
(14)

wherein A and X are as defined above; $R^9$ is —C(=G)OH (G is an oxygen or sulfur atom) or —NH$_2$;

is condensed with a compound represented by formula (15);

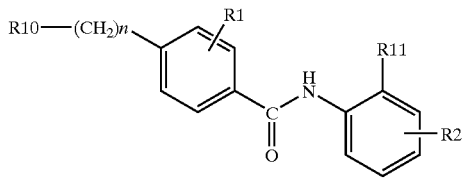
(15)

wherein $R^1$, $R^2$ and n are as defined above; $R^{10}$ is —NH$_2$ when $R^9$ is —C(=G)OH (G is as defined above) and —C(=G)OH (G is as defined above) when $R^9$ is —NH$_2$; $R^{11}$ is an amino group protected with a protective group used in a common peptide-forming reaction, e.g., tert-butoxycarbonyl or a hydroxyl group protected with a protecting group commonly used in a peptide-forming reaction, including benzyl.

(b) A compound represented by formula (16)

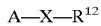
(16)

wherein A and X are as defined above; and $R^{12}$ is —OH or —NH$_2$;

is condensed with a compound represented by formula (17);

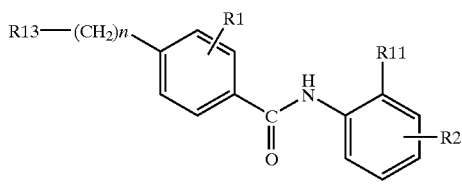
(17)

wherein $R^1$, $R^2$, $R^{11}$ and n are as defined above; $R^{13}$ is —OH or —NH$_2$;

using an agent such as N,N'-carbonyldiimidazole, N,N'-thiocarbonyldiimidazole, phosgene or thiophosgene, to give a compound represented by formula (18);

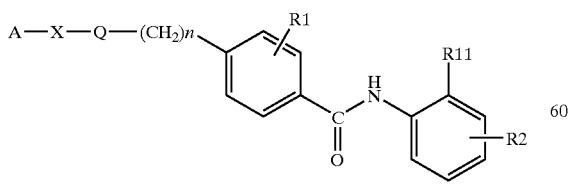
(18)

wherein A, X, Q, n, $R^1$, $R^2$ and $R^{11}$ are as defined above, whose protecting group is then removed to give the compound of this invention.

(c) A compound represented by formula (14) is condensed with a compound represented by formula (19);

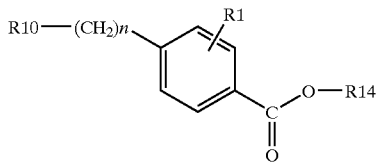
(19)

wherein $R^1$, $R^{10}$ and n are as defined above; $R^{14}$ is a methyl, ethyl or tert-butyl group.

(d) A compound represented by formula (16) is condensed with a compound represented by formula (20);

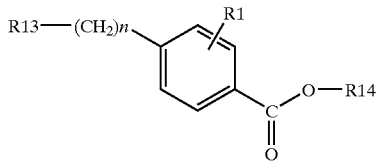
(20)

wherein $R^1$, $R^{13}$, $R^{14}$ and n are as defined above; using an agent such as N,N'-carbonyldiimidazole, N,N'-thiocarbonyldiimidazole, phosgene or thiophosgene to give a compound represented by formula (21);

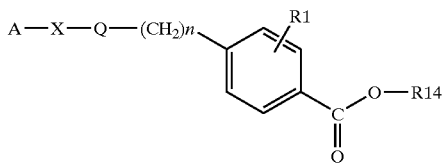
(21)

wherein A, X, Q, n, $R^1$ and $R^{14}$ are as defined above; which is then hydrolyzed to give a compound represented by formula (22);

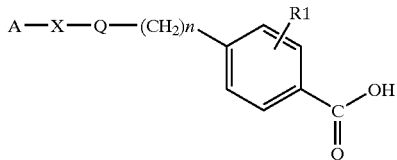
(22)

wherein A, X, Q, n and $R^1$ are as defined above. The product is condensed with a compound represented by formula (23);

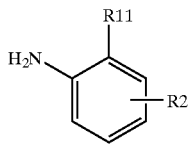
(23)

wherein $R^2$ and $R^{11}$ are as defined above; to give a compound represented by formula (18) whose protecting group is then removed to give the compound of this invention.

(e) A compound represented with formula (22) is condensed with a compound represented by formula (24);

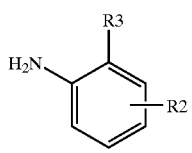

(24)

wherein R² and R³ are as defined above; to give the compound of this invention.

Preparation procedures for typical intermediates are shown below.

A compound represented by formula (15) may be prepared by introducing an appropriate protecting group to a benzoic acid derivative represented by formula (25);

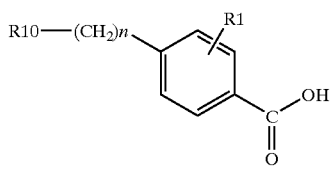

(25)

wherein $R^1$, $R^{10}$ and n are as defined above; condensing the product with a compound represented by formula (23), and removing the protecting group of the condensation product.

A compound represented by formula (17) may be prepared by introducing an appropriate protecting group to a benzoic acid derivative represented by formula (26);

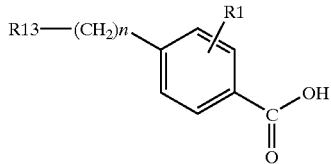

(26)

wherein $R^1$, $R^{13}$ and n are as defined above; condensing the product with a compound represented by formula (23), and removing the protecting group of the condensation product.

A compound represented by formula (23) may be prepared by introducing a protecting group to a compound represented by formula (24).

Next, reactions used for preparation of the compound of this invention will be described.

The condensation reaction in (a) may be an amide-bond forming reaction for a usual peptide using, for example, an activated ester, a mixed acid anhydride or an acid halide. For example, a carboxylic acid, i.e., a compound represented by formula (14) wherein $R^9$ is —C(=G)OH (G is as defined above) or a compound represented by formula (15) wherein $R^{10}$ is —C(=G)OH (G is as defined above), may be condensed with a phenol derivative such as 2,4,5-trichlorophenol, pentachlorophenol and 4-nitrophenol, or an N-hydroxy compound such as N-hydoxysuccinimide and N-hydroxybenzotriazole, in the presence of dicyclohexylcarbodiimide, to be converted into an activated ester, which is then condensed with an amine represented by formula (14) wherein $R^9$ is —NH₂ or by formula (15) wherein $R^{10}$ is —NH₂, to give the desired product.

Alternatively, a carboxylic acid represented by formula (14) wherein $R^9$ is —C(=G)OH (G is as defined above) or by formula (15) wherein $R^{10}$ is —C(=G)OH (G is as defined above), may be reacted with, for example, oxalyl chloride, thionyl chloride or phosphorus oxychloride to be converted into an acid chloride, which is then condensed with an amine represented by formula (14) wherein $R^9$ is —NH₂ or by formula (15) wherein $R^{10}$ is —NH₂, to give the desired product.

Furthermore, a carboxylic acid represented by formula (14) wherein $R^9$ is —C(=G)OH (G is as defined above) or by formula (15) wherein $R^{10}$ is —C(=G)OH (G is as defined above), may be reacted with, for example, isobutyl chlorocarbonate or methanesulfonyl chloride to be converted into a mixed acid anhydride, which is then condensed with an amine represented by formula (14) wherein $R^9$ is —NH₂ or by formula (15) wherein $R^{10}$ is —NH₂, to give the desired product.

The above condensation reaction may be conducted solely using a peptide condensing agent such as dicyclohexylcarbodiimide, N,N'-carbonyldiimidazole, diphenyl phosphoric azide, diethylphosphorylcyanide, 2-chloro-1,3-dimethylimidazolonium chloride, etc.

The reaction may be usually conducted at –20 to +50° C. for 0.5 to 48 hours. Solvents which may be used include aromatic hydrocarbons such as benzene, toluene and the like; ethers such as tetrahydrofuran, dioxane, diethyl ether and the like; halogenated hydrocarbons such as dichloromethane, chloroform and the like; N,N-dimethylformamide; alcohols such as methanol, ethanol and the like; and a mixture thereof. If necessary, an organic base such as triethylamine and pyridine may be added.

The condensation reaction in (b) may be conducted by activating a compound represented by either formula (16) or (17) with, for example, phosgene, thiophosgene, N,N'-carbonyldiimidazole, N,N'-thiocarbonyldiimidazole or the like and then reacting the activated product with the other compound. The reaction may be usually conducted at –20 to +50° C. for 0.5 to 48 hours. Solvents which may be used include aromatic hydrocarbons such as benzene, toluene and the like; ethers such as tetrahydrofuran, dioxane, diethyl ether and the like; halogenated hydrocarbons such as dichloromethane, chloroform and the like; N,N-dimethylformamide; and a mixture thereof. If necessary, an organic base such as triethylamine, pyridine and the like may be added.

The condensation reaction in (c) maybe conducted as the condensation in (a).

The condensation reaction in (d) may be conducted as the condensation in (b).

The protecting group of the compound represented by formula (17) may be removed under the conditions used in a common peptide-forming reaction. For example, when $R^{11}$ in formula (18) is the amino group protected with tert-butoxycarbonyl, it may be deprotected by treatment with an acid such as hydrochloric acid, trifluoroacetic acid or the like.

A salt of a compound represented by formula (1) or (13) maybe formed during preparation of the compound, but is usually formed by treating the compound with a pharmaceutically acceptable acid. Such an acid includes inorganic acids such as hydrochloric acid, hydrobromic acid, sulfuric acid, phosphoric acid and the like; and organic acids such as acetic acid, tartaric acid, fumaric acid, maleic acid, citric acid, benzoic acid, trifluroacetic acid, p-toluenesulfonic acid and the like. These salts may be also used as an active ingredient in this invention, as the free base, the compound represented by formula (1) or (13).

A compound represented by formula (1) or (13) may be purified or isolated by a usual separation method such as extraction, recrystallization, column chromatography and the like.

The novel benzamide or anilide derivative of this invention has differentiation-inducing effect and thus is useful as a therapeutic and/or improving agent to a variety of diseases such as malignant tumors, autoimmune diseases, dermatologic diseases and parasitism.

As used herein, a "malignant tumor" includes hematologic malignancy such as acute leukemia, malignant lymphoma, multiple myeloma and macroglobulinemia as well as solid tumors such as colon cancer, cerebral tumor, head and neck tumor, breast carcinoma, pulmonary cancer, esophageal cancer, gastric cancer, hepatic cancer, gallbladder cancer, bile duct cancer, pancreatic cancer, nesidioblastoma, renal cell carcinoma, adrenocortical cancer, urinary bladder carcinoma, prostatic cancer, testicular tumor, ovarian carcinoma, uterine cancer, chorionic carcinoma, thyroid cancer, malignant carcinoid tumor, skin cancer, malignant melanoma, osteogenic sarcoma, soft tissue sarcoma, neuroblastoma, Wilms tumor and retinoblastoma.

An autoimmune disease includes rheumatism, diabetes, systemic lupus erythematodes, human autoimmune lymphocytotic lymphadenopathy, immunoblastic lymphadenopathy, Crohn disease and ulcerative colitis.

A dermatologic disease includes psoriasis, acne, eczema and atopic dermatitis.

Parasitism includes diseases such as malaria caused through vermination.

Indications for the compound of this invention are not limited to these specific examples.

The active ingredient of this invention useful as a drug may be used in the form of a general pharmaceutical composition. The pharmaceutical composition may be prepared with generally used diluents or excipients such as filler, extender, binder, moisturizing agent, disintegrator, surfactant and lubricant. The pharmaceutical composition may have a variety of dosage forms depending on its therapeutic purpose; typically tablet, pill, powder, solution, suspension, emulsion, granule, capsule, injection (e.g., solution, suspension) and suppository.

For preparing tablets, a variety of carriers well-known in the art may be used. Such a carrier includes excipients such as lactose, glucose, starch, calcium carbonate, kaoline, crystalline cellulose and silicic acid; binders such as water, ethanol, propanol, simple syrup, glucose solution, starch solution, gelatin solution, carboxymethyl cellulose, shellac, methyl cellulose and polyvinyl pyrrolidone; disintegrators such as dried starch, sodium alginate, powdered agar, calcium carmelose, starch and lactose; disintegration retarders such as sucrose, cocoa butter and hydrogenated oil; absorption promoters such as quaternary ammonium base and sodium lauryl sulfate; moisturizing agents such as glycerin and starch; adsorbents such as starch, lactose, kaoline, bentonite, colloidal silicic acid; and glidants such as talc, stearates and polyethylene glycol. The tablet may be, if necessary, one coated with a common coating; for example, sugar-coated tablet, gelatin-coated tablet, enteric coated tablet, film-coated tablet, double-layer tablet and multilayer tablet.

In forming pills, a variety of carriers well-known in the art may be used. Such a carrier includes excipients such as crystalline cellulose, lactose, starch, hydrogenated vegetable oil, kaoline and talc; binders such as powdered acacia, powdered tragacanth gum and gelatin; disintegrators such as calcium carmelose and agar.

Capsule may be prepared by blending an active ingredient with a variety of the above carriers as usual and filling the resulting blend into, for example, a hard or soft gelatin capsule or the like.

For preparing injection, solution, emulsion and suspension are sterilized and preferably isotonic with blood. It may be prepared using diluents commonly used in the art; for example, water, ethanol, macrogol, propylene glycol, ethoxylated isostearyl alcohol, polyoxyisostearyl alcohol and polyoxyethylene sorbitan fatty acid esters. The pharmaceutical preparation may contain sodium chloride necessary to prepare an isotonic solution, glucose or glycerin, as well as usual solubilizers, buffers and soothing agents.

Suppository may be formed using a variety of well-known carriers; for example, semi-synthetic glyceride, cocoa butter, higher alcohols, higher alcohol esters and polyethylene glycol.

Furthermore, the pharmaceutical composition may contain coloring agents, preservatives, perfumes, flavors, sweeteners and/or other drugs.

The amount of the active ingredient in the pharmaceutical composition of this invention may be, as appropriate, selected from a wide range with no limitations, and is generally about 1 to 70% by weight in the composition, preferably about 5 to 50% by weight.

An administration route of the pharmaceutical composition is not limited, and selected depending on patient's age, sex, severity of disease and other conditions. For example, tablet, pill, solution, suspension, emulsion, granule and capsule may be orally administered; injection may be intravenously administered solely or in combination with a common infusion fluid such as glucose, amino acids and the like, or if necessary, intramuscularly, subcutaneously or intraperitoneally as a sole preparation. Suppository may be intrarectally administered.

Dose of the pharmaceutical preparation of this invention may be selected, depending on their dosage form, patient's age, sex and severity of disease, and other conditions, as appropriate, but the amount of the active ingredient may be generally about 0.0001 to 100 mg/kg a day. It is recommended that a unit dosage form may contain about 0.001 to 1000 mg of the active ingredient.

The compound represented by formula (1) or (13) of this invention or a salt thereof exhibits no or a mall toxicity which is acceptable as the anticancer agent at the dose showing pharmacological effects.

EXAMPLES

This invention will be specifically illustrated with, but is not limited to, the following examples, where the numbers in parentheses indicate those of the compounds shown in the above detailed description.

Example 1

Preparation of N-(2-Aminophenyl)-4-(N-benzoylaminomethyl)benzamide Hydrochloride (Table 1: Hydrochloride of Compound 1)

(1-1) To a suspension of 21.16 g of 4-aminomethylbenzoic acid (140 mmol) in 450 mL of dichloromethane was added 42 mL of triethylamine (300 mmol). Under ice-cooling, 60.4 g of trifluoroacetic anhydride (287 mmol) in 50 mL of dichloromethane were added dropwise, maintaining the inner temperature at 3 to 8° C., and then the mixture was stirred four 3 hours. The reaction mixture was poured into a saturated aqueous sodium bicarbonate solution, and was acidified with 10% hydrochloric acid. The gel precipitate was collected by filtration and dried to give 30.4 g of 4-(N-trifluoroacetylaminomethyl)benzoic acid (Yield: 87.8%) as an opalescent solid.

$^1$H NMR (270 MHz, DMSO-$d_6$) δ ppm: 4.47 (2H, d, J=5.8 Hz), 7.39 (2H, d, J=8.1 Hz), 7.93 (2H, d, J=8.1 Hz), 10.08 (1H, t, J=5.8 Hz), 12.95 (1H, br.s.).

(1-2) To a solution of 108 g of o-phenylenediamine (1.0 mol) in 1000 mL of dioxane was added 500 mL of 1N sodium hydroxide aq., and then 218 g of tert-butyldicarbonate (1.1 mol) in 500 mL of dioxane under ice-cooling. After stirring for 6 hours at room temperature, the mixture was left overnight. The mixture was concentrated to ½ volume by evaporation, and extracted with ethyl acetate. The organic layer was washed with saturated brine, dried and evaporated. The residue was purified by column chromatography (eluent: chloroform) to give a solid, which was then washed with diethyl ether to give 68.4 g of N-tert-butoxycarbonyl-o-phenylenediamine (Yield: 32.8%) as a white solid.

$^1$H NMR (270 MHz, CDCl$_3$) δ ppm: 1.51 (9H, s), 3.75 (2H, s), 6.26 (1H, s), 6.77 (1H, d, J=8.1 Hz), 6.79 (1H, dd, J=7.3, 8.1 Hz), 7.00 (1H, dd, J=7.3, 8.1 Hz), 7.27 (1H, d, J=8.1 Hz).

(1-3) To a suspension of 30 g of the compound from the process (1-1) (121 mmol) in 200 mL of dichloromethane were slowly added dropwise 21 g of oxalyl chloride (165 mmol) with intermittently adding DMF (0.1 mL per 2 mL addition), maintaining the inner temperature within 10 to 15° C. by ice-cooling. After completion of the addition, the mixture was stirred until bubble generation ceased, and then at 40° C. for an additional hour. After evaporation, excess oxalyl chloride was azeotropically removed with toluene, and then the residue was redissolved in 100 mL of dichloroethane. The prepared acid chloride solution was added dropwise to a solution of 22.88 g of the compound from the process (1-2) (110 mmol) in 100 mL of dichloromethane and 200 mL of pyridine, maintaining the inner temperature within 7 to 9° C. by ice-cooling.

After addition, the mixture was warmed to room temperature, and was left overnight. After adding saturated sodium bicarbonate aq. to the reaction mixture, the resulting mixture was extracted with chloroform, and the organic layer was washed with saturated brine, dried and evaporated. To the residue was added methanol-diisopropyl ether, and the precipitated solid was collected by filtration and dried to give 28.1 g of N-[2-(N-tert-butoxycarbonyl)aminophenyl]-4-(N-trifluoroacetylaminomethyl)benzamide (Yield: 58%) as a light yellow solid.

$^1$H NMR (270 MHz, DMSO-d$_6$) δ ppm: 1.44 (9H, s), 4.48 (2H, d, J=5.9 Hz), 7.12–7.23 (2H, m), 7.44 (2H, d, J=8.1 Hz), 7.54 (2H, d, J=8.1 Hz), 7.94 (2H, d, J=8.1 Hz), 8.68 (1H, br.s), 9.83 (1H, s), 10.10 (1H, br.t, J=5.9 Hz).

(1-4) To a suspension of 13.12 g of the compound from the process (1-3) (30 mmol) in 120 mL of methanol and 180 mL of water were added 4.70 g of potassium carbonate (34.0 mmol), and the mixture was heated with stirring at 70° C. for 4 hours. It was extracted with chloroform, and the organic layer was washed with saturated brine, dried, evaporated and dried to give 10.3 g of 4-aminomethyl-N-[2-(N-tert-butoxycarbonyl)aminophenyl]benzamide (Yield: quantitative) as a light yellow amorphous solid.

$^1$H NMR (270 MHz, DMSO-d$_6$) δ ppm: 3.80 (2H, s), 7.13–7.23 (2H, m), 7.48–7.58 (4H, m), 7.90 (2H, d, J=8.1 Hz), 8.69 (1H, br.s), 9.77 (1H, br.s).

(1-5) To a solution of 0.11 g of the compound from the process (1-4) (0.44 mmol) in 5 mL of pyridine was added 0.08 g of benzoyl chloride (0.53 mmol), and the mixture was gradually warmed to room temperature and then stirred for 8 hours. Saturated sodium bicarbonate aq. was added, and then the mixture was extracted with ethyl acetate. The organic layer was washed with saturated brine, dried and evaporated. The residue was washed with diisopropyl ether, and the solid obtained was dried to give 0.14 g of N-[2-(N-tert-butoxycarbonyl)aminophenyl]-4-(N-benzoylaminomethyl)benzamide (Yield: 71.4%) as a white solid.

$^1$H NMR (270 MHz, DMSO-d$_6$) δ ppm: 1.44 (9H, s), 4.56 (2H, d, J=5.9 Hz), 7.11–7.22 (2H, m), 7.46–7.56 (7H, m), 7.90–7.94 (4H, m), 8.67 (1H, s), 9.15 (1H, t, J=5.9 Hz), 9.81 (1H, s).

(1-6) To a solution of 0.10 g of the compound from the process (1-5) (0.224 mmol) in 5 mL of dioxane and 1 mL of methanol was added 5 mL of 4N hydrochloric acid-dioxane, and the mixture was stirred at room temperature for 7 hours. To the residue after evaporation was added diisopropyl ether, and the formed solid was collected by filtration and dried to give 0.08 g of N-(2-aminophenyl)-4-(N-benzoylaminomethyl)benzamide hydrochloride (Yield: 93%) as a light brown solid.

mp: 206–209° C.; $^1$H NMR (270 MHz, DMSO-d$_6$) δ ppm: 4.57 (2H, d, J=5.8 Hz), 7.27–7.38 (4H, m), 7.47–7.59 (5H, m), 7.92 (1H, d, J=8.1 Hz), 8.05 (1H, d, J=8.1 Hz), 9.19 (1H, t, J=5.8 Hz), 10.38 (1H, br.s); IR (KBr, cm$^{-1}$): 3286, 3003 (br.), 1630, 1551, 1492, 1306, 1250, 749, 695.

As described in Example 1, the compounds of Examples 2 to 44 were prepared, each of whose melting point (mp), $^1$H NMR data and/or IR data are described below.

Example 2

N-(2-Aminophenyl)-4-[N-(2-chlorobenzoyl) aminomethyl]benzamide (Table 1: Compound 14)

mp: 201–204° C. (dec.). $^1$H NMR (270 MHz, DMSO-d$_6$) δ ppm: 4.52 (2H, t, J=5.9 Hz), 4.89 (2H, br.s), 6.60 (1H, ddd, J=1.5, 7.3, 8.1 Hz), 6.78 (1H, dd, J=1.5, 8.1 Hz), 6.97 (1H, ddd, J=1.5, 7.3, 8.1 Hz), 7.17 (1H, d, J=8.1 Hz), 7.38–7.54 (6H, m), 7.97 (2H, d, J=8.1 Hz), 9.06 (1H, br.t, J=5.9 Hz), 9.63 (1H, br.s); IR (KBr) cm$^{-1}$: 3268, 1649, 1458, 1304, 748.

Example 3

N-(2-Aminophenyl)-4-[N-(2-nitrobenzoyl) aminomethyl]benzamide Hydrochloride (Table 1: Hydrochloride of Compound 18)

mp: 210–212° C. (dec.); $^1$H NMR (270 MHz, DMSO-d$_6$) ppm: 4.55 (2H, t, J=5.9 Hz) 7.20–7.40 (3H, m), 7.50–7.60 (1H, m), 7.53 (2H, d, J=8.1 Hz), 7.60–7.70 (2H, m), 7.83 (1H, ddd, J=1.5, 8.1, 8.1 Hz), 8.00–8.10 (3H, m), 9.34 (1H, t, J=5.9 Hz) 10.43 (1H, br.s); IR (KBr)cm$^{-1}$: 3283, 2500–3000 (br.), 1648, 1534, 1461, 1362, 1314, 754, 701.

Example 4

N-(2-Aminophenyl)-4-[N-(4-methylbenzoyl) aminomethyl]benzamide Hydrochloride (Table 1: Hydrochloride of Compound 28)

mp: (amorphous). $^1$H NMR (270 MHz, DMSO-d$_6$) ppm: 2.37 (3H, s), 4.56 (2H, d, J=5.0 Hz), 7.20–7.30 (6H, m), 7.47 (4H, d, J=8.8 Hz), 7.82 (2H, d, J=8.8 Hz), 8.03 (2H, d, J=8.8 Hz), 9.09 (1H, t, J=5 Hz), 10.36 (1H, br.s); IR (KBr)cm$^{-1}$: 3269 (br.), 2861 (br.), 1743, 1636, 1534, 1505, 1456, 1308, 1120, 753.

Example 5

N-(2-Aminophenyl)-4-[N-(3-methoxybenzoyl) aminomethyl]benzamide (Table 1: Compound 30)

mp: 182–185° C.; $^1$H NMR (270 MHz, DMSO-d$_6$) δ ppm: 3.81 (3H, s), 4.54 (2H, d, J=5.9 Hz), 4.88 (2H, br.s), 6.60

(1H, dd, J=6.6, 7.3 Hz), 6.78 (1H, d, J=7.3 Hz), 6.97 (1H, dd, J=6.6, 7.3 Hz), 7.11 (1H, dd, J=1.5, 8.1 Hz), 7.16 (1H, d, J=7.3 Hz), 7.35–7.51 (5H, m), 7.94 (2H, d, J=8.1 Hz), 9.12 (1H, br.t, J=5.9 Hz), 9.63 (1H, br.s); IR (KBr)cm$^{-1}$: 3301, 1637, 1524, 1489, 1457, 1314, 1248, 752.

Example 6

N-(2-Aminophenyl)-4-[N-(4-methoxybenzoyl)aminomethyl]benzamide (Table 1: Compound 31)

mp: 149–151° C.; $^1$H NMR (270 MHz, DMSO-d$_6$) δ ppm: 3.82 (3H, s), 4.53 (2H, d, J=5.9 Hz), 4.88 (2H, s), 6.59 (1H, dd, J=7.3, 7.3 Hz), 6.77 (1H, d, J=8.1 Hz), 6.94–7.00 (1H, m), 7.02 (2H, d, J=8.8 Hz), 7.16 (1H, d, J=8.1 Hz), 7.43 (2H, d, J=8.1 Hz), 7.89 (2H, d, J=8.8 Hz), 7.94 (2H, d, J=8.1 Hz), 8.98 (1H, br.t, J=5.9 Hz), 9.61 (1H, br.s); IR (KBr)cm$^{-1}$: 3297, 1630, 1527, 1505, 1457, 1256, 1177, 1024, 843, 749.

Example 7

N-(2-Aminophenyl)-4-[N-(3,4,5-trimethoxybenzoyl)aminomethyl]benzamide (Table 1: Compound 33)

mp: 208–210° C. (dec.); $^1$H NMR (270 MHz, DMSO-d$_6$) δ ppm: 3.71 (3H, s), 3.83 (6H, s), 4.55 (2H, d, J=5.9 Hz), 4.88 (2H, br.s), 6.60 (1H, dd, J=7.3, 8.1 Hz), 6.78 (1H, d, J=8.1 Hz), 6.97 (1H, dd, J=6.6, 8.1 Hz), 7.16 (1H, d, J=8.1 Hz), 7.26 (2H, s), 7.44 (2H, d, J=8.1 Hz), 7.95 (2H, d, J=8.8 Hz), 9.07 (1H, t, J=5.9 Hz), 9.62 (1H, br.s); IR (KBr)cm$^{-1}$: 3267, 1635, 1582, 1457, 1237, 1132, 755.

Example 8

N-(2-Aminophenyl)-4-[N-[4-(N,N-dimethyl)aminobenzoyl]aminomethyl]benzamide (Table 1: Compound 36)

mp: 216–219° C. (dec.); $^1$H NMR (270 MHz, DMSO-d$_6$) δ ppm: 2.98 (6H, s), 4.51 (2H, d, J=5.9 Hz), 4.88 (2H, br.s), 6.60 (1H, dd, J=8.1, 8.1 Hz), 6.71 (2H, d, J=8.8 Hz), 6.97 (1H, dd, J=7.3, 8.1 Hz), 7.16 (1H, d, J=7.3 Hz), 7.41 (2H, d, J=8.1 Hz), 7.78 (2H, d, J=8.8 Hz), 7.93 (2H, d, J=8.1 Hz), 8.77 (1H, t, J=5.9 Hz), 9.63 (1H, br.s). IR (KBr)cm$^{-1}$: 3301, 1632, 1519, 1457, 1298, 754.

Example 9

N-(2-Aminophenyl)-4-[N-(4-trifluoromethylbenzoyl)aminomethyl]benzamide (Table 1: Compound 42)

mp: 243–246° C. $^1$H NMR (270 MHz, DMSO-d$_6$) δ ppm: 4.58 (2H, d, J=5.9 Hz), 4.88 (2H, br.s), 6.59 (1H, dd, J=6.6, 7.3 Hz), 6.77 (1H, d, J=8.1 Hz), 6.94 (1H, dd, J=5.9, 6.6 Hz), 7.16 (1H, d, J=8.1 Hz), 7.45 (2H, d, J=8.1 Hz), 7.88 (2H, d, J=8.8 Hz), 7.95 (2H, d, J=8.1 Hz), 8.11 (2H, d, J=8.1 Hz), 9.38 (1H, t, J=5.9 Hz), 9.64 (1H, br.s); IR (KBr)cm$^{-1}$: 3301, 1640, 1549, 1523, 1458, 1334, 1162, 1120, 1070, 856, 750.

Example 10

N-(2-Aminophenyl)-4-[N-(4-carboxybenzoyl)aminomethyl]benzamide Hydrochloride (Table 1: Hydrochloride of Compound 45)

mp: (amorophous). $^1$H NMR (270 MHz, DMSO-d$_6$) δ ppm: 4.58 (2H, d, J=5.9 Hz), 7.29–7.37 (3H, m), 7.49 (3H, d, J=8.1 Hz), 8.02–8.06 (6H, m), 9.36 (1H, t, J=5.9 Hz), 10.4 (1H, br.s); IR (KBr)cm$^{-1}$: 3432 (br.), 1718, 1637, 1542, 1499, 1303 (br.), 1116, 1018, 757.

Example 11

N-(2-Aminophenyl)-4-[N-(4-methoxycarboxybenzoyl)aminomethyl]benzamide (Table 1: Compound 46)

mp: 204–209° C. (dec.); $^1$H NMR (270 MHz, DMSO-d$_6$) δ ppm: 3.89 (3H, s), 4.57 (2H, d, J=5.9 Hz), 4.88 (2H, br.s), 6.60 (1H, dd, J=6.6, 7.3 Hz), 6.78 (2H, d, J=7.3 Hz), 6.97 (1H, ddd, J=1.5, 6.6, 7.3 Hz), 7.16 (1H, d, J=7.3 Hz), 7.45 (2H, d, J=8.1 Hz), 7.95 (2H, d, J=8.1 Hz), 8.03 (2H, d, J=8.8 Hz), 8.07 (2H, d, J=8.8 Hz), 9.35 (1H, t, J=5.9 Hz), 9.64 (1H, br.s); IR (KBr)cm$^-$: 3287 (br.), 1721, 1634, 1281, 1113, 750, 703.

Example 12

N-(2-Aminophenyl)-4-(N-picolinoylaminomethyl)benzamide (Table 1: Compound 173)

mp: 173–178° C. (dec.); $^1$H NMR (270 MHz, DMSO-d$_6$) δ ppm: 4.57 (2H, d, J=6.6 Hz), 4.88 (2H, br.s), 6.59 (1H, dd, J=7.3, 8.1 Hz), 6.77 (1H, d, J=8.1 Hz), 6.96 (1H, dd, J=7.3, 8.1 Hz), 7.16 (1H, d, J=7.3 Hz), 7.44 (2H, d, J=8.1 Hz), 7.60–7.65 (1H, m), 7.93 (2H, d, J=8.1 Hz), 7.98–8.08 (2H, m), 8.67 (1H, d, J=4.4 Hz), 9.45 (1H, t, J=6.6 Hz), 9.61 (1H, br s); IR (KBr)cm$^{-1}$: 3330, 1656, 1634, 1523, 1456, 1294, 752.

Example 13

N-(2-Aminophenyl)-4-(N-(6-methylpicolinoyl)aminomethyl)benzamide (Table 1: Compound 178)

mp: 172–173° C.; $^1$H NMR (270 MHz, DMSO-d$_6$) δ ppm: 2.51 (3H, s), 4.57 (2H, d, J=6.6 Hz), 5.0 (2H, br.s), 6.61 (1H, dd, J=7.3, 8.1 Hz), 6.79 (1H, d, J=7.3 Hz), 6.98 (1H, dd, J=7.3, 8.1 Hz), 7.17 (1H, d, J=7.3 Hz), 7.44 (2H, d, J=8.1 Hz), 7.43–7.49 (1H, m), 7.84–7.90 (2H, m), 7.94 (2H, d, J=8.1 Hz), 9.27 (1H, t, J=5.9 Hz), 9.64 (1H, br.s); IR (KBr)cm$^{-1}$: 3331, 1675, 1634, 1594, 1523, 1454, 1307, 1292, 750.

Example 14

N-(2-Aminophenyl)-4-(N-nicotinoylaminomethyl)benzamide (Table 1: Compound 71)

mp: 193–196° C.; $^1$H NMR (270 MHz, DMSO-d$_6$) δ ppm: 4.58 (2H, d), 4.88 (2H, br.s), 6.60 (1H, t), 6.78 (1H, d), 6.97 (1H, t), 7.16 (1H, d), 7.46 (2H, d), 7.53 (1H, dd), 7.95 (2H, d), 8.24 (1H, ddd), 8.73 (1H, dd), 9.07 (1H, d), 9.32 (1H, br.t), 9.63 (1H, br.s) IR (KBr)cm$^{-1}$: 3301, 1639, 1522, 1457, 1314, 749, 705.

Example 15

N-(2-Aminophenyl)-4-[N-(2-methylnicotinoyl)aminomethyl]benzamide (Table 1: Compound 141)

mp: 191–194° C. (dec.); $^1$H NMR (270 MHz, DMSO-d$_6$) δ ppm: 2.53 (3H, s), 4.53 (2H, d, J=5.9 Hz), 4.88 (2H, br.s), 6.60 (1H, dd, J=6.6, 8.1 Hz), 6.78 (1H, d, J=7.3 Hz), 6.97 (1H, dd, J=7.3, 8.1 Hz), 7.17 (1H, d, J=7.3 Hz), 7.29 (1H, dd, J=5.1, 8.1 Hz), 7.47 (2H, d, J=8.1 Hz), 7.77 (1H, dd, J=1.5, 8.1 Hz), 7.97 (2H, d, J=8.1 Hz), 8.51 (1H, dd, J=1.5, 5.1 Hz), 9.06 (1H, t, J=5.9 Hz), 9.64 (1H, s); IR (KBr)cm$^{-1}$: 3261, 1642, 1523, 1310, 753.

Example 16

N-(2-Aminophenyl)-4-[N-(6-methylnicotinoyl)aminomethyl]benzamide (Table 1: Compound 143)

mp: 186–190° C. (dec.); $^1$H NMR (270 MHz, DMSO-d$_6$) δ ppm: 2.36 (3H, s), 4.56 (2H, d, J=5.9 Hz), 4.88 (2H, s), 6.60 (1H, dd, J=7.4, 7.8 Hz), 6.78 (1H, d, J=7.8 Hz), 6.97 (1H, dd, J=6.9, 6.9 Hz), 7.16 (1H, d, J=7.4 Hz), 7.37 (1H, d, J=8.3 Hz), 7.45 (2H, d, J=8.3 Hz), 7.95 (2H, d, J=8.3 Hz), 8.13 (1H, dd, J=2.0, 8.3 Hz), 8.96 (1H, s), 9.24 (1H, t, J=5.9 Hz), 9.63 (1H, br.s); IR (KBr)cm$^{-1}$: 3302, 1636, 1602, 1523, 1489, 1457, 1313, 751.

Example 17

N-(2-Aminophenyl)-4-[N-(2-chloronicotinoyl) aminomethyl]benzamide (Table 1: Compound 154)

mp: 176–178° C. (dec.); $^1$H NMR (270 MHz, DMSO-d$_6$) δ ppm: 4.54 (2H, t, J=5.9 Hz), 4.90 (2H, br.s), 6.60 (1H, ddd, J=1.5, 7.3, 7.3 Hz), 6.78 (1H, d, J=8.1 Hz), 6.97 (1H, ddd, J=1.5, 7.3, 7.3 Hz), 7.18 (1H, d, J=8.1 Hz), 7.48–7.54 (3H, m), 7.94–7.99 (3H, m), 8.49 (1H, dd, J=2.1, 5.1 Hz), 9.23 (1H, br.t, J=5.9 Hz), 9.65 (1H, br.s); IR (KBr)cm$^{-1}$: 3264, 1649, 1524, 1400, 1309, 751.

Example 18

N-(2-Aminophenyl)-4-[N-(6-chloronicotinoyl) aminomethyl]benzamide (Table 1: Compound 156)

mp: 205–208° C. (dec.); $^1$H NMR (270 MHz, DMSO-d$_6$) δ ppm: 5.57 (2H, d, J=5.9 Hz), 6.60 (1H, dd, J=7.3, 7.3 Hz), 6.78 (1H, d, J=8.1 Hz), 6.96 (1H, dd, J=7.3, 8.1 Hz), 7.16 (1H, d, J=8.1 Hz), 7.45 (2H, d, J=8.1 Hz), 7.66 (1H, d, J=8.8 Hz), 7.95 (2H, d, J=8.1 Hz), 8.27–8.32 (1H, m), 8.90 (1H, d, J=2.1 Hz), 9.38 (1H, t, J=5.9 Hz), 9.63 (1H, s); IR (KBr)cm$^{-1}$: 3318 (br.), 2929, 1646, 1590, 1525, 1503, 1454, 1108, 745.

Example 19

N-(2-Aminophenyl)-4-(N-isonicotinoylaminomethyl)benzamide (Table 1: Compound 183)

mp: 234–237° C. (dec.); $^1$H NMR (270 MHz, DMSO-d$_6$) δ ppm: 4.57 (2H, t, J=5.9 Hz), 4.88 (2H, br.s), 6.59 (1H, dd, J=6.6, 7.3 Hz), 6.78 (1H, d, J=8.1 Hz), 6.96 (1H, dd, J=7.3, 7.3 Hz), 7.16 (1H, d, J=7.3 Hz), 7.45 (2H, d, J=8.1 Hz), 7.81 (2H, d, J=1.5, 4.4 Hz), 7.95 (2H, d, J=8.1 Hz), 8.75 (2H, d, J=6.6 Hz), 9.41 (1H, t, J=5.9 Hz), 9.62 (1H, br.s); IR (KBr)cm$^{-1}$: 3298, 1646, 1550, 1525, 1457, 1304, 843, 760, 695.

Example 20

N-(2-Aminophenyl)-4-[N-(pyrazin-2-yl) carbonylaminomethyl]benzamide (Table 1: Compound 191)

mp: 207° C. (dec.); $^1$H NMR (270 MHz, DMSO-d$_6$) δ ppm: 4.58 (2H, d, J=5.9 Hz), 4.88 (2H, br.s), 6.59 (1H, dd, J=7.3, 7.3 Hz), 6.77 (1H, d, J=8.1 Hz), 6.94 (1H, ddd, J=1.5, 7.3, 8.1 Hz), 7.15 (1H, d, J=7.3 Hz), 7.45 (2H, d, J=8.1 Hz), 7.93 (2H, d, J=8.1 Hz), 8.77 (1H, d, J=1.5 Hz), 8.90 (1H, d, J=2.1 Hz), 9.21 (1H, s), 9.55–9.61 (2H, m); IR (KBr)cm$^{-1}$: 3368 (br.), 1657, 1524, 1455, 1295, 1023, 751.

Example 21

N-(2-Aminophenyl)-4-[N-(thiophen-2-yl) carbonylaminomethyl]benzamide (Table 1: Compound 201)

mp: 202–205° C. (dec.); $^1$H NMR (270 MHz, DMSO-d$_6$) δ ppm: 4.52 (2H, t, J=5.9 Hz), 4.88 (2H, br.s), 6.60 (1H, dd, J=6.6.7.3 Hz), 6.78 (1H, d, J=8.1 Hz), 6.97 (1H, dd, J=7.3, 8.1 Hz), 7.15–7.18 (2H, m), 7.43 (2H, d, J=8.1 Hz), 7.78 (1H, d, J=4.4), 7.82 (1H, d, J=3.7 Hz), 7.95 (2H, d, J=8.1 Hz), 9.12 (1H, br.t, J=5.9 Hz), 9.62 (1H, br.s); IR (KBr)cm$^{-1}$: 3306, 1633, 1523, 1456, 1297, 750, 716.

Example 22

N-(2-Aminophenyl)-4-[N-(furan-2-yl) carbonylaminomethyl]benzamide (Table 1: Compound 205)

mp: 197° C. (dec.); $^1$H NMR (270 MHz, DMSO-d$_6$) δ ppm: 4.59 (2H, d, J=6.6 Hz), 4.86 (2H, br.s), 6.59 (1H, dd, J=6.6, 6.6 Hz), 6.63 (1H, dd, J=1.5, 3.6 Hz), 6.78 (1H, d, J=8.1 Hz), 6.96 (1H, dd, J=7.3, 6.6 Hz), 7.10–7.20 (2H, m), 7.41 (2H, d, J=8.1 Hz), 7.84 (1H, s), 7.94 (2H, d, J=1 Hz), 9.00 (1H, br.t, J=5.9 Hz), 9.62 (1H, s); IR (KBr)cm$^{-1}$: 3245, 1651, 1573, 1545, 1323, 1241, 745.

Example 23

N-(2-Aminophenyl)-4-[N-(pyrrol-2-yl) carbonylaminomethyl]benzamide (Table 1: Compound 209)

mp: 216–220° C. (dec.); $^1$H NMR (270 MHz, DMSO-d$_6$) δ ppm: 4.50 (2H, d, J=5.9 Hz), 4.88 (2H, br.s), 6.10 (1H, dd, J=2.1, 5.9 Hz), 6.59 (1H, dd, J=7.3, 7.3 Hz), 6.77 (1H, dd, J=1.5, 8.1 Hz), 6.84–6.88 (2H, m), 6.97 (1H, ddd, J=1.5, 7.3, 8.1 Hz), 7.16 (1H, d, J=7.3 Hz), 7.41 (2H, d, J=8.1 Hz), 7.94 (2H, d, J=8.1 Hz), 8.62 (1H, br.t, J=5.9 Hz), 9.62 (1H, br.s); IR (KBr)cm$^{-1}$: 3275, 1655, 1584, 1534, 1458, 1316, 747.

Example 24

N-(2-Aminophenyl)-4-[N-(N'-methyl-1H-pyrrol-2-yl)carbonylaminomethyl]benzamide (Table 1: Compound 210)

mp: 177–179° C. (dec.); $^1$H NMR (270 MHz, DMSO-d$_6$) δ ppm: 3.84 (3H, s), 4.46 (2H, d, J=5.9 Hz), 4.88 (2H, br.s), 6.03 (1H, dd, J=2.1, 4.4 Hz), 6.59 (1H, dd, J=8.1, 8.1 Hz), 6.77 (1H, d, J=8.1 Hz), 6.84–6.97 (2H, m), 7.16 (1H, d, J=7.3 Hz), 7.41 (2H, d, J=8.1 Hz), 7.93 (2H, d, J=8.1 Hz), 8.61 (1H, t, J=5.9 Hz), 9.62 (1H, br.s); IR (KBr)cm$^{-1}$: 3325 (br.), 1630, 1551, 1520, 1507, 1324, 1265, 1154, 740.

Example 25

N-(2-Aminophenyl)-4-[N-(isoxazol-5-yl) carbonylaminomethyl]benzamide (Table 1: Compound 212)

mp: 183–185° C. (dec.); $^1$H NMR (270 MHz. DMSO-d$_6$) δ ppm: 4.53 (2H, d, J=6.6 Hz), 4.89 (2H, br.s), 6.60 (1H, dd, J=7.3, 7.3 Hz), 6.78 (1H, d, J=7.3 Hz), 6.97 (1H, dd, J=7.3, 8.1 Hz), 7.12 (1H, d, J=2.1 Hz), 7.16 (1H, d, J=8.1 Hz), 7.44 (2H, d, J=8.1 Hz), 7.95 (2H, d, J=8.1 Hz), 8.76 (1H, d, J=1.5 Hz), 9.61 (1H, t, J=5.9 Hz), 9.64 (1H, br.s); IR (KBr)cm$^{-1}$: 3278 (br.), 1636, 1576, 1522, 1458, 1220, 749.

Example 26

N-(2-Aminophenyl)-4-[N-(3-methylisothiazol-5-yl) carbonylaminomethyl]benzamide (Table 1: Compound 213)

mp: 168–169° C. $^1$H NMR (270 MHz, DMSO-d$_6$) δ ppm: 2.47 (3H, s), 4.54 (2H, d, J=5.9 Hz), 4.89 (2H, br.s), 6.60

(1H, dd, J=7.3, 7.3 Hz), 6.78 (1H, d, J=7.3 Hz), 6.97 (1H, ddd, J=1.0, 7.3, 8.1 Hz), 7.17 (1H, d, J=7.3 Hz), 7.44 (2H, d, J=8.1 Hz), 7.73 (1H, s), 7.96 (2H, d, J=8.1 Hz), 9.44 (1H, t, J=5.9 Hz), 9.64 (1H, br.s); IR (KBr)cm$^{-1}$: 3310, 1637, 1503, 1294, 751.

Example 27

N-(2-Aminophenyl)-4-[N-(imidazol-4-yl) carbonylaminomethyl]benzamide (Table 1: Compound 214)

mp: (amorphous). $^1$H NMR (270 MHz, DMSO-d$_6$) δ ppm: 4.49 (2H, d, J=6.4 Hz), 4.87 (2H, br.s), 6.59 (1H, dd, J=6.9, 6.9 Hz), 6.77 (1H, d, J=6.9 Hz), 6.96 (1H, dd, J=7.4, 7.4 Hz), 7.16 (1H, d, J=6.9 Hz), 7.41 (2H, d, J=6.9 Hz), 7.64 (1H, br.s), 7.73 (1H, br.s), 7.92 (2H, d, J=6.9 Hz), 8.56 (1H, br.t, J=6.4 Hz), 9.61 (1H, s), 12.5 (1H, br.s); IR (KBr)cm$^{-1}$: 3278 (br.), 1636, 1576, 1522, 1458, 1220, 749.

Example 28

N-(2-Aminophenyl)-4-[N-(3-aminophenyl) acetylaminomethyl]benzamide (Table 1: Compound 23)

mp: 171–176° C.; $^1$H NMR (270 MHz, DMSO-d$_6$) δ ppm: 4.34 (2H, d, J=5.9 Hz), 5.24 (4H, br.s), 6.48–6.63 (4H, m), 6.78–6.81 (1H, m), 6.94–7.00 (2H, m), 7.18 (1H, d, J=8.1 Hz), 7.34 (2H, d, J=8.1 Hz), 7.92 (2H, d, J=8.1 Hz), 8.50 (1H, t, J=5.9 Hz), 9.61 (1H, s).

Example 29

N-(2-Aminophenyl)-4-[N-(pyridin-3-yl) acetylaminomethyl]benzamide (Table 1: Compound 74)

mp: 127° C.; $^1$H NMR (270 MHz, DMSO-d$_6$) δ ppm: 3.84 (2H, s), 4.40 (2H, d, J=5.8 Hz), 7.15–7.29 (3H, m), 7.37 (1H, d, J=6.6 Hz), 7.43 (2H, d, J=8.8 Hz), 7.96 (1H, m), 7.98 (2H, d, J=8.8 Hz), 8.40 (1H, d, J=8.8 Hz), 8.79–8.87 (3H, m), 10.20 (1H, s).

Example 30

N-(2-Aminophenyl)-4-[N-[3-(pyridin-3-yl) propionyl]aminomethyl]benzamide (Table 1: Compound 75)

mp: 183–186° C.; $^1$H NMR (270 MHz, DMSO-d$_6$) δ ppm: 2.51 (2H, t, J=7.3 Hz), 2.88 (2H, d, J=7.3 Hz), 4.31 (2H, d, J=5.9 Hz), 4.89 (2H, br.s), 6.60 (1H, dd, J=7.3, 8.1 Hz), 6.78 (1H, d, J=8.1 Hz), 6.97 (1H, ddd, J=1.5, 7.3, 8.1 Hz), 7.16 (1H, d, J=8.1 Hz), 7.23 (2H, d, J=8.8 Hz), 7.28–7.33 (1H, m), 7.63 (1H, d, J=8.1 Hz), 7.89 (2H, d, J=8.1 Hz), 8.41–8.45 (3H, m), 9.62 (1H, br.s); IR (KBr)cm$^{-1}$: 3407, 3313, 1640, 1552, 1522, 1456, 1309, 746, 717.

Example 31

N-(2-Aminophenyl)-4-[N-[4-(pyridin-3-yl)-1,4-dioxobutyl]aminomethyl]benzamide (Table 1: Compound 100)

mp: 145–147° C. (dec.); $^1$H NMR (270 MHz, DMSO-d$_6$) δ ppm: 2.37–2.50 (2H, m), 2.62–2.68 (2H, m), 4.13 (2H, s), 4.86 (2H, s), 6.56–6.61 (1H, m), 6.76–6.79 (1H, m), 6.94–6.99 (1H, m), 7.10–7.39 (4H, m), 7.43–7.46 (1H, m), 7.78 (2H, d, J=8.1 Hz), 8.60–8.64 (1H, m), 9.58 (1H, s); IR (KBr)cm$^{-1}$: 3348, 1691, 1655, 1534, 1508, 1458, 1395, 1315, 1083, 746.

Example 32

N-(2-Aminophenyl)-4-[N-(5-chloropyridin-3-yl) oxyacetylaminomethyl]benzamide (Table 1: Compound 158)

mp: 199–201° C. $^1$H NMR (270 MHz, DMSO-d$_6$) δ ppm: 4.43 (2H, d, J=6.6 Hz), 4.75 (2H, s), 4.87 (2H, br. s), 6.60 (1H, dd, J=7.3, 8.1 Hz), 6.78 (1H, d, J=8.1 Hz), 6.97 (1H, dd, J=7.3, 8.1 Hz), 7.16 (1H, d, J=8.1 Hz), 7.37 (2H, d, J=8.1 Hz), 7.59 (1H, d, J=2.2 Hz), 7.93 (2H, d, J=8.1 Hz), 8.25 (1H, d, J=1.5 Hz), 8.81 (1H, t, J=6.6 Hz), 9.64 (1H, s); IR (KBr)cm$^{-1}$: 3288, 3058, 1675, 1633, 1523, 1457, 1314, 912, 755.

Example 33

N-(2-Amino-5-methoxyphenyl)-4-[N-(pyridin-3-yl) oxyacetylaminomethyl]benzamide (Table 1: Compound 175)

mp: 141–144° C.; $^1$H NMR (270 MHz, DMSO-d$_6$) δ ppm: 3.66 (3H, s), 4.43 (2H, d, J=5.9 Hz), 4.49 (2H, br.s), 4.68 (2H, s), 6.62 (1H, dd, J=2.9, 8.8 Hz), 6.75 (1H, d, J=8.8 Hz), 6.91 (1H, d, J=2.2 Hz), 7.37 (4H, m), 7.92 (2H, d, J=8.8 Hz), 8.21 (1H, dd, J=1.5, 4.4 Hz), 8.35 (1H, d, J=2.7 Hz), 8.81 (1H, s), 9.65 (1H, s).

Example 34

N-(2-Aminophenyl)-4-[N-[3-(pyridin-3-yl)-1,3-dioxopropyl]aminomethyl]benzamide (Table 1: Compound 98)

mp: 204–206° C.; $^1$H NMR (270 MHz, DMSO-d$_6$) δ ppm: 4.08 (4/3H, s), 4.39 (4/3H, d, J=5.9 Hz), 4.49 (2/3H, d, J=5.9 Hz), 4.90 (2H, br.s), 5.93 (1/3H, s), 6.60 (1H, t, J=7.3 Hz), 6.78 (1H, d, J=8.1 Hz), 6.97 (1H, t, J=7.3 Hz), 7.16 (1H, d, J=7.3 Hz), 7.3–7.7 (3H, m), 7.8–8.4 (3H, m), 8.6–9.2 (3H, m), 9.64 (1H, s), 14.74 (1/3H, s), (2:1 equilibrium mixture); IR (KBr)cm$^{-1}$: 3282, 1690, 1645, 1527, 1421, 1314, 1217, 1028, 994, 911, 753, 701.

Example 35

N-(2-Aminophenyl)-4-[N-[N-(pyridin-3-yl) aminoacetyl]aminomethyl]benzamide (Table 1: Compound 96)

mp: (amorphous); $^1$H NMR (270 MHz, DMSO-d$_6$) δ ppm: 3.77 (2H, d, J=6.6 Hz), 4.37 (2H, d, J=5.9 Hz), 4.87 (2H, br.s), 6.27 (1H, t, J=5.9 Hz), 6.60 (1H, dd, J=7.3, 7.3 Hz), 6.78 (1H, d, 7.3 Hz) 6.87 (1H, d, J=8.1 Hz), 6.96 (1H, dd, J=7.3, 8.1 Hz), 7.09 (1H, d, J=4.4 Hz), 7.12 (1H, d, J=4.4 Hz), 7.16 (1H, d, J=8.1 Hz), 7.33 (2H, d, J=8.8 Hz), 7.81 (1H, d, J=4.4 Hz), 7.91 (2H, d, J=7.3 Hz), 7.99 (1H, d, J=2.9 Hz), 8.59 (1H, br.t, J=5.1 Hz), 9.63 (1H, br.s); IR (KBr)cm$^{-1}$: 3350, 1658, 1525, 1502, 1314, 750.

Example 36

N-(2-Aminophenyl)-4-[N-(2-aminothiazol-4-yl) acetylaminomethyl]benzamide (Table 1: Compound 220)

mp: (amorphous). $^1$H NMR (270 MHz, DMSO-d$_6$) δ ppm: 3.34 (2H, s), 4.35 (2H, d, J=5.9 Hz), 4.87 (2H, s), 6.25

(1H, s), 6.59 (1H, dd, J=7.3, 7.3 Hz), 6.78 (1H, d, J=7.3 Hz), 6.87 (2H, s), 6.96 (1H, dd, J=7.3, 7.3 Hz), 7.16 (1H, d, J=7.3 Hz), 7.37 (2H, d, J=8.1 Hz), 7.93 (2H, d, J=8.1 Hz), 8.44 (1H, t, J=5.9 Hz), 9.62 (1H, s).

Example 37

N-(2-Aminophenyl)-4-[N-(quinolin-6-yl) carbonylaminomethyl]benzamide (Table 1: Compound 231)

mp: 209–210° C. $^1$H NMR (270 MHz, DMSO-$d_6$) δ ppm: 4.62 (2H, d, J=5.9 Hz), 4.88 (2H, s), 6.60 (1H, t, J=7.7 Hz), 6.78 (1H, d, J=7.3 Hz), 6.95 (1H, d, J=7.3 Hz), 7.17 (1H, d, J=7.3 Hz), 7.49 (2H, d, J=8.8 Hz), 7.62 (1H, dd, J=4.4, 8.1 Hz), 7.96 (2H, d, J=8.8 Hz), 8.10 (1H, d, J=8.8 Hz), 8.23 (1H, dd, J=2.2, 8.8 Hz), 8.38 (1H, m), 8.49 (1H, d, J=8.1 Hz), 8.58 (1H, s), 8.99 (1H, s), 9.64 (1H, s); IR (KBr)cm$^{-1}$: 3301, 1640, 1614, 1545, 1496, 1312, 910, 853, 745.

Example 38

N-(2-Aminophenyl)-4-[N-(furo[3,2-b]pyridin-2-yl) carbonylaminomethyl]benzamide (Table 1: Compound 233)

mp: 191° C. (dec.); $^1$H NMR (270 MHz, DMSO-$d_6$) δ ppm: 4.58 (2H, d, J=5.9 Hz), 4.88 (2H, s), 6.57–6.62 (1H, m), 6.76–6.79 (1H, m), 6.93–6.99 (1H, m), 7.15–7.25 (1H, m), 7.45–7.52 (3H, m), 7.74 (1H, s), 7.95 (2H, d, J=8.1 Hz), 8.13 (1H, d, J=8.8 Hz), 8.63 (1H, d, J=3.7 Hz), 9.54 (1H, t, J=5.9 Hz), 9.64 (1H, s); IR (KBr)cm$^{-1}$: 3406, 1662, 1529, 1507, 1420, 1313, 1209, 1139, 1170, 1139, 924, 741.

Example 39

N-(2-Aminophenyl)-4-[N-(furo[2,3-c]pyridin-2-yl) carbonylaminomethyl]benzamide (Table 1: Compound 234)

mp: 210° C. (dec.); $^1$H NMR (270 MHz, DMSO-$d_6$) δ ppm: 4.58 (2H, J=6.6 Hz), 4.87 (2H, s), 6.57–6.62 (1H, m), 6.76–6.79 (1H, m), 6.93–6.99 (1H, m), 7.14–7.17 (1H, m), 7.47 (2H, d, J=8.1 Hz), 7.66 (1H, s), 7.82 (1H, d, J=4.4 Hz), 7.96 (2H, d, J=8.1 Hz), 8.48 (1H, d, J=5.1 Hz), 9.06 (1H, s), 9.60–9.64 (2H, m); IR (KBr)cm$^{-1}$: 3320, 1653, 1632, 1598, 1457, 1424, 1308, 1187, 1033, 853, 749.

Example 40

N-(2-Hydroxyphenyl)-4-[N-[3-(pyridin-3-yl) propionyl]aminomethyl]benzamide (Table 1: Compound 125)

mp: (amorphous); $^1$H NMR (270 MHz, CD$_3$OD) δ ppm: 2.61 (2H, t, J=7.3 Hz), 3.00 (2H, t, J=7.3 Hz), 4.39 (2H, s), 7.04 (1H, ddd, J=1.5, 8.1, 8.1 Hz), 7.25 (2H, d, J=8.1 Hz), 7.33 (1H, dd, J=5.1, 8.1 Hz), 7.69 (1H, d, J=8.1 Hz), 7.85 (2H, d, J=8.1 Hz), 7.86 (1H, d, J=8.1 Hz), 8.41 (2H, br.s); IR (neat)cm$^{-1}$: 3276, 1645, 1614, 1536, 1509, 1435, 1415, 1385, 1333, 1280, 1247, 1091, 737.

Example 41

N-(2-Hydroxyphenyl)-4-[N-(pyridin-3-yl) oxyacetylaminomethyl]benzamide (Table 1: Compound 93)

mp: (amorphous); $^1$H NMR (270 MHz, DMSO-$d_6$): 4.43 (2H, d, J=6.6 Hz), 4.69 (2H, s), 6.83 (1H, t, J=6.6 Hz), 6.91 (1H, d, J=8.1 Hz), 7.68 (1H, d, J=6.6 Hz), 7.82 (2H, d, J=8.1 Hz), 8.21 (1H, d, J=4.4 Hz), 8.35 (1H, d, J=2.2 Hz), 8.81 (1H, t, J=6.6 Hz), 9.48 (1H, s), 9.75 (1H, s); IR (KBr)cm$^{-1}$: 3399, 1664, 1535, 1236, 1064.

Example 42

N-(2-Hydroxyphenyl)-4-[N-(pyridin-3-yl) acetylaminomethyl]benzamide (Table 1: Compound 117)

mp: 201–202° C.; $^1$H NMR (270 MHz, DMSO-$d_6$) δ ppm: 3.56 (2H, s), 4.37 (2H, d, J=5.9 Hz), 6.83 (1H, ddd, J=1.5, 8.1, 8.1 Hz), 6.92 (1H, br.d, J=8.1 Hz), 7.03 (1H, ddd, J=1.5, 8.1, 8.1 Hz), 7.34 (1H, dd, J=3.7, 8.1 Hz), 7.37 (2H, d, J=8.1 Hz), 7.70 (2H, d, J=8.1 Hz), 7.91 (2H, d, J=8.1 Hz), 8.45 (1H, br.d, J=3.7 Hz), 8.49 (1H, s), 8.73 (1H, t, J=5.9 Hz), 9.47 (1H, s), 9.73 (1H, br.s); IR (KBr)cm$^{-1}$: 3272, 3067, 1661, 1647, 1598, 1536, 1455, 1334, 1288, 1194, 1024, 742.

Example 43

N-(2-Aminophenyl)-4-[N-(pyridin-3-yl)oxyacetyl-N-[3-(pyridin-3-yl)propyl]aminomethyl]benzamide (Table 1: Compound 91)

mp: (amorphous); $^1$H NMR (270 MHz, DMSO-$d_6$) δ ppm: 1.77–1.93 (2H, m), 2.50–2.63 (2H, m), 3.16–3.30 (2H, m), 4.63 (1.2H, s), 4.71 (0.8H, s), 4.88 (1.2H, s), 4.95 (0.8H, s), 5.05 (2H, s), 6.57–6.63 (1H, m), 6.77–6.79 (1H, m), 6.94–7.00 (1H, m), 7.11–7.42 (5H, m), 7.58–7.64 (1H, m), 7.92–8.02 (2H, m), 8.15–8.43 (5H, m), 9.65 (0.6H, s), 9.69 (0.4H, s) (a mixture of rotational isomers).

Example 44

N-(2-Aminophenyl)-4-[N-methyl-N-(pyridin-3-yl) oxyacetyl]aminomethylbenzamide (Table 1: Compound 92)

mp: 117–120° C.; $^1$H NMR (270 MHz, DMSO-$d_6$) δ ppm: 2.84 and 2.99 (total 3H, s), 4.60 and 4.69 (total 2H, s), 4.90 (2H, br.s), 4.99 and 5.08 (total 2H, s), 6.60 (1H, dd, J=7.3, 8.1 Hz), 6.78 (1H, d, J=8.1 Hz), 6.97 (1H, dd, J=7.3, 7.3 Hz), 7.16 (1H, d, J=7.3 Hz), 7.30–7.43 (4H, m), 7.95 and 8.01 (total 2H, d, J=8.1 Hz), 8.17 (1H, d, J=4.4 Hz), 8.31 (1H, d, J=2.9 Hz), 9.65 and 9.68 (total 1H, br.s) (a mixture of rotational isomers); IR (kBr)cm$^{-1}$: 3298, 1665, 1501, 1425, 1310, 1276, 1254, 1078, 799, 746, 703.

Example 45

Preparation of N-(2-Aminophenyl)-4-[N-(pyridin-3-yl)oxamoylaminomethyl]benzamide (Table 1: Compound 95)

(45-1) Ethyl N-(pyridin-3-yl)oxamate (388 mg, 2 mmol) and 638 mg of the compound from the process (1-4) (2 mmol) were dissolved in ethanol, and the mixture was heated with stirring at 40 to 50° C. for 2.5 hours. The precipitated crystals were collected by filtration and washed with 2 mL of ethanol and 3 mL of diethyl ether. The crystals were dried to give 724 mg of N-[2-(N-tert-butoxycarbonyl) aminophenyl]-4-[N-(pyridin-3-yl)oxamoylaminomethyl] benzamide (Yield: 74%).

$^1$H NMR (270 MHz, DMSO-$d_6$) δ ppm: 1.44 (9H, s), 4.49 (2H, d, J=5.9 Hz), 7.10–7.30 (2H, m), 7.35–7.57 (5H, m), 7.93 (2H, d, J=8.1 Hz), 8.21 (1H, br.d, J=5.1 Hz), 8.35 (1H, dd, J=1.5, 5.1 Hz), 8.68 (1H, br.s), 9.00 (1H, d, J=2.9 Hz), 9.70 (1H, t, J=5.9 Hz), 9.82 (1H, s), 10.98 (1H, br.s).

(45-2) To a suspension of 720 mg of the compound from the process (45-1) in 8 mL of methanol was added 8 mL of 4N hydrochloric acid-dioxane solution. After stirring for 3 hours, the mixture was poured into a diluted sodium hydroxide aq. to be basified, and the precipitated crystals were collected by filtration. The crystals were recrystallized from THF/methanol=1:1, to give 280 mg of the desired product.

mp: 254–258° C. (dec.); $^1$H NMR (270 MHz, DMSO-$d_6$) δ ppm: 4.67 (2H, d, J=5.9 Hz), 4.89 (2H, br.s), 6.59 (1H, dd, J=7.3 Hz), 6.77 (1H, d, J=8.1 Hz), 6.97 (1H, dd, J=6.6, 7.3 Hz), 7.16 (1H, d, J=8.1 Hz), 7.38–7.44 (1H, m), 7.43 (2H, d, J=8.1 Hz), 7.95 (2H, d, J=8.1 Hz), 8.18–8.24 (1H, m), 8.34 (1H, dd, J=1.5, 4.4 Hz), 9.00 (1H, d, J=2.1 Hz), 9.63 (1H, s), 9.69 (1H, br.t, J=6.6 Hz), 10.97 (1H, br.s); IR (KBr.cm$^{-1}$): 3312, 3270, 1663, 1636, 1521, 1312, 1296, 1019.

Example 46

Preparation of N-(2-Aminophenyl)-4-[N-(pyridin-3-yl)oxyacetylaminomethyl]benzamide (Table 1: Compound 61)

(46-1) To a suspension of 0.22 g of sodium hydride (60% oil dispersion, 5.5 mmol) in 2 mL of DMF was added dropwise a solution of 0.48 g of 3-hydroxypyridine (5.0 mmol) in 2 mL of DMF at room temperature, and the mixture was stirred for an hour. The resulting brown solution was ice-cooled, 0.81 mL of tert-butyl bromoacetate (5.5 mmol) was added, and the mixture was stirred under ice-cooling for an hour followed by stirring at room temperature for 2 hours. After addition of water, the mixture was extracted with ethyl acetate. The organic layer was washed with saturated brine, dried and evaporated. The residue was purified by column chromatography on silica gel (eluent: chloroform:ethyl acetate=5:1), to give 0.34 g of tert-butyl 3-pyridyloxyacetate (Yield: 32.5%) as a clear oil.

$^1$H NMR (270 MHz, CDCl$_3$) δ ppm: 1.49 (9H, s), 4.56 (2H, s), 7.18–7.24 (2H, m), 8.26 (1H, dd, J=1.5, 3.6 Hz), 8.32 (1H, d, J=2.9 Hz).

(46-2) To a solution of 0.14 g of the compound from the process (46-1) (0.67 mmol) in 2 mL of dichloromethane was added 2 mL of trifluoroacetic acid, and the solution was stirred at room temperature for 3 hours. After evaporation, diisopropyl ether was added, and the precipitated solid was collected by filtration and dried to give 0.15 g of 3-pyridyloxyacetic acid trifluoroacetate (Yield: 83.8%) as a light yellow solid.

$^1$H NMR (270 MHz, DMSO-$d_6$) δ ppm: 4.86 (2H, s), 7.57 (1H, dd, J=4.4, 8.1 Hz), 7.67 (1H, ddd, J=1.5, 1.5, 8.8 Hz), 8.31 (1H, d, J=5.1 Hz), 8.46 (1H, d, J=2.1 Hz), 13.00 (1H, br.s).

(46-3) To a suspension of 100 mg of the compound from the process (46-2) (0.37 mmol) and 255 mg of the compound from Example 1, the process (1-4) (0.75 mmol) in 5 mL of dichloromethane was added 0.14 mL of triethylamine (1.0 mmol), and the mixture was cooled with ice. Under ice-cooling, to the mixture was added a solution of 140 mg of 2-chloro-1,3-dimethylimidazolinium chloride (0.83 mmol) in 6 mL of dichloromethane, and the mixture was warmed to room temperature with stirring for 7 hours, and left at room temperature overnight. After adding water and saturated brine, the mixture was extracted with chloroform.

The organic layer was washed with saturated brine, dried and evaporated. The residue was purified by column chromatography on silica gel (eluent:ethyl acetate:methanol= 10:1) to give 0.37 g of N-[2-(N-tert-butoxycarbonyl) aminophenyl]-4-[N-(pyridin-3-yl)oxyacetylaminomethyl] benzamide (Yield: quantitative) as a clear oil.

$^1$H NMR (270 MHz, CDCl$_3$) δ ppm: 1.52 (9H, s), 4.62 (2H, s), 4.63 (2H, d, J=7.3 Hz), 6.76 (1H, br.s), 6.90–7.00 (1H, br.s), 7.15–7.35 (5H, m), 7.40 (2H, d, J=8.1 Hz), 7.82 (1H, d, J=8.1 Hz), 7.95 (2H, d, J=8.1 Hz), 8.32 (1H, dd, J=2.1, 4.4 Hz), 8.37 (1H, d, J=2.8 Hz), 9.20 (1H, br.s).

(46-4) To a solution of 175 mg of the compound from the process (46-3) (0.37 mmol) in 2 mL of dioxane and 2 mL of methanol was added 2 mL of 4N hydrochloric acid-dioxane, and the mixture was stirred at room temperature for 2 hours. After adding saturated sodium bicarbonate aq., the mixture was extracted with ethyl acetate. The organic layer was washed with saturated brine, dried and evaporated. To the residue was added methanol and diisopropyl ether, and the precipitated solid was collected by filtration and dried to give 90 mg of N-(2-aminophenyl)-4-[N-(pyridin-3-yl) oxyacetylaminomethyl]benzamide (Yield: 64.6%) as an opalescent solid.

mp: 154–155° C.; $^1$H NMR (270 MHz, DMSO-$d_6$) δ ppm: 4.42 (2H, d, J=5.9 Hz), 4.69 (2H, s), 4.89 (2H, br.s), 6.59 (1H, dd, J=7.3, 8.1 Hz), 6.78 (1H, d, J=8.1 Hz), 6.97 (1H, dd, J=6.6, 7.3 Hz), 7.16 (1H, d, J=7.3 Hz), 7.33–7.39 (4H, m), 7.92 (2H, d, J=8.1 Hz), 8.21 (1H, dd, J=1.5, 4.4 Hz), 8.35 (1H, d, J=2.9 Hz), 8.80 (1H, br.t, J=5.9 Hz), 9.63 (1H, br.s); IR (KBr)cm$^{-1}$: 3307, 1672, 1631, 1523, 1456, 1429, 1269, 1231, 803, 756.

Example 47

Preparation of N-(2-Aminophenyl)-4-[N-[2-(pyridin-3-yl)oxy]propionylaminomethyl]benzamide (Table 4: Compound 3)

(47-1) To a suspension of 1.20 g of sodium hydride (60% oil dispersion; 30.0 mmol) in 10 mL of dry DMF at room temperature were added dropwise 2.85 g of 3-hydroxypyridine (30 mmol) in 10 mL of dry DMF, maintaining the temperature below 40° C., and the mixture was stirred at room temperature for 90 min. Under ice-cooling, 6.28 g of tert-butyl 2-bromopropionate (30 mmol) in 10 mL of dry DMF were slowly added dropwise, maintaining the inner temperature within 5 to 10° C., and then the mixture was warmed to room temperature with stirring for 4 hours. After neutralizing with saturated sodium bicarbonate aq., the mixture was extracted with ethyl acetate. The organic layer was washed with water and then saturated brine, dried and evaporated. The residue was purified by column chromatography on silica gel (eluent: n-hexane:ethyl acetate=2:1) to give 4.15 g of tert-butyl 2-(pyridin-3-yl)oxypropionate (Yield: 62%) as a brown oil.

$^1$H NMR (270 MHz, CDCl$_3$) δ ppm: 1.44 (9H, s), 1.61 (3H, d, J=7.3 Hz), 4.66 (1H, q, J=7.3 Hz), 7.13–7.23 (2H, m), 8.24 (1H, dd, J=1.5, 4.4 Hz), 8.29 (1H, d, J=2.1 Hz).

(47-2) To a solution of 1.65 g of the compound from the process (47-1) (7.4 mmol) in 9 mL of dichloromethane was added 9 mL of trifluoroacetic acid, maintaining the temperature below 30° C., and then the mixture was stirred at room temperature for 8 hours. After evaporation, diisopropyl ether was added and the precipitated solid was collected by filtration and dried to give 1.86 g of 2-(pyridin-3-yl) oxypropionic acid trifluoroacetate (Yield 43.5%) as a light brown solid.

$^1$H NMR (270 MHz, DMSO-$d_6$) δ ppm: 1.53 (3H, d, J=6.6 Hz), 5.12 (1H, q, J=6.6 Hz), 7.60–7.75 (2H, m), 8.35 (1H, d, J=5.1 Hz), 8.47 (1H, s), 12.9 (1H, br.s).

(47-3) To a suspension of 0.98 g of the compound from the process (47-2) (3.5 mmol) and 1.02 g of the compound from Example 1, the process (1-4) (3.0 mmol) in 20 mL of dichloromethane was added 1.3 mL of triethylamine (9.0 mmol) and then the mixture was ice-cooled. Under ice-cooling, 0.59 g of 2-chloro-1,3-dimethylimidazolinium chloride (3.5 mmol) in 5 mL of dichloromethane was added dropwise, and the mixture was stirred for additional 2 hours. The mixture was neutralized with saturated sodium bicarbonate aq., and then extracted with chloroform. The organic layer was washed with saturated brine, dried and evaporated. The residue was purified by column chromatography on silica gel (eluent: ethyl acetate:methanol=10:1) to give 1.64 g of N-[2-(N-tert-butoxycarbonylamino)phenyl]-4-[N-[2-(pyridin-3-yl)oxypropionyl]aminomethyl]benzamide as a mixture with 1,3-dimethyl-2-imidazolinone.

$^1$H NMR (270 MHz, CDCl$_3$) δ ppm: 1.51 (9H, s), 1.64 (3H, d, J=7.3 Hz), 4.54 (2H, m), 4.78 (1H, q, J=6.6 Hz), 6.87 (2H, br.s), 7.13–7.30 (6H, m) 7.81 (1H, d, J=7.3 Hz), 7.90 (2H, d, J=8.1 Hz), 8.29 (1H, dd, J=1.5, 4.4 Hz), 8.33 (1H, d, J=2.1 Hz), 9.22 (1H, br.s).

(47-4) The compound from the process (47-3) (1.64 g) was dissolved in 10 mL of dioxane and 4 mL of methanol. To the solution was added 10 mL of 4N hydrochloric acid-dioxane solution at room temperature, and the mixture was stirred for 2 hours. The mixture was neutralized with saturated sodium bicarbonate aq. and extracted with ethyl acetate. The organic layer was washed with saturated brine, dried and evaporated. To the residue were added methanol and diisopropyl ether, and the precipitated solid was collected by filtration and dried to give 0.71 g of N-(2-aminophenyl)-4-[N-[2-(pyridin-3-yl)oxy]propionylaminomethyl]benzamide (Yield: 60.5% for the 2 steps) as a white solid.

mp: 171–173° C. (dec.); $^1$H NMR (270 MHz, DMSO-d$_6$) δ ppm: 1.51 (3H, d, J=6.6 Hz), 4.36 (2H, d, J=5.9 Hz), 4.89 (2H, br.s), 4.90 (1H, t, J=6.6 Hz), 6.60 (1H, dd, J=6.6, 7.3 Hz), 6.78 (1H, d, J=8.1 Hz), 6.97 (1H, dd, J=6.6, 7.3 Hz), 7.15 (1H, d, J=7.3 Hz), 7.27 (2H, d, J=8.1 Hz), 7.33–7.37 (2H, m), 7.89 (2H, d, J=8.1 Hz), 8.21 (1H, dd, J=2.9, 2.9 Hz), 8.32 (1H, d, J=1.5 Hz), 8.82 (1H, t, J=5.9 Hz), 9.63 (1H, br.s).

Example 48

Preparation of N-(2-Aminophenyl)-4-[N-(pyridin-3-yl)methoxycarbonylaminomethyl]benzamide (Table 1: Compound 82)

(48-1) To a solution of 384 mg of 3-pyridinemethanol (3.52 mmol) in 5 mL of dry THF were added 523 mg of N,N'-carbonyldiimidazole (3.22 mmol) at room temperature. After stirring for an hour, to the mixture was added 1.0 g of the compound from Example 1, the process (1-4) (2.93 mmol) in 6 mL of dry THF.

After being left at room temperature overnight, to the mixture was added 100 mL of chloroform, and the mixture was washed with water (3×20 mL) and then saturated brine, and dried over anhydrous magnesium sulfate. After evaporating the solvent under reduced pressure, the residue was purified by column chromatography on silica gel (eluent: chloroform:methanol=30:1) to give 1.27 g of N-[2-(N-tert-butoxycarbonyl)aminophenyl]-4-[N-(pyridin-3-yl)methoxycarbonylaminomethyl]benzamide (Yield: quantitative) as an amorphous solid.

$^1$H NMR (270 MHz, CDCl$_3$) δ ppm: 1.51 (9H, s), 4.45 (2H, d, J=5.9 Hz), 5.16 (1H, s), 7.10–7.50 (7H, m), 7.70 (1H, d, J=8.1 Hz), 7.80 (1H, d, J=7.3 Hz), 7.93 (1H, d, J=8.1 Hz), 8.57 (1H, d, J=4.4 Hz), 8.63 (1H, s), 9.17 (1H, s).

(48-2) The compound from the process (48-1) (1.2 g, 2.8 mmol) was dissolved in 10 mL of methanol. To the solution was added 20 mL of 4N-hydrochloric acid-dioxane. The mixture was stirred at room temperature for 1.5 hours, and then poured into diluted sodium hydroxide aq. and extracted with chloroform (3×60 mL). The combined organic layer was washed twice with saturated brine, dried over anhydrous magnesium sulfate and concentrated to give 0.88 g of crystals, which were then recrystallized from 16 mL of ethanol, to give 668 mg of N-(2-aminophenyl)-4-[N-(pyridin-3-yl)methoxycarbonylaminomethyl]benzamide (Yield: 73%).

mp: 159–160° C.; $^1$H NMR (270 MHz, DMSO-d$_6$) δ ppm: 4.28 (2H, d, J=5.9 Hz), 4.86 (2H, s), 5.10 (2H, s), 6.60 (1H, t, J=7.3 Hz), 6.78 (1H, d, J=7 Hz), 6.97 (1H, t, J=7 Hz), 7.17 (1H, d, J=8 Hz), 7.30–7.50 (3H, m), 7.78 (1H, d, J=8 Hz), 7.93 (2H, d, J=8 Hz), 8.53 (1H, d, J=3.7 Hz), 8.59 (1H, s), 9.61 (1H, s). IR (KBr)cm$^{-1}$: 3295, 1648, 1541, 1508, 1457, 1309, 1183, 742.

As described in Example 48, the compounds of Examples 49 to 87 were prepared, each of whose melting point (mp), $^1$H NMR data and/or IR data are shown below.

Example 49

N-(2-Aminophenyl)-4-[N-(benzyloxycarbonyl)aminomethyl]benzamide (Table 1: Compound 11)

mp: 174–178° C.; $^1$H NMR (270 MHz, DMSO-d$_6$) δ ppm: 4.28 (2H, d, J=5.9 Hz), 4.89 (2H, br.s), 5.06 (2H, s), 6.59 (1H, dd, J=7.3, 8.1 Hz), 6.78 (1H, d, J=8.1 Hz), 6.97 (1H, dd, J=7.3, 8.1 Hz), 7.16 (1H, d, J=7.3 Hz), 7.30–7.40 (6H, m), 7.93 (3H, m), 9.63 (1H, s). IR (KBr)cm$^{-1}$: 3332, 1687, 1652, 1536, 1456, 1279, 747.

Example 50

N-(2-Aminophenyl)-4-[N-(4-(imidazol-1-yl)benzyl)oxycarbonylaminomethyl]benzamide (Table 1: Compound 47)

mp: 195–198° C.; $^1$H NMR (270 MHz, DMSO-d$_6$) δ ppm: 4.29 (2H, d, J=6.6 Hz), 4.88 (2H, s), 5.10 (2H, s), 6.60–6.63 (1H, m), 6.78 (1H, d, J=8.1 Hz), 6.97 (1H, t, J=7.3 Hz), 7.11 (1H, s), 7.16 (1H, d, J=7.3 Hz), 7.37 (2H, d, J=8.1 Hz), 7.49 (2H, d, J=8.8 Hz), 7.66 (2H, d, J=8.1 Hz), 7.74 (1H, s), 7.92–7.96 (3H, m), 8.25 (1H, s), 9.62 (1H, s).

Example 51

N-(2-Aminophenyl)-4-[N-(pyridin-2-yl)methoxycarbonylaminomethyl]benzamide (Table 1: Compound 171)

mp: 166–167° C.; $^1$H NMR (270 MHz, DMSO-d$_6$) δ ppm: 4.30 (2H, d, J=5.9 Hz), 4.88 (2H, br.s), 5.12 (2H, s), 6.60 (1H, dd, J=7.3, 8.1 Hz) 6.78 (1H, d, J=8.1 Hz), 6.97 (1H, ddd, J=1.5, 7.3, 8.1 Hz), 7.16 (1H, d, J=7.3 Hz), 7.33 (1H, dd, J=3.7, 7.3 Hz), 7.40 (3H, d, J=8.1 Hz), 7.83 (1H, ddd, J=1.5, 7.3, 8.1 Hz), 7.94 (2H, d, J=8.1 Hz), 8.03 (1H, t, J=5.9 Hz), 8.55 (1H, d, J=5.1 Hz), 9.62 (1H, br.s); IR (KBr)cm$^{-1}$: 3334, 1694, 1632, 1580, 1276, 755.

Example 52

N-(2-Aminophenyl)-4-[N-[2-(pyridin-2-yl)ethoxycarbonyl]aminomethyl]benzamide (Table 1: Compound 172)

mp: 146–148° C.; $^1$H NMR (270 MHz, DMSO-d$_6$) δ ppm: 3.04 (2H, t, J=6.6 Hz), 4.23 (2H, d, J=5.9 Hz), 4.36 (2H, t, J=6.6 Hz), 4.88 (2H, br.s), 6.60 (1H, dd, J=7.3, 8.1 Hz), 6.78 (1H, d, J=8.1 Hz), 6.97 (1H, dd, J=7.3, 8.1 Hz), 7.15–7.30 (3H, m), 7.34 (2H, d, J=8.1 Hz), 7.69–7.77 (2H, m), 7.92 (2H, d, J=7.3 Hz), 8.50 (1H, d, J=4.4 Hz), 9.62 (1H, br.s); IR (KBr)cm$^{-1}$: 3330, 1690, 1633, 1594, 1524, 1277, 760.

Example 53

N-(2-Aminophenyl)-4-[N-(6-methylpyridin-2-yl)methoxycarbonylaminomethyl]benzamide (Table 1: Compound 179)

mp: 138° C.; $^1$H NMR (270 MHz, DMSO-d$_6$) δ ppm: 2.47 (3H, s), 4.30 (2H, d, J=5.9 Hz), 5.07 (4H, s), 6.63 (1H, t, J=8.1 Hz), 6.80 (1H, d, J=7.34), 6.98 (1H, t, J=8.1 Hz), 7.18 (3H, d, J=7.3 Hz), 7.40 (2H, d, J=8.1 Hz), 7.71 (1H, t, J=8.1 Hz), 7.94 (2H, d, J=8.1 Hz), 8.03 (1H, t, J=5.9 Hz), 9.66 (1H, s); IR (KBr)cm$^{-1}$: 3335, 1693, 1634, 1259.

Example 54

N-(2-Aminophenyl)-4-[N-[2-(pyridin-3-yl)ethoxycarbonyl]aminomethyl]benzamide (Table 1: Compound 83)

mp: 120–125° C.; $^1$H NMR (270 MHz, DMSO-d$_6$) δ ppm: 2.91 (2H, t, J=6.6 Hz), 4.22 (4H, t, J=6.6 Hz), 4.89 (2H, s), 6.55–6.63 (1H, m), 6.78 (1H, dd, J=8.1, 1.5 Hz), 6.97 (1H, t, J=6.6 Hz), 7.17 (1H, d, J=6.6 Hz), 7.33 (3H, d, J=8.1 Hz), 7.69 (1H, d, J=8.1 Hz), 7.79 (1H, t, J=6.6 Hz), 7.93 (2H, d, J=8.0 Hz), 8.43–8.49 (2H, m), 9.62 (1H, s); IR (KBr)cm$^{-1}$: 3234, 1705, 1655, 1260.

Example 55

N-(2-Aminophenyl)-4-[N-[3-(pyridin-3-yl)propyloxycarbonyl]aminomethyl]benzamide (Table 1: Compound 84)

mp: 121–124° C.; $^1$H NMR (270 MHz, DMSO-d$_6$) δ ppm: 1.83–1.94 (2H, m), 2.67 (2H, t, J=7.3 Hz), 3.98 (2H, t, J=6.6 Hz), 4.26 (2H, d, J=5.9 Hz), 4.89 (2H, br.s), 6.60 (1H, dd, J=8.1, 8.1 Hz), 6.78 (1H, d, J=7.3 Hz), 6.97 (1H, ddd, J=1.5, 7.3, 8.1 Hz), 7.16 (1H, d, J=8.1 Hz), 7.29–7.33 (1H, m), 7.37 (1H, d, J=8.1 Hz), 7.64 (1H, d, J=8.1 Hz), 7.81 (1H, dd, J=5.9, 6.6 Hz), 7.94 (2H, d, J=8.1 Hz), 8.40–8.44 (2H, m), 9.63 (1H, br.s); IR (KBr)cm$^{-1}$: 3348, 1696, 1635, 1523, 1458, 1302, 1272, 1141, 1019, 754, 713.

Example 56

N-(2-Aminophenyl)-4-[N-(2-methylpyridin-3-yl)methoxycarbonylaminomethyl]benzamide (Table 1: Compound 142)

mp: 164–165° C.; $^1$H NMR (270 MHz, DMSO-d$_6$) ppm: 2.49 (3H, s), 4.28 (2H, d, J=6.6 Hz), 4.89 (2H, s), 5.10 (2H, s), 6.60 (1H, t, J=7.6 Hz), 6.78 (1H, d, J=8.1 Hz), 6.90 (1H, t, J=7.3 Hz), 7.17 (1H, d, J=7.3 Hz), 7.21–7.26 (1H, m), 7.37 (2H, d, J=8.1 Hz), 7.68 (1H, d, J=6.6 Hz), 7.92–8.00 (3H, m), 8.39 (1H, d, J=4.4 Hz), 9.62 (1H, s); IR (KBr)cm$^{-1}$: 3332, 1719, 1630, 1260.

Example 57

N-(2-Aminophenyl)-4-[N-(6-methylpyridin-3-yl)methoxycarbonylaminomethyl]benzamide (Table 1: Compound 144)

mp: 164–165° C.; $^1$H NMR (270 MHz, DMSO-d$_6$) δ ppm: 2.46 (3H, s), 4.27 (2H, d, J=6.6 Hz), 4.88 (2H, s), 5.05 (2H, s), 6.59 (1H, dt, J=1.5, 8.1 Hz), 6.78 (1H, dd, J=1.5, 8.1 Hz), 6.97 (1H, dt, J=1.5, 7.3 Hz), 7.17 (1H, d, J=7.3 Hz), 7.26 (1H, d, J=8.1 Hz), 7.36 (2H, d, J=8.1 Hz), 7.67 (1H, dd, J=2.2, 8.1 Hz), 7.93 (3H, d, J=8.1 Hz), 8.45 (1H, d, J=1.5 Hz), 9.62 (1H, s); IR (KBr)cm$^{-1}$: 3293, 1701, 1632, 1260.

Example 58

N-(2-Aminophenyl)-4-[N-(2-chloropyridin-3-yl)methoxycarbonylaminomethyl]benzamide (Table 1: Compound 155)

mp: (amorphous); $^1$H NMR (270 MHz, DMSO-d$_6$) ppm: 4.30 (2H, d, J=5.9 Hz), 5.00 (2H, s), 5.13 (2H, s), 6.61 (1H, t, J=7.3 Hz), 6.79 (1H, dd, J=1.5, 8.1 Hz), 6.98 (1H, dt, J=1.5, 7.3 Hz), 7.17 (1H, d, J=6.6 Hz), 7.39 (2H, d, J=8.8 Hz), 7.47–7.52 (1H, m), 7.91–7.96 (3H, m), 8.08 (1H, t, J=5.9 Hz), 8.40 (1H, dd, J=4.4, 1.5 Hz), 9.64 (1H, s); IR (KBr)cm$^{-1}$: 3340, 1702, 1632, 1273.

Example 59

N-(2-Aminophenyl)-4-[N-(6-chloropyridin-3-yl)methoxycarbonylaminomethyl]benzamide (Table 1: Compound 157)

mp: 180–185° C.; $^1$H NMR (270 MHz, DMSO-d$_6$) δ ppm: 4.24 (2H, d, J=5.9 Hz), 4.89 (2H, br.s), 5.10 (2H, s), 6.60 (1H, t, J=7.3 Hz), 6.78 (1H, d, J=8.1 Hz), 6.97 (1H, dt, J=1.5, 8.1 Hz), 7.16 (1H, d, J=6.6 Hz), 7.37 (2H, d, J=8.1 Hz), 7.56 (1H, d, J=8.1 Hz), 7.85–8.02 (4H, m), 8.44 (1H, d, J=2.2 Hz), 9.62 (1H, s); IR (KBr)cm$^{-1}$: 3346, 3282, 1696, 1533, 1271.

Example 60

N-(2-Aminophenyl)-4-[N-(pyridin-4-yl)methoxycarbonylaminomethyl]benzamide (Table 1: Compound 181)

mp: 180–183° C.; $^1$H NMR (270 MHz, DMSO-d$_6$) δ ppm: 4.30 (2H, d, J=6.6 Hz), 4.89 (2H, s), 5.12 (2H, s), 6.60 (1H, dd, J=7.3, 7.3 Hz), 6.78 (1H, dd, J=1.5, 7.3 Hz), 6.97 (1H, ddd, J=1.5, 7.3, 8.1 Hz), 7.16 (1H, d, J=7.3 Hz), 7.34 (2H, d, J=5.9 Hz), 7.39 (2H, d, J=8.1 Hz), 7.94 (2H, d, J=8.1 Hz), 8.09 (1H, t, J=5.9 Hz), 8.57 (1H, d), 9.64 (1H, br.s); IR (KBr)cm$^{-1}$: 3394, 3290, 1711, 1645, 1624, 1535, 1504, 1321, 1251, 1138, 1049, 763.

Example 61

N-(2-Aminophenyl)-4-[N-[2-(thiophen-3-yl)ethoxycarbonyl]aminomethyl]benzamide (Table 1: Compound 203)

mp: (amorphous); $^1$H NMR (270 MHz, DMSO-d$_6$) δ ppm: 2.90 (2H, t, J=7.3 Hz), 4.17–4.26 (4H, m), 4.89 (2H, s), 6.60 (1H, t, J=8.1 Hz), 6.78 (1H, d, J=6.6 Hz), 6.97 (1H, t, J=7.3 Hz), 7.06 (1H, d, J=5.1 Hz), 7.17 (1H, d, J=7.3 Hz), 7.26 (1H, s), 7.36 (2H, d, J=8.1 Hz), 7.47 (1H, t, J=2.2 Hz), 7.81 (1H, t, J=5.9 Hz), 7.93 (2H, d, J=8.1 Hz), 9.63 (1H, s); IR (KBr)cm$^{-1}$: 3314, 1716, 1638, 1252.

Example 62

N-(2-Aminophenyl)-4-[N-(3-phenyloxazol-5-yl)methoxycarbonylaminomethyl]benzamide (Table 1: Compound 211)

mp: 192–195° C.; $^1$H NMR (270 MHz, DMSO-d$_6$) δ ppm: 4.30 (2H, d, J=5.9 Hz), 4.89 (2H, s), 5.25 (2H, s), 6.60 (1H, t, J=6.6 Hz), 6.68 (1H, d, J=8.1 Hz), 6.94 (1H, t, J=7.3 Hz), 7.09 (1H, s), 7.16 (1H, d, J=7.3 Hz), 7.39 (2H, d, J=8.1 Hz), 7.51 (4H, d, J=2.2 Hz), 7.87–7.96 (5H, m), 8.12 (1H, t, J=5.9 Hz), 9.63 (1H, s); IR (KBr)cm$^{-1}$: 3292, 1718, 1630, 1262.

Example 63

N-(2-Aminophenyl)-4-[N-(thiazol-5-yl)methoxycarbonylaminomethyl]benzamide (Table 1: Compound 216)

mp: 168–175° C.; $^1$H NMR (270 MHz, DMSO-d$_6$) δ ppm: 4.28 (2H, d, J=5.9 Hz), 4.91 (2H, br.s), 5.30 (2H, s), 6.60 (1H, dd, J=7.3, 7.3 Hz), 6.78 (1H, d, J=8.1 Hz), 6.97 (1H, dd, J=7.3, 8.1 Hz), 7.16 (1H, d, J=7.3 Hz), 7.36 (2H, d, J=8.1 Hz), 7.91–8.00 (4H, m), 9.09 (1H, s), 9.63 (1H, s); IR (KBr)cm$^{-1}$: 3346 (br.), 1697, 1636, 1525, 1456, 1271, 873, 753.

Example 64

N-(2-Aminophenyl)-4-[N-[2-(4-methylthiazol-5-yl)ethoxycarbonyl]aminomethyl]benzamide (Table 1: Compound 217)

mp: 130–133° C.; $^1$H NMR (270 MHz, DMSO-d$_6$) δ ppm: 2.32 (3H, s), 3.07 (2H, t, J=5.9 Hz), 4.15 (2H, t, J=5.9 Hz), 4.25 (2H, d, J=6.6 Hz), 4.89 (2H, s), 6.60 (1H, t, J=5.9 Hz), 6.78 (1H, dd, J=7.3, 1.5 Hz), 6.97 (1H, dt, J=1.5, 7.3 Hz), 7.16 (1H, d, J=8.1 Hz), 7.35 (2H, d, J=8.1 Hz), 7.83 (1H, t, J=5.9 Hz), 7.94 (2H, d, J=8.1 Hz), 8.85 (1H, s), 9.62 (1H, s); IR (KBr)cm$^{-1}$: 3350, 1691, 1635, 1270.

Example 65

N-(2-Aminophenyl)-4-[N-(1-methylpiperidin-3-yl)methoxycarbonylaminomethyl]benzamide (Table 1: Compound 225)

mp: 130–135° C.; $^1$H NMR (270 MHz, DMSO-d$_6$) δ ppm: 1.49–1.78 (3H, m), 1.83–2.01 (3H, m), 2.30 (3H, s), 2.85 (2H, t), 3.74–3.94 (2H, m), 4.25 (2H, d, J=5.8 Hz), 6.55–6.62 (3H, m), 6.78 (1H, d, J=8.1 Hz), 6.97 (1H, t, J=7.3 Hz), 7.16 (1H, d, J=8.1 Hz), 7.37 (2H, d, J=8.1 Hz), 7.79 (1H, t, J=6.6 Hz), 7.93 (2H, d, J=8.0 Hz), 9.66 (1H, s); IR (KBr)cm$^{-1}$: 3323, 2722, 1702, 1648, 1263.

Example 66

N-(2-Aminophenyl)-4-[N-(4-methylpiperazin-1-yl)methoxycarbonylaminomethyl]benzamide (Table 1: Compound 227)

mp: (amorphous); $^1$H NMR (270 MHz, DMSO-d$_6$) δ ppm: 1.73 (2H, t, J=6.6 Hz), 2.36–2.63 (13H, m), 4.00 (2H, t, J=6.6 Hz), 4.30 (2H, d, J=5.8 Hz), 6.55–6.63 (4H, m), 6.78 (1H, d, J=6.6 Hz), 6.97 (1H, t, J=7.3 Hz), 7.16 (1H, d, J=7.3 Hz), 7.37 (2H, d, J=8.7 Hz), 7.73 (1H, t, J=5.9 Hz), 7.94 (2H, d, J=8.0 Hz), 9.66 (1H, s); IR (KBr)cm$^{-1}$: 3341, 2706, 1701, 1262.

Example 67

N-(2-Aminophenyl)-4-[N-(tetrahydrofuran-3-yl)methoxycarbonylaminomethyl]benzamide (Table 1: Compound 221)

mp: (amorphous); $^1$H NMR (270 MHz, DMSO-d$_6$) δ ppm: 1.50–1.60 (1H, m), 1.88–2.00 (1H, m), 2.44–2.54 (1H, m), 3.41–3.47 (1H, m), 3.56–3.77 (3H, m), 3.85–4.04 (2H, m), 4.25 (2H, d, J=5.9 Hz), 4.89 (2H, s), 6.60 (1H, dd, J=7.3, 7.3 Hz), 6.78 (1H, d, J=8.1 Hz), 6.97 (1H, dd, J=7.3, 8.1 Hz), 7.17 (1H, d, J=8.1 Hz), 7.37 (2H, d, J=8.1 Hz), 7.81 (1H, t, J=5.9 Hz), 7.94 (2H, d, J=8.1 Hz), 9.62 (1H, br.s); IR (KBr)cm$^{-1}$: 3349, 1695, 1635, 1523, 1457, 1259, 754.

Example 68

N-(2-Aminophenyl)-4-[N-(phenoxycarbonyl)aminomethyl]benzamide (Table 1: Compound 12)

mp: 174–175° C.; $^1$H NMR (270 MHz, DMSO-d$_6$) δ ppm: 4.36 (2H, d, J=5.9 Hz), 4.90 (2H, br.s), 6.60 (1H, dd, J=7.3, 7.3 Hz), 6.77 (1H, dd, J=7.3, 7.3 Hz), 6.98 (1H, ddd, J=1.5, 7.3, 7.3 Hz), 7.05–7.24 (4H, m), 7.39–7.46 (4H, m), 7.97 (2H, d, J=8.1 Hz), 8.41 (1H, t, J=5.9 Hz), 9.65 (1H, br.s); IR (KBr)cm$^{-1}$: 3443, 3362, 3313, 1732, 1706, 1636, 1527, 1493, 1458, 1305, 1217, 748.

Example 69

N-(2-Aminophenyl)-4-[N-(pyridin-3-yl)oxycarbonylaminomethyl]benzamide (Table 1: Compound 81)

mp: 209° C.(dec.); $^1$H NMR (270 MHz, DMSO-d$_6$) δ ppm: 4.38 (2H, d, J=6.6 Hz), 4.90 (2H, br.s), 6.55–6.63 (1H, m), 6.78 (1H, d, J=8.1 Hz), 7.00 (1H, dd, J=7.3, 7.3 Hz), 7.17 (1H, d, J=8.8 Hz), 7.37–7.47 (3H, m), 7.64 (1H, d, J=8.8 Hz), 7.97 (2H, d, J=8.1 Hz), 8.43 (2H, d, J=3.1 Hz); 8.59 (1H, t, J=5.9 Hz), 9.66 (1H, br.s).

Example 70

N-(2-Amino-5-fluorophenyl)-4-[N-(pyridin-3-yl)methoxycarbonylaminomethyl]benzamide (Table 1: Compound 110)

mp: 160–162° C.; $^1$H NMR (270 MHz, DMSO-d$_6$) δ ppm: 4.28 (2H, d, J=6.6 Hz), 4.81 (2H, s), 5.10 (2H, s), 6.70–6.90 (2H, m), 7.10–8.00 (8H, m), 8.53 (1H, d, J=3.6 Hz), 8.59 (1H, s), 9.61 (1H, s); IR (KBr)cm$^{-1}$: 3269, 1716, 1638, 1488, 1436, 1247, 1141, 1043, 744.

Example 71

N-(2-Aminophenyl)-4-[N-(2-aminophenyl)methoxycarbonylaminomethyl]benzamide (Table 1: Compound 51)

mp: 149–151° C. (dec.); $^1$H NMR (270 MHz, DMSO-d$_6$) δ ppm: 4.28 (2H, d, J=5.9 Hz), 4.88 (2H, s), 4.96 (2H, s), 5.06 (2H, s), 6.53 (1H, dd, J=7.3, 7.3 Hz), 6.56–6.67 (2H, m), 6.78 (1H, dd, J=1.5, 8.1 Hz), 6.93–7.12 (3H, m), 7.16 (1H, d, J=6.6 Hz), 7.38 (2H, d, J=8.1 Hz), 7.86 (1H, t-like, J=5.9 Hz), 7.93 (2H, d, J=8.1 Hz), 9.61 (1H, s); IR (KBr) cm$^{-1}$: 3336, 1685, 1632, 1527, 1276, 748.

Example 72

N-(2-Aminophenyl)-4-[N-(quinuclidin-3-yl)oxycarbonylaminomethyl]benzamide (Table 1: Compound 228)

mp: (amorphous); $^1$H NMR (270 MHz, DMSO-d$_6$) δ ppm: 1.30–1.90 (4H, m), 1.90 (1H, br.s), 2.45–2.80 (6H, m), 3.04–3.13 (1H, m), 4.15 (2H, d, J=5.9 Hz), 4.55–4.60 (1H, m), 4.88 (2H, br.s), 6.60 (1H, ddd, J=1.5, 7.3, 7.3 Hz), 6.78 (1H, d, J=8.1 Hz), 6.97 (1H, ddd, J=1.5, 7.3, 7.3 Hz), 7.17 (1H, d, J=6.6 Hz), 7.37 (2H, d, J=8.1 Hz), 7.78 (1H, t, J=5.9

Hz), 7.94 (1H, d, J=7.3 Hz), 9.62 (1H, s); IR (KBr)cm$^{-1}$: 3328, 2942, 1700, 1648, 1504, 1259, 749.

Example 73

N-(2-Aminophenyl)-4-[N-(3-aminophenyl)methoxycarbonylaminomethyl]benzamide (Table 1: Compound 52)

mp: 149–153° C. (dec.); $^1$H NMR (270 MHz, DMSO-d$_6$) δ ppm: 4.27 (2H, d, J=5.9 Hz), 4.88 and 4.89 (total 4H, each br.s), 5.08 (2H, s), 6.47–6.63 (3H, m), 6.78 (1H, d, J=8.1 Hz), 6.94–7.02 (2H, m) 7.15 (1H, dd, J=7.3, 8.8 Hz), 7.37 (2H, d, J=8.1 Hz), 7.84 (1H, t, J=5.9 Hz), 7.93 (2H, d, J=8.8 Hz), 9.61 (1H, br.s); IR (KBr)cm$^{-1}$: 3367, 1682, 1632, 1523, 1457, 1261, 754.

Example 74

N-(2-Aminophenyl)-4-[N-(1-methylimidazol-5-yl)methoxycarbonylaminomethyl]benzamide (Table 1: Compound 218)

mp: 162–165° C. (dec.); $^1$H NMR (270 MHz, DMSO-d$_6$) δ ppm: 3.62 (3H, s), 4.27 (2H, d, J=5.9 Hz), 4.91 (2H, br.s), 5.05 (2H, s), 6.60 (1H, dd, J=7.3, 7.3 Hz), 6.78 (1H, d, J=8.1 Hz), 6.95–7.00 (2H, m), 7.16 (1H, d, J=7.3 Hz), 7.36 (2H, d, J=8.1 Hz), 7.63 (1H, s), 7.87–7.95 (3H, m), 9.64 (1H, br.s); IR (KBr)cm$^{-1}$: 3293, 1688, 1651, 1534, 1506, 1259, 1121, 1043, 748.

Example 75

N-(2-Amino-4-chlorophenyl)-4-[N-(pyridin-3-yl)methoxycarbonylaminomethyl]benzamide (Table 1: Compound 113)

mp: 167–170° C.; $^1$H NMR (270 MHz, DMSO-d$_6$) δ ppm: 4.28 (2H, d, J=5.9 Hz), 5.10 (2H, s), 5.21 (2H, s), 6.72 (1H, dd, J=2.2, 8.1 Hz), 6.81 (1H, d, J=2.2 Hz), 7.16 (1H, d, J=8.1 Hz), 7.37 (2H, d, J=8.1 Hz), 7.78 (1H, d, J=8.1 Hz), 7.92 (2H, d, J=8.1 Hz), 8.53 (1H, d, J=4.4 Hz), 8.59 (1H, s), 9.60 (1H, s); IR (KBr)cm$^{-1}$: 3347, 3062, 2931, 1653, 1576, 1505, 1456, 1428, 1301, 1232, 1114, 1070, 1019.

Example 76

N-(2-Aminophenyl)-4-[N-(5-methoxypridin-3-yl)methoxycarbonylaminomethyl]benzamide (Table 1: Compound 161)

mp: 169–170° C.; $^1$H NMR (270 MHz, DMSO-d$_6$) δ ppm: 3.83 (3H, s), 4.29 (2H, d, J=6.6 Hz), 4.87 (2H, s), 5.09 (2H, s), 6.57–6.62 (1H, m), 6.76–6.79 (1H, m), 6.94–6.99 (1H, m), 7.14–7.18 (1H, m), 7.36–7.39 (3H, m), 7.91–7.99 (3H, m), 8.19–8.30 (2H, m), 9.63 (1H, s); IR (KBr)cm$^{-1}$: 3330, 1694, 1633, 1524, 1457, 1298, 1269, 1045, 760.

Example 77

N-(2-Aminophenyl)-4-[N-(pyrazin-2-yl)methoxycarbonylaminomethyl]benzamide (Table 1: Compound 192)

mp: 182° C.; $^1$H NMR (270 MHz, DMSO-d$_6$) δ ppm: 4.30 (2H, d, J=6.6 Hz), 4.88 (2H, br.s), 5.20 (2H, s), 6.60 (1H, dd, J=7.3, 8.1 Hz), 6.78 (1H, d, J=8.1 Hz), 6.97 (1H, dd, J=6.6, 8.1 Hz), 7.16 (1H, d, J=7.3 Hz), 7.39 (2H, d, J=8.8 Hz), 7.94 (2H, d, J=8.8 Hz), 8.08 (1H, t-like, J=6.6 Hz), 8.61 (1H, s), 8.65 (1H, s), 8.68 (1H, s), 9.63 (1H, s); IR (KBr)cm$^{-1}$: 3266, 1709, 1632, 1535, 1508, 1284, 1055, 1022, 744.

Example 78

N-(2-Amino-5-methoxyphenyl)-4-[N-(pyridin-3-yl)methoxycarbonylaminomethyl]benzamide (Table 1: Compound 121)

mp: 141–143° C.; $^1$H NMR (270 MHz, DMSO-d$_6$) δ ppm: 3.66 (3H, s), 4.29 (2H, d, J=5.9 Hz), 4.51 (2H, br.s), 5.10 (2H, s), 6.63 (1H, dd, J=2.9, 8.8 Hz), 6.74 (1H, d, J=8.8 Hz), 6.91 (1H, d, J=2.2 Hz), 7.38 (2H, d, J=8.8 Hz), 7.41 (1H, s), 7.79 (1H, d, J=8.1 Hz), 7.92 (2H, d, J=8.1 Hz), 7.98 (1H, t, J=5.9 Hz), 8.54 (1H, d, J=3.7 Hz), 8.60 (1H, s), 9.65 (1H, s).

Example 79

N-(2-Aminophenyl)-4-[N-(pyridin-3-yl)methyl-N-(pyridin-3-yl)methoxycarbonylaminomethyl]benzamide (Table 1: Compound 109)

mp: (amorphous); $^1$H NMR (270 MHz, DMSO-d$_6$) δ ppm: 4.50 (2H, s), 4.56 (2H, s), 4.87 (2H, s ), 5.21 (2H, s), 6.60 (1H, t, J=7.7 Hz), 6.78 (1H, d, J=7.3 Hz), 6.97 (1H, d, J=7.3 Hz), 7.17 (1H, d, J=7.3 Hz), 7.20–7.5.0 (4H, m), 7.60–8.00 (4H, m), 8.40–8.60 (4H, m), 9.65 (1H, s); IR (KBr)cm$^{-1}$: 3268, 1700, 1504, 1246, 1120, 940, 714.

Example 80

N-(2-Aminophenyl)-4-[N-[3-(pyridin-3-yl)propyl]-N-(pyridin-3-yl)methoxycarbonylaminomethyl]benzamide (Table 1: Compound 120)

mp: (amorphous); $^1$H NMR (270 MHz, DMSO-d$_6$) δ ppm: 1.75–1.90 (2H, m), 2.48–2.62 (2H, m), 3.20–3.36 (2H, m), 4.55 (2H, s), 4.89 (2H, s), 5.16 (2H, s), 6.57–6.63 (1H, m), 6.76–6.80 (1H, m), 6.94–6.99 (1H, m), 7.14–7.17 (1H, m), 7.32–7.74 (6H, m), 7.94 (2H, d, J=8.1 Hz), 8.30–8.65 (4H, m), 9.64 (1H, s).

Example 81

N-(2-Hydroxyphenyl)-4-[N-(pyridin-3-yl)methyl-N-(pyridin-3-yl)methoxycarbonylaminomethyl]benzamide (Table 1: Compound 115)

mp: (amorphous); $^1$H NMR (270 MHz, DMSO-d$_6$) δ ppm: 4.52 (2H, s), 4.57 (2H, s), 5.20 (2H, s ), 6.84 (1H, t, J=6.6 Hz), 6.93 (1H, d, J=6.6 Hz), 7.03 (1H, d, J=7.3 Hz), 7.37 (4H, m), 7.68 (2H, dd, J=1.5, 8.1 Hz), 7.92 (2H, br.s), 8.53 (4H, m), 9.49 (1H, s ), 9.77 (1H, br.s); IR (KBr)cm$^{-1}$: 3035, 1698, 1243, 1118, 754, 640.

Example 82

N-(2-Hydroxyphenyl)-4-[N-(pyridin-3-yl)methoxycarbonylaminomethyl]benzamide (Table 1: Compound 111)

mp: 162–164° C.; $^1$H NMR (270 MHz, DMSO-d$_6$) δ ppm: 4.29 (1H, d, J=5.9 Hz), 5.10 (2H, s), 6.83 (1H, t, J=8.1 Hz), 6.92 (1H, d, J=6.6 Hz), 7.07 (1H, t, J=6.6 Hz), 7.39 (2H, d, J=8.8 Hz), 7.43 (1H, d, J=5.1 Hz), 7.68 (2H, d, J=8.1 Hz), 7.80 (1H, d, J=8.1 Hz), 7.92 (2H, d, J=8.1 Hz), 7.99 (1H, t, J=5.9 Hz), 8.54 (1H, d, J=4.4 Hz), 8.60 (1H, s), 9.49 (1H, s), 9.76 (1H, br.s); IR (KBr)cm$^{-1}$: 3333, 3259, 1694, 1645, 1529, 1267, 720.

Example 83

N-(2,4-Dihydroxyphenyl)-4-[N-(pyridin-3-yl)methoxycarbonylaminomethyl]benzamide (Table 1: Compound 116)

mp: (amorphous); $^1$H NMR (270 MHz, DMSO-d$_6$) δ ppm: 4.27 (2H, d, J=6.6 Hz), 5.10 (2H, s), 6.20 (2H, dd, J=2.2, 8.1 Hz), 6.39 (2H, d, J=2.9 Hz), 6.88 (2H, d, J=8.8 Hz), 7.33 (1H, d, J=8.1 Hz), 7.41 (1H, dd, J=5.1, 7.1 Hz), 7.89 (1H, d, J=8.8 Hz), 7.98 (1H, t, J=6.6 Hz), 8.05 (2H, s), 8.52 (1H, m), 8.59 (1H, s), 9.30 (2H, br.s); IR (KBr)cm$^{-1}$: 3387, 1702, 1612, 1311, 1169, 845.

Example 84

N-(2-Hydroxy-5-methylphenyl)-4-[N-(pyridin-3-yl) methoxycarbonylaminomethyl]benzamide (Table 1: Compound 118)

mp: 155–155.5° C.; $^1$H NMR (270 MHz, DMSO-d$_6$) δ ppm: 2.22 (3H, s), 4.29 (2H, d, J=5.8 Hz), 5.11 (2H, s), 6.82 (2H, m), 7.39 (2H, d, J=8.8 Hz), 7.42 (2H, m), 7.51 (1H, s), 7.79 (1H, d, J=8.1 Hz), 7.92 (1H, d, J=8.1 Hz), 7.98 (1H, t, J=5.9 Hz), 8.54 (1H, d, J=4.4 Hz), 8.60 (1H, s), 9.48 (2H, d, J=8.1 Hz); IR (KBr)cm$^{-1}$: 3306, 1723, 1655, 1525, 801, 639.

Example 85

N-(2-Hydroxy-5-methoxyphenyl)-4-[N-(pyridin-3-yl)methoxycarbonylaminomethyl]benzamide (Table 1: Compound 119)

mp: 175–176° C.; $^1$H NMR (270 MHz, DMSO-d$_6$) δ ppm: 3.69 (3H, s), 4.29 (2H, d, J=5.9 Hz), 5.10 (2H, s), 6.63 (1H, dd, J=2.9, 8.7 Hz), 6.84 (1H, d, J=8.8 Hz), 7.41 (4H, m), 7.79 (1H, d, J=8.1 Hz), 7.91 (1H, d, J=8.1 Hz), 7.99 (1H, t, J=5.9 Hz), 8.54 (1H, d, J=5.1 Hz), 8.60 (1H, s), 9.31 (1H, s), 9.45 (1H, s); IR (KBr)cm$^{-1}$: 3305, 1687, 1573, 1262, 1039, 868.

Example 86

N-(2-Aminophenyl)-4-[N-[2-(pyridin-3-yl) ethoxycarbonyl]amino]benzamide (Table 1: Compound 124)

mp: (amorphous); $^1$H NMR (270 MHz, DMSO-d$_6$) δ ppm: 3.00 (2H, t, J=6.6 Hz), 4.37 (2H, t, J=6.6 Hz), 4.87 (2H, br.s), 6.60 (1H, t, J=7.3 Hz), 6.97 (1H, t, J=7.3 Hz) 7.15 (1H, d, J=7.3 Hz), 7.36 (1H, dd, J=4.4, 8.1 Hz), 7.56 (2H, d, J=8.8 Hz), 7.92 (2H, d, J=8.8 Hz), 8.46 (1H, d, J=4.4 Hz), 8.54 (1H, d, J=2.2 Hz), 9.95 (1H, s); IR (KBr)cm$^{-1}$: 3285, 1695, 1519, 1315, 1233, 1079.

Example 87

N-(2-Aminophenyl)-5-[(pyridin-3-yl) methoxycarbonyl]aminobenzofuran-2-carboxyamide (Table 3: Compound 2)

mp: 173–174° C.; $^1$H NMR (270 MHz, DMSO-d$_6$) δ ppm: 5.22 (2H, s), 6.60 (1H, dd, J=8.1, 8 Hz), 6.79 (1H, dd, J=1.5, 8.1 Hz), 7.00 (1H, dd, J=8.1, 8 Hz), 7.20 (1H, dd, J=1.5, 8.1 Hz), 7.44 (1H, m), 7.48 (1H, dd, J=1.5, 8.8 Hz), 7.61 (1H, d, J=8.8 Hz), 7.67 (1H, s), 7.88 (1H, dd, J=1.5, 8 Hz), 7.96 (1H, d, J=1.5 Hz), 8.56 (1H, dd, J=1.5, 4.8 Hz), 8.68 (1H, d, J=1.5 Hz), 9.83 (1H, s), 9.91 (1H, s); IR (KBr)cm$^{-1}$: 3308, 1707, 1667, 1584, 1536, 1452, 1316, 1248, 1157, 1128, 1070, 955, 879, 795, 748, 710.

Example 88

Preparation of N-(2-Aminophenyl)-4-[N-(pyridin-3-yl)methoxythiocarbonylaminomethyl]benzamide (Table 1: Compound 86)

(88-1) To a solution of 20 mg of 3-pyridine methanol (0.18 mmol) in 5 mL of dry THF were added 30 mg of N,N'-thiocarbonyldiimidazole (0.16 mmol) at room temperature. After stirring overnight, to the mixture were added 50 mg of the compound from Example 1, the process (1-4) (0.14 mmol).

After leaving at room temperature overnight, to the solution was added 100 mL of chloroform, and the solution was washed with water (3×20 mL) and then saturated brine, and dried over anhydrous magnesium sulfate. After evaporation, the residue was purified by column chromatography on silica gel (eluent: chloroform:methanol=30:1) to give 70 mg of N-[2-(N-tert-butoxycarbonyl)aminophenyl]-4-[N-(pyridin-3-yl)methoxythiocarbonylaminomethyl]benzamide (Yield: 88%) as amorphous.

$^1$H NMR (270 MHz, DMSO-d$_6$) δ ppm: 1.45 (9H, s), 4.73 (2H, d, J=5.9 Hz), 5.52 (2H, s), 6.73–7.33 (3H, m), 7.35–7.43 (2H, m), 7.58–7.95 (5H, m), 8.14–8.65 (3H, m), 9.80 (1H, s), 9.91 (1H, t).

(88-2) To a solution of 50 mg of the compound from the process (88-1) (0.10 mmol) in 3 mL of methanol was added 3 mL of 4N hydrochloric acid-dioxane, and the mixture was stirred at room temperature for 1.5 hours. The mixture was poured into diluted sodium hydroxide aq. to neutralize the residual hydrochloric acid, and then was extracted with chloroform (3×10 mL). The organic layer was washed twice with saturated brine, dried over anhydrous magnesium sulfate and concentrated to give 34 mg of N-(2-Aminophenyl)-4-[N-(pyridin-3-yl)methoxythiocarbonylaminomethyl] benzamide (Yield: 87%).

mp: 154–156° C. (dec.); $^1$H NMR (270 MHz, DMSO-d$_6$) δ ppm: 4.73 (2H, d, J=5.9 Hz), 4.88 (2H, s), 5.52 (2H, s), 6.60 (1H, t, J=7.3 Hz), 6.77 (1H, d, J=8.1 Hz), 6.96 (1H, t, J=8.1 Hz), 7.16 (1H, d, J=7.3 Hz), 7.29–7.41 (3H, m), 7.83–7.95 (3H, m), 8.50–8.56 (1H, m), 8.65 (1H, s), 9.62 (1H, s), 9.93 (1H, s); IR (KBr)cm$^{-1}$: 3204, 3035, 1631, 1523, 1456, 1289, 1191, 920, 753.

Example 89

Preparation of N-(2-Aminophenyl)-4-[N'-(pyridin-3-ylmethyl)ureidomethyl]benzamide (Table 1: Compound 88)

(89-1) To a solution of 0.28 g of 3-picolylamine (2.6 mmol) in 10 mL of THF was added 0.42 g of N,N'-carbonyldiimidazole (2.4 mmol) at room temperature, and the mixture was stirred for an hour. To the solution was added 0.58 g of the compound from Example 1, the process (1-4) (1.8 mmol) at room temperature, and the solution was stirred for 3 hours and then left overnight.

After diluting with water, the mixture was extracted with ethyl acetate. The organic layer was washed with saturated brine, dried and evaporated. The residue was purified by column chromatography on silica gel (eluent: ethyl acetate:methanol=10:1) to give 0.77 g of N-[2-(N-tert-butoxycarbonyl)amino]phenyl-4-[N'-(pyridin-3-ylmethyl)ureidomethyl]benzamide (Yield: 90%) as a white amorphous solid.

$^1$H NMR (270 MHz, CDCl$_3$) δ ppm: 1.46 (9H, s), 4.20 (2H, d, J=5.1 Hz), 4.28 (2H, d, J=4.3 Hz), 6.10–6.30 (2H, m), 7.00–7.25 (4H, m), 7.33 (1H, d, J=7.3 Hz), 7.49–7.54 (2H, m), 7.58–7.64 (3H, m), 7.75 (1H, s), 8.28 (1H, br.s), 8.39 (1H, d, J=5.1 Hz), 9.65 (1H, br.s).

(89-2) To a solution of 0.63 g of the compound from the process (89-1) (1.32 mmol) in 4 mL of dioxane and 2 mL of methanol was added 4 mL of 4N hydrochloride-dioxane, and the mixture was stirred at room temperature for 2 hours. After adding saturated sodium bicarbonate aq., the mixture was extracted with ethyl acetate-methyl ethyl ketone. The organic layer was washed with saturated brine, dried and evaporated. The residue was washed with diisopropyl ether to give 0.37 g of N-(2-aminophenyl)-4-[N'-(pyridin-3-ylmethyl)ureidomethyl]benzamide (Yield: 74.7%) as a brown solid.

mp: 167–175° C.; $^1$H NMR (270 MHz, DMSO-d$_6$) δ ppm: 4.27 (2H, d, J=5.9 Hz), 4.31 (2H, d, J=5.9 Hz), 4.89 (2H, br.s), 6.57–6.63 (3H, m), 6.78 (1H, d, J=8.1 Hz), 6.97 (1H, dd, J=7.3, 8.1 Hz), 7.17 (1H, d, J=7.3 Hz), 7.32–7.38 (3H, m), 7.66 (1H, d, J=8.1 Hz), 7.93 (2H, d, J=8.1 Hz), 8.44 (1H, d, J=5.1 Hz); IR (KBr)cm$^{-1}$: 3344, 3241, 1645, 1560, 1527, 1505, 1283, 751, 708.

As described in Example 89, the compounds of Examples 90 to 95 were prepared, each of whose melting point (mp), $^1$H NMR data and/or IR data are shown below.

Example 90

N-(2-Aminophenyl)-4-[N'-(3-aminophenyl)ureidomethyl]benzamide (Table 1: Compound 24)

mp: 206–208° C. (dec.); $^1$H NMR (270 MHz, DMSO-d$_6$) δ ppm: 4.35 (2H, d, J=5.9 Hz), 4.93 (4H, br.s), 6.13 (1H, d, J=7.3 Hz), 6.51–6.62 (3H, m), 6.74–6.98 (3H, m), 7.12–7.18 (1H, m), 7.41 (2H, d, J=8.1 Hz), 7.94 (2H, d, J=8.1 Hz), 8.28 (1H, s), 9.61 (1H, s); IR (KBr)cm$^{-1}$: 3356, 3269, 1640, 1555, 1495, 1458, 1308, 1236, 753.

Example 91

N-(2-Aminophenyl)-4-[N'-(pyridin-3-yl)ureidomethyl]benzamide (Table 1: Compound 87)

mp: 187–190° C.; $^1$H NMR (270 MHz, DMSO-d$_6$) δ ppm: 4.39 (2H, d, J=5.9 Hz), 4.89 (2H, br.s), 6.59 (1H, d, J=77.3, 7.3 Hz), 6.77 (1H, d, J=6.6 Hz), 6.88 (1H, t, J=5.9 Hz), 6.97 (1H, ddd, J=1.5, 6.6, 7.3 Hz), 7.16 (1H, d, J=8.1 Hz), 7.26 (1H, dd, J=4.4, 8.1 Hz), 7.42 (2H, d, J=8.8 Hz), 7.95 (2H, d, J=8.1 Hz), 7.89–7.96 (1H, m), 8.12 (1H, dd, J=1.5, 4.4 Hz), 8.56 (1H, d, J=3.0 Hz), 8.85 (1H, s), 9.62 (1H, s); IR (KBr)cm$^{-1}$: 3248, 1663, 1541, 1423, 1280, 1054.

Example 92

N-(2-Aminophenyl)-4-[N'-(3-aminophenyl)thioureidomethyl]benzamide (Table 1: Compound 25)

mp: 123° C. (dec.); $^1$H NMR (270 MHz, DMSO-d$_6$) δ ppm: 4.80 (2H, d, J=5.1 Hz), 4.87 (2H, s), 5.12 (2H, s), 6.36 (1H, dd, J=1.5, 8.1 Hz), 6.48–6.63 (3H, m), 6.78 (1H, d, J=6.6 Hz), 6.94–7.00 (2H, m), 7.17 (1H, d, J=8.1 Hz), 7.42 (2H, d, J=8.1 Hz), 7.92–8.01 (3H, m), 9.46 (1H, s), 9.61 (1H, s); IR (KBr)cm$^{-1}$: 3335, 1616, 1528, 1503, 1456, 1311, 864, 751.

Example 93

N-(2-Aminophenyl)-4-[N'-(3-nitrophenyl)thioureidomethyl]benzamide (Table 1: Compound 20)

mp: 160° C. (dec.); $^1$H NMR (270 MHz, DMSO-d$_6$) δ ppm: 4.87 (2H, d, J=5.1 Hz), 7.27–7.33 (3H, m), 7.46–7.63 (5H, m), 7.89–7.95 (2H, m), 8.05 (2H, d, J=8.1 Hz), 8.70 (1H, s), 8.84 (1H, t, J=8.9 Hz), 10.37 (1H, s).

Example 94

N-(2-Amino-5-fluorophenyl)-4-[N'-(pyridin-3-yl)methylureidomethyl]benzamide (Table 1: Compound 112)

mp: (amorphous); $^1$H NMR (270 MHz, DMSO-d$_6$) δ ppm: 4.77 (4H, d, J=5.1 Hz), 4.85 (2H, s), 6.81 (2H, m), 7.16 (1H, dd, J=2.9, 10.3 Hz), 7.39 (1H, dd, J=5.1, 8.1 Hz), 7.53 (2H, d, J=8.1 Hz), 7.81 (1H, d, J=8.1 Hz), 7.93 (2H, d, J=8.1 Hz), 8.51 (1H, dd, J=1.5, 5.1 Hz), 8.62 (1H, d, J=1.5 Hz), 9.66 (1H, s); IR (KBr)cm$^{-1}$: 3399, 1730, 1638, 1508, 1444, 1411.

Example 95

N-(2-Hydroxyphenyl)-4-[N'-(pyridin-3-yl)methylureidomethyl]benzamide (Table 1: Compound 114)

mp: (amorphous); $^1$H NMR (270 MHz, DMSO-d$_6$) δ ppm: 4.43 (2H, d, J=6.6 Hz), 4.69 (2H, s), 6.83 (1H, t, J=6.6 Hz), 6.91 (1H, d, J=8.1 Hz), 7.68 (1H, d, J=6.6 Hz), 7.82 (2H, d, J=88.1 Hz), 8.21 (1H, d, J=4.4 Hz), 8.35 (1H, d, J=2.2 Hz), 8.81 (1H, t, J=6.6 Hz), 9.48 (1H, s), 9.75 (1H, s); IR (KBr)cm$^{-1}$: 3399, 1664, 1535, 1236, 1064.

Example 96

Preparation of N-(2-Aminophenyl)-4-[2-[N-(pyridin-3-yl)acetylamino]ethyl]benzamide (Table 1: Compound 77)

(96-1) To a suspension of 3.40 g of terephthalaldehydic acid (22.6 mmol) in 25 mL of toluene was added 4 mL of thionyl chloride, and the mixture was heated with stirring at 80° C. for 2 hours. After cooling and evaporation, the residue was dissolved in 50 mL of THF to give a solution of the acid chloride. To a solution of 4.16 g of the compound from Example 1, the process (1-2) (20.0 mmol) in 10 mL of THF was added 6 mL of triethylamine (42.8 mmol) and then the above solution of the acid chloride was added dropwise under ice-cooling over 30 min.

After stirring for 5 hours, to the mixture was added saturated sodium bicarbonate aq., and the mixture was extracted with ethyl acetate. The organic layer was washed with saturated brine, dried and evaporated. The residue was purified by column chromatography on silica gel (gradient elution with chloroform to chloroform:ethyl acetate=10:1) to give 3.42 g of N-[2-(N-tert-butoxycarbonyl)aminophenyl]-4-formylbenzamide (Yield: 50.2%) as a light brown solid.

$^1$H NMR (270 MHz, CDCl$_3$) δ ppm: 1.52 (9H, s), 6.77 (1H, br.s), 7.16–7.18 (2H, m), 7.23–7.26 (1H, m), 7.88 (1H, d, J=8.8 Hz), 7.98 (2H, d, J=8.8 Hz), 8.13 (2H, d, J=8.8 Hz), 9.57 (1H, br.s), 10.11 (1H, br.s); IR (KBr)cm$^{-1}$: 3326, 3251, 1707, 1696, 1659, 1603, 1165.

(96-2) A suspension of 3.0 g of the compound from the process (96-1) (8.82 mmol) and 4.5 g of ethoxycarbonylmethyl triphenylphosphine (12.9 mmol) in 10 mL of toluene was stirred in a stream of nitrogen at 80° C. for 5.5 hours. After cooling, the mixture was diluted with ethyl acetate; washed with saturated sodium bicarbonate, water and saturated brine; dried; and evaporated. The residue was purified by column chromatography on silica gel (eluent: chloroform:ethyl acetate=20:1) to give 3.3 g of ethyl 4-[N-[2-[N-tert-butoxycarbonyl)aminophenyl]aminocarbonyl]cinnamate (Yield: 91.1%) as a yellow amorphous solid.

$^1$H NMR (270 MHz, CDCl$_3$) δ ppm: 1.35 (3H, t, J=7.3 Hz), 1.52 (9H, s), 4.28 (2H, q, J=7.3 Hz), 6.52 (1H, d, J=15.1 Hz), 6.80 (1H, br.s), 7.16–7.25 (3H, m), 7.61 (2H, d, J=8.1 Hz), 7.71 (1H, d, J=15.1 Hz), 7.82 (1H, d, 7.3 Hz), 7.98 (2H, d, J=8.1 Hz), 9.34 (1H, br.s).

(96-3) To a solution of 2.50 g of the compound from the process (96-2) (6.09 mmol) in 30 mL of THF and 40 mL of methanol was added 10% Pd/C (wet, 0.5 g) in a stream of nitrogen, and then stirred in a stream of hydrogen for 30 min. After filling with nitrogen, the mixture was filtered to remove the catalyst, and the filtrate was evaporated. To the residue was added diisopropyl ether, and the precipitated solid was collected by filtration and dried to give 2.23 g of N-[2-(N-tert-butoxycarbonyl)aminophenyl]-4-(2-ethoxycarbonylethyl)benzamide (Yield: 88.8%) as a white solid.

$^1$H NMR (270 MHz, CDCl$_3$) δ ppm: 1.25 (3H, t, J=7.3 Hz), 1.52 (9H, s), 2.65 (2H, t, J=7.3 Hz), 3.02 (2H, t, J=7.3 Hz), 4.13 (2H, q, J=7.3 Hz), 6.77 (1H, br.s), 7.16–7.33 (5H, m), 7.78 (1H, d, J=8.1 Hz), 7.89 (2H, d, J=8.8 Hz), 9.06 (1H, br.s).

(96-4) To a suspension of 2.21 g of the compound from the process (96-3) (5.36 mmol) in 10 mL of methanol and 15 mL of water was added 0.37 g of lithium hydroxide monohydrate (8.82 mmol), and the mixture was stirred at 40° C. for 3 hours. After cooling, to the mixture was added 10% hydrochloric acid and the mixture was extracted with ethyl acetate. The organic layer was washed with saturated brine, dried and evaporated. To the residue was added diisopropyl ether, and the precipitated solid was filtered and dried to give 1.87 g of N-[2-(N-tert-butoxycarbonyl)aminophenyl]-4-(2-carboxyethyl)benzamide (Yield: 90.8%) as a white solid.

$^1$H NMR (270 MHz, DMSO-d$_6$) δ ppm: 1.45 (9H, s), 2.59 (2H, t, J=7.3 Hz), 2.91 (2H, t, J=7.3 Hz), 7.13–7.20 (2H, m), 7.40 (2H, d, J=8.1 Hz), 7.54 (2H, dd, J=7.3, 2.1 Hz), 7.88 (2H, d, J=8.1 Hz), 8.66 (1H, br.s), 9.79 (1H, br.s).

(96-5) To a suspension of 0.12 g of the compound from the process (96-4) (0.3 mmol) in 5 mL of benzene were added 0.1 mL of triethylamine (0.7 mmol) and 0.3 g of molecular sieves 4A, and the mixture was stirred in a stream of nitrogen for 0.5 hours. To the mixture was added 0.15 mL of diphenylphosphoryl azide (0.7 mmol), and the mixture was refluxed with heating for 2 hours. After cooling, to the mixture was added 0.4 mL of benzyl alcohol (3.8 mmol), and the mixture was refluxed with heating for additional 2.5 hours. After diluting with ethyl acetate, the reaction mixture was washed with water and saturated brine.

The organic layer was dried and evaporated. The residue was purified by column chromatography on silica gel (eluent: chloroform:ethyl acetate 4:1) to give 129 mg of N-[2-(N-tert-butoxycarbonyl)aminophenyl]-4-[2-(N-benzyloxycarbonylamino)ethyl]benzamide (Yield: 88%) as a clear oil.

$^1$H NMR (270 MHz, CDCl$_3$) δ ppm: 1.51 (9H, s), 2.89 (2H, t, J=7.3 Hz), 3.45–3.54 (2H, m), 4.80 (1H, m), 5.10 (2H, s), 6.76 (1H, br.s), 7.20–7.38 (10H, m), 7.79 (1H, d, J=8.8 Hz), 7.89 (2H, d, J=8.1 Hz), 9.10 (1H, br.s).

(96-6) To a solution of 129 mg of the compound from the process (96-5) (0.26 mmol) in 10 mL of methanol was added 10% Pd/C (wet, 0.05 g) in a stream of nitrogen, and then stirred in a hydrogen stream for 2 hours. After removing the catalyst, the filtrate was evaporated and dried. The residue was dissolved in 5 mL of dichloromethane. To the solution were added 0.18 g of 3-pyridineacetic acid hydrochloride (1.04 mmol) and then 0.28 g of triethylamine (2.0 mmol), and the mixture was ice-cooled. Under ice-cooling, to the mixture was added 0.17 g of 2-chloro-1,3-dimethylimidazolinium chloride (1.0 mmol), and the mixture was stirred for 2 hours. To the mixture was added saturated sodium bicarbonate aq., and the mixture was extracted with chloroform. The organic layer was washed with saturated brine, dried and evaporated. The residue was purified by column chromatography on silica gel (eluent: ethyl acetate:methanol=10:1) to give 50 mg of N-[2-(N-tert-butoxycarbonyl)aminophenyl]-4-[2-[N-(pyridin-3-yl)acetylamino]ethyl]benzamide (Yield: 40%) as a colorless oil.

$^1$H NMR (270 MHz, CDCl$_3$) δ ppm: 1.48 (9H, s), 2.80 (2H, t, J=6.6 Hz), 3.42 (2H, m), 3.52 (2H, s), 6.33 (1H, t-like, J=5.9 Hz), 7.09 (2H, d, J=8.1 Hz), 7.14–7.20 (2H, m), 7.24 (1H, dd, J=4.4, 7.3 Hz), 7.41 (1H, dd, J=3.7, 5.9 Hz), 7.50 (1H, s), 7.58 (1H, dd, J=1.5, 5.9 Hz), 7.69 (1H, dd, J=3.7, 5.9 Hz), 7.75 (2H, d, J=8.1 Hz), 8.22 (1H, d, J=2.1 Hz), 8.44 (1H, dd, J=1.5, 4.4 Hz), 9.49 (1H, br.s).

(96-7) To a solution of 50 mg of the compound from the process (96-6) (0.10 mmol) in 2 mL of dioxane and 1 mL of methanol was added 2 mL of 4N hydrochloric acid-dioxane, and the mixture was stirred at room temperature for 2.5 hours. To the mixture was added saturated sodium bicarbonate, and the mixture was extracted with ethyl acetate. The organic layer was washed with saturated brine, dried and evaporated. The residue was dried to give 22 mg of N-(2-aminophenyl)-4-[2-[N-(pyridin-3-yl)acetylamino]ethyl]benzamide (Yield: 59%) as an amorphous solid.

mp: (amorphous); $^1$H NMR (270 MHz, DMSO-d$_6$) δ ppm: 2.70–2.90 (4H, m), 3.42 (2H, s), 4.89 (2H, br.s), 6.60 (1H, dd, J=7.3, 7.3 Hz), 6.78 (1H, d, J=7.3 Hz), 6.97 (1H, dd, J=7.3, 7.3 Hz), 7.16 (1H, d, J=7.3 Hz), 7.29–7.32 (3H, m), 7.59 (1H, d, J=8.1 Hz), 7.89 (1H, d, J=8.1 Hz), 8.22 (1H, t-like), 8.41–8.43 (2H, m), 9.62 (1H, br.s).

Example 97

Preparation of N-(2-Aminophenyl)-4-[2-[N-(3-picolyl)aminocarbonyl]ethyl]benzamide (Table 1: Compound 80)

(97-1) To a suspension of 0.58 g of the compound from Example 96, the process (96-4) (1.5 mmol) in 5 mL of dichloromethane were added 0.22 g of 3-picolylamine (2.0 mmol) and 0.56 mL of triethylamine (4.0 mmol). Under ice-cooling, to the mixture was added 0.39 g of 2-chloro-1,3-dimethylimidazolinium chloride (2.0 mmol) in 5 mL of dichloromethane, and the mixture was stirred for 1.5 hours. To the mixture was added saturated sodium bicarbonate aq., and the mixture was extracted with chloroform.

The organic layer was washed with water and saturated brine, dried and evaporated. The residue was purified by column chromatography on silica gel (eluent: chloroform:methanol:NH$_3$ aq.=100:10:1) to give 0.71 g of N-[2-(N-tert-butoxycarbonyl)aminophenyl]-4-[2-[N-(3-picolyl)aminocarbonyl]ethyl]benzamide (Yield: 94%) as a light brown oil.

$^1$H NMR (270 MHz, CDCl$_3$) δ ppm: 1.45 (9H, s), 2.42 (2H, t, J=7.3 Hz), 2.98 (2H, t, J=7.3 Hz), 4.32 (2H, d, J=6.6 Hz), 6.44 (1H, t, J=6.6 Hz), 7.14–7.27 (5H, m), 7.48–7.57 (3H, m), 7.63–7.68 (3H, m), 7.90 (1H, d, J=2.1 Hz), 8.43 (1H, dd, J=1.4, 4.4 Hz), 9.86 (1H, br.s).

(97-2) To a solution of 0.70 g of the compound from the process (97-1) (1.47 mmol) in 5 mL of dioxane was added 5 mL of 4N hydrochloride-dioxane and then 2 mL of methanol, and the mixture was stirred at room temperature for 2 hours. To the mixture was added saturated sodium bicarbonate aq., and the mixture was extracted with ethyl acetate. The organic layer was washed with saturated brine, dried and evaporated. To the residue was added diisopropyl ether, and the precipitated solid was collected by filtration and dried to give 0.42 g of N-(2-aminophenyl)-4-[2-[N-(3-picolyl)aminocarbonyl]ethyl]benzamide (Yield: 76.3%) as an opalescent solid.

mp: 168–170° C.; $^1$H NMR (270 MHz, DMSO-d$_6$) δ ppm: 2.47–2.53 (2H, m), 2.93 (2H, t, J=7.3 Hz), 4.27 (2H, d, J=5.9

Hz), 4.90 (2H, br.s), 6.60 (1H, dd, J=7.3, 7.3 Hz), 6.78 (1H, d, J=8.1 Hz), 6.97 (1H, dd, J=6.6, 7.3 Hz), 7.16 (1H, d, J=6.6 Hz), 7.28–7.35 (1H, m), 7.33 (2H, d, J=8.1 Hz), 7.49 (1H, dd, J=2.1, 5.9 Hz), 7.89 (2H, d, J=8.1 Hz), 8.39–8.44 (3H, m), 9.62 (1H, br.s); IR (KBr)cm$^{-1}$: 3313, 1641, 1523, 1457, 1300, 748, 713.

Example 98

Preparation of N-(2-Aminophenyl)-4-[(pyridin-3-yl)methylaminocarbonyloxymethyl]benzamide (Table 1: Compound 85)

(98-1) To a solution of 1.99 g of methyl 4-hydroxymethylbenzoate (12.0 mmol) in 20 mL of THF were added 1.78 g of N,N'-carbonyldiimidazole (11.0 mmol) at room temperature, and the solution was stirred for an hour. To the solution were added 1.08 g of 3-picolylamine (10.0 mmol) at room temperature, and the mixture was stirred for 3.5 hours and left overnight. Water was added to the solution, and the mixture was extracted with ethyl acetate.

The organic layer was washed with saturated brine, dried and evaporated. The residue was purified by column chromatography on silica gel (eluent: ethyl acetate) to give 2.76 g of N-(4-methoxycarbonyl)benzyloxycarbonyl-3-picolylamine (Yield: 91.9%) as a white waxy solid.

$^1$H NMR (270 MHz, CDCl$_3$) δ ppm: 3.91 (3H, s), 4.40 (2H, d, J=5.9 Hz), 5.18 (2H, s), 5.50 (1H, br.s), 7.24–7.28 (1H, m), 7.40 (2H, d, J=8.1 Hz), 7.65 (1H, d, J=7.3 Hz), 8.02 (2H, d, J=8.8 Hz), 8.50–8.53 (2H, m).

(98-2) To a suspension of 2.40 g of the compound from the process (98-1) (8.0 mmol) in 10 mL of methanol and 20 mL of water was added 0.42 g of lithium hydroxide monohydrate (10.0 mmol), and the mixture was stirred at room temperature for 5 hours. To the reaction mixture was added 10% hydrochloric acid to acidified to pH 2 to 4, and the precipitated solid was collected by filtration and dried to give 1.83 g of N-(4-carboxy)benzyloxycarbonyl-3-picolylamine (79.9%) as a white solid.

$^1$H NMR (270 MHz, DMSO-d$_6$) δ ppm: 4.24 (2H, d, J=5.9 Hz), 5.13 (2H, s), 7.33–7.38 (1H, m), 7.46 (2H, d, J=8.1 Hz), 7.94 (2H, d, J=8.1 Hz), 7.95–8.01 (1H, m), 8.46 (1H, d, J=5.1 Hz), 8.49 (1H, d, J=1.5 Hz), 13.0 (1H, br.s).

(98-3) To a suspension of 1.26 g of the compound from the process (98-2) (4.4 mmol) in 20 mL of dichloromethane were slowly added 1.0 mL of oxalyl chloride (11.4 mmol) and then several drops of DMF. The reaction mixture was stirred at room temperature for 10 min. and at 40° C. for additional 30 min. After cooling, the mixture was evaporated and the excess oxalyl chloride was removed by evaporation with toluene. To the residue was added 10 mL of dichloromethane. Under ice-cooling, to the mixture was added dropwise a solution of 0.83 g of the compound from Example 1, the process (1-2) (4.0 mmol) in 8 mL of dichloromethane and 8 mL of pyridine, and the solution was warmed to room temperature with stirring for 7 hours and left overnight.

To the mixture was added saturated sodium bicarbonate, and the mixture was extracted with chloroform. The organic layer was washed with saturated brine, dried and evaporated. Toluene was added to the residue to azeotropically remove the excess pyridine. The residue was purified by column chromatography on silica gel (eluent: ethyl acetate) to give 1.40 g of N-[2-(N-tert-butoxycarbonyl)aminophenyl]-4-[(pyridin-3-yl)methylaminocarbonyloxymethyl]benzamide (Yield: 73.4%) as a light brown solid.

$^1$H NMR (270MHz, CDCl$_3$) δ ppm: 1.51 (9H, s), 4.40 (2H, d, J=5.9 Hz), 5.19 (2H, s), 5.56 (1H, m), 7.07 (1H, br.s), 7.14–7.31 (4H, s), 7.43 (2H, d, J=8.1 Hz), 7.65 (1H, d, J=8.1 Hz), 7.76 (1H, d, J=7.3 Hz), 7.95 (2H, d, J=8.1 Hz), 8.52 (2H, d, J=4.1 Hz), 9.32 (1H, br.s).

(98-4) To a solution of 1.00 g of the compound from the process (98-3) (2.10 mmol) in 10 mL of dioxane and 2 mL of methanol was added 9 mL of 4N hydrochloric acid-dioxane at room temperature, and the mixture was stirred for 2 hours. To the mixture was added saturated sodium bicarbonate and the mixture was extracted with ethyl acetate-methyl ethyl ketone (1:1). The organic layer was washed with saturated brine, dried and evaporated. To the residue was added methanol-diisopropyl ether, and the precipitated solid was collected by filtration and dried to give 0.79 g of N-(2-aminophenyl)-4-[(pyridin-3-yl)methylaminocarbonyloxymethyl]benzamide (Yield: quantitative) as a white solid.

mp: 139–141° C.; $^1$H NMR (270 MHz, DMSO-d$_6$) δ ppm: 4.25 (2H, d, J=5.9 Hz), 4.90 (2H, s), 5.13 (2H, s), 6.60 (1H, dd, J=6.6, 7.3 Hz), 6.78 (1H, d, J=7.3 Hz), 6.97 (1H, dd, J=6.6, 7.3 Hz), 7.17 (1H, d, J=7.3 Hz), 7.36 (1H, dd, J=4.4, 8.1 Hz), 7.47 (2H, d, J=8.1 Hz), 7.67 (1H, d, J=8.1 Hz), 7.97 (2H, d, J=7.3 Hz), 7.90–8.00 (1H, m), 8.46 (1H, dd, J=1.5, 5.1 Hz), 8.49 (1H, d, J=2.1 Hz), 9.65 (1H, br.s); IR (KBr) cm$^{-1}$: 3326 (br.), 1694, 1637, 1526, 1458, 1147, 750, 712.

Example 99

Preparation of N-(2-Aminophenyl)-4-[3-(imidazol-1-yl)propylaminocarbonyloxymethyl]benzamide (Table 1: Compound 215)

The title compound was prepared as described in Example 98.

mp: (amorphous); $^1$H NMR (270 MHz, DMSO-d$_6$) δ ppm: 1.80–1.89 (2H, m), 2.94–3.02 (2H, m), 3.98 (2H, t, J=7.3 Hz), 4.88 (2H, s), 5.11 (2H, s), 6.55–6.63 (1H, m), 6.76–6.97 (3H, m), 7.10–7.18 (2H, m), 7.43–7.48 (3H, m), 7.61 (1H, s), 7.98 (2H, d, J=8.1 Hz), 9.66 (1H, s).

Example 100

Preparation of N-(2-Aminophenyl)-4-(phenylacetylamino)benzamide (Table 1: Compound 22)

(100-1) To a solution of 16.6 g of the compound from Example 1, the process (1-2) (80 mmol) in 120 mL of dichloromethane was added 16.8 mL of triethylamine (120 mmol) and then, was slowly added a solution of 16.0 g of 4-nitrobenzoyl chloride (86.4 mmol) in 40 mL of dichloromethane, and the solution was stirred for 7 hours. To the solution, was added saturated sodium bicarbonate aq., and the mixture was extracted with chloroform.

The organic layer was washed with 1N hydrochloric acid, saturated sodium bicarbonate and saturated brine; dried; and evaporated. The residue was washed with diisopropyl ether to give 28.0 g of N-[2-(N-tert-butoxycarbonylamino)phenyl]-4-nitrobenzamide (Yield: 98%) as a light yellow solid.

$^1$H NMR (270 MHz, CDCl$_3$) δ ppm: 1.53 (9H, s), 7.17–7.29 (4H, m), 7.85 (1H, br.d, J=7.3 Hz), 8.17 (2H, d, J=8.8 Hz), 8.32 (2H, d, J=8.8 Hz), 9.88 (1H, br.s).

(100-2) To a solution of 24.0 g of the compound from the process. (100-1) (67.2 mmol) in 80 mL of THF and 80 mL of methanol was added 2.4 g of 10% Pd/C (wet) in a stream of nitrogen, and the mixture was stirred in a stream of hydrogen for 1.5 hours. After cease of absorption of hydrogen, the catalyst was removed by filtration and the filtrate was evaporated. To the residue were added diisopropyl ether and ethyl acetate, and the precipitated solid was collected by filtration and dried to give 18.96 g of N-[2-(N-tert-butoxycarbonylamino)phenyl]-4-aminobenzamide (Yield: 86%) as a white solid.

$^1$H NMR (270 MHz, DMSO-d$_6$) δ ppm: 1.46 (9H, s), 5.84 (2H, s), 6.61 (2H, d, J=8.8 Hz), 7.10–7.18 (2H, m), 7.46–7.55 (2H, m), 7.68 (2H, d, J=8.8 Hz), 8.67 (1H, s), 9.49 (1H, s).

(100-3) To a solution of 1.6 g of the compound from the process (100-2) (4.88 mmol) in 15 mL of dichloromethane were added 0.8 mL of pyridine (9.9 mmol) and 0.96 mL of phenylacetyl chloride (7.26 mmol), and the solution was stirred for one day. After completion of the reaction, water was added and the precipitated crystals were collected by filtration to give 1.66 g of N-[2-(N-tert-butoxycarbonylamino)phenyl]-4-(phenylacetylamino)benzamide (Yield: 76%).

(100-4) To a solution of 1 g of the compound from the process (100-3) (2.24 mmol) in 25 mL of acetonitrile was added 0.88 mL of iodotrimethylsilane (6.18 mmol) at room temperature, and the solution was stirred for 3 hours. After completion of the reaction, the solution was concentrated. The residue was recrystallized from methanol to give 0.29 g of N-(2-aminophenyl)-4-(phenylacetylamino)benzamide (Yield: 38%) as white crystals.

mp: 232–237° C.; $^1$H NMR (270 MHz, DMSO-d$_6$) δ ppm: 3.69 (2H, s), 4.90 (2H, s), 6.60 (1H, t, J=7.3 Hz), 6.77 (1H, d, J=7.3 Hz), 6.96 (1H, t, J=7.3 Hz), 7.15 (1H, d, J=7.4 Hz), 7.22–7.35 (5H, m), 7.72 (2H, d, J=8.8 Hz), 7.95 (2H, d, J=8.8 Hz), 9.57 (1H, s), 10.43 (1H, s); IR (KBr)cm$^{-1}$: 2937, 2764, 1660, 1598, 1506, 1459.

As described in Example 100, the compounds of Examples 101 to 128 were prepared, each of whose melting point (mp), $^1$H NMR data and/or IR data are shown below.

Example 101

N-(2-Aminophenyl)-4-[(4-phenylbutanoyl)amino]benzamide (Table 1: Compound 4)

mp: (amorphous); $^1$H NMR (270 MHz, DMSO-d$_6$) δ ppm: 1.91 (2H, hep, J=7.3 Hz), 2.37 (2H, t, J=7.3 Hz), 2.64 (2H, t, J=7.3 Hz), 5.0 (2H, br.s), 6.61 (1H, t, 7.0 Hz), 6.79 (1H, dd, J=1.5, 8.1 Hz), 6.97 (1H, t, J=77.0 Hz), 7.10–7.40 (6H, m), 7.71 (2H, d, J=8.8 Hz), 7.94 (2H, d, J=8.8 Hz), 9.57 (1H, s), 10.15 (1H, s); IR (KBr)cm$^{-1}$: 3344, 1687, 1603, 1542, 1460, 1315, 1033, 842, 737.

Example 102

N-(2-Aminophenyl)-4-[(4-chlorophenylacetyl)amino]benzamide (Table 1: Compound 15)

mp: (amorphous); $^1$H NMR (270 MHz, DMSO-d$_6$) δ ppm: 3.72 (2H, s), 7.29–7.43 (8H, m), 7.77 (2H, d, J=8.8 Hz), 8.00 (2H, d, J=8.8 Hz), 10.29 (1H, s), 10.52 (1H, s); IR (KBr)cm$^{-1}$: 3300, 2868, 1664, 1638, 1520.

Example 103

N-(2-Aminophenyl)-4-[(2-nitrophenylacetyl)amino]benzamide Hydrochloride (Table 1: Hydrochloride of Compound 19)

mp: (amorphous); $^1$H NMR (270 MHz, DMSO-d$_6$) δ ppm: 4.20 (2H, s), 7.20–7.30 (3H, m), 7.40–7.45 (1H, m), 7.60 (2H, d), 7.71–7.77 (3H, m), 8.02–8.10 (4H, m), 10.27 (1H, br.s), 10.64 (1H, br.s); IR (KBr)cm$^{-1}$: 3263; 1676, 1647, 1518, 1184, 759.

Example 104

N-(2-Aminophenyl)-4-[(4-nitrophenylacetyl)amino]benzamide (Table 1: Compound 21)

mp: 222–226° C.; $^1$H NMR (270 MHz, DMSO-d$_6$) δ ppm: 3.90 (2H, s), 4.96 (2H, br.s), 6.60 (1H, dt, J=1.5, 6.6 Hz), 6.78 (1H, dd, J=1.5, 6.6 Hz), 6.97 (1H, dt, J=1.5, 6.6 Hz), 7.15 (1H, dd, J=1.5, 6.6 Hz), 7.63 (2H, d, J=8.8 Hz), 7.71 (2H, d, J=8.8 Hz), 7.95 (2H, d, J=8.8 Hz), 8.22 (2H, d, J=8.8 Hz), 9.59 (1H, s), 10.54 (1H, s); IR (KBr)cm$^{-1}$: 3395, 3334, 1671, 1630, 1519, 1346.

Example 105

N-(2-Aminophenyl)-4-[(2-aminophenylacetyl)amino]benzamide (Table 1: Compound 22)

mp: 177–182° C.(dec.); $^1$H NMR (270 MHz, DMSO-d$_6$) δ ppm: 3.54 (2H, s), 4.88 (2H, br.s), 5.09 (2H, br.s), 6.55 (1H, dd, J=6.6, 7.3 Hz), 6.59 (1H, dd, J=7.3, 7.3 Hz), 6.68 (1H, d, J=7.3 Hz), 6.78 (1H, d, J=7.3 Hz), 6.96 (2H, dd, J=7.3, 7.3 Hz), 7.06 (1H, d, J=6.6 Hz), 7.15 (1H, d, J=7.3 Hz), 7.71 (2H, d, J=8.8 Hz), 7.95 (2H, d, J=8.8 Hz), 9.57 (1H, br.s), 10.39 (1H, br.s); IR (KBr)cm$^{-1}$: 3374, 3256 (br.), 1683, 1597, 1503, 1317, 1262, 1180, 1153, 747.

Example 106

N-(2-Aminophenyl)-4-[(4-aminophenylacetyl)amino]benzamide (Table 1: Compound 26)

mp: 219–226° C.(dec.); $^1$H NMR (270 MHz, DMSO-d$_6$) δ ppm: 3.46 (2H, s), 4.93 (4H, br.s), 6.52 (2H, d, J=8.1 Hz), 6.59 (1H, dt, J=1.5, 7.3 Hz), 6.77 (1H, dd, J=1.4, 7.3 Hz), 6.97 (1H, dt, J=1.4, 7.3 Hz), 6.99 (2H, d, J=8.1 Hz), 7.15 (1H, dd, J=1.5, 7.3 Hz), 7.70 (2H, d, J=8.8 Hz), 7.93 (2H, d, J=8.8 Hz); IR (KBr)cm$^{-1}$: 3278, 3032, 1675, 1628, 1516.

Example 107

N-(2-Aminophenyl)-4-[(4-methoxyphenylacetyl)amino]benzamide (Table 1: Compound 32)

mp: (amouphous); $^1$H NMR (270 MHz, DMSO-d$_6$) δ ppm: 3.62 (2H, s), 3.74 (3H, s), 6.90 (2H, d, J=8.8 Hz), 7.26 (2H, d, J=8.8 Hz), 7.30 (3H, m), 7.39 (1H, m), 7.77 (2H, d, J=8.8 Hz), 7.99 (2H, d, J=8.8 Hz), 10.26 (1H, s), 10.44 (1H, s); IR (KBr)cm$^{-1}$: 3300, 2759, 1670, 1638, 1514, 1250.

Example 108

N-(2-Aminophenyl)-4-[[4-(N,N-dimethylamino)phenylacetyl]amino]benzamide (Table 1: Compound 53)

mp: 140° C.; $^1$H NMR (270 MHz, DMSO-d$_6$) δ ppm: 3.04 (6H, s), 3.67 (2H, s), 7.16 (2H, d, J=8.0 Hz), 7.29–7.40 (6H, m), 7.76 (2H, d, J=8.8 Hz), 7.99 (2H, d, J=8.8 Hz), 10.29 (1H, s), 10.47 (1H, s); IR (KBr)cm$^{-1}$: 3244, 2951, 2639, 1647, 1599, 1507.

Example 109

N-(2-Aminophenyl)-4-[(4-trifluoromethylphenylacetyl)amino]benzamide (Table 1: Compound 43)

mp: (amorphous); $^1$H NMR (270 MHz, DMSO-d$_6$) δ ppm: 3.84 (2H, s), 6.89 (1H, t, J=7.4 Hz), 7.00 (1H, d, J=7.4

Hz), 7.11 (1H, t, J=7.4 Hz), 7.25 (1H, d, J=7.4 Hz), 7.57 (2H, d, J=8.8 Hz), 7.71 (2H, d, J=8.8 Hz), 7.73 (2H, d, J=8.8 Hz), 7.97 (2H, d, J=8.8 Hz), 9.87 (1H, s), 10.54 (1H, s); IR (KBr)cm$^{-1}$: 3260, 1664, 1605, 1521, 1327, 1119.

Example 110

N-(2-Aminophenyl)-4-[(pyridin-2-yl)acetylamino] benzamide Dihydrochloride (Table 1: Hydrochloride of Compound 174)

mp: (amorphous); $^1$H NMR (270 MHz, DMSO-d$_6$) δ ppm: 4.60 (2H, s), 7.30–7.46 (3H, m), 7.56 (1H, d, J=7.4 Hz), 7.79 (2H, d, J=8.8 Hz), 7.95 (1H, t, J=6.6 Hz), 8.01 (1H, d, J=7.4 Hz), 8.11 (2H, d, J=8.8 Hz), 8.49 (1H, t, J=7.4 Hz), 8.87 (1H, d, J=5.1 Hz), 10.46 (1H, s).

Example 111

N-(2-Aminophenyl)-4-[(pyridin-3-yl)acetylamino] benzamide Dihydrochloride (Table 1: Hydrochloride of Compound 68)

mp: 182–189° C. (dec.); $^1$H NMR (270 MHz, DMSO-d$_6$) δ ppm: 4.12 (2H, s), 7.29–7.59 (4H, m), 7.80 (2H, d, J=8.8 Hz), 8.05 (1H, m), 8.11 (2H, d, J=8.8 Hz), 8.57 (1H, d, J=8.1 Hz), 8.85 (1H, d, J=5.2 Hz), 8.95 (1H, s), 10.25 (1H, s), 10.48 (1H, s).

Example 112

N-(2-Aminophenyl)-4-[[3-(pyridin-3-yl)propanoyl] amino]benzamide (Table 1: Compound 69)

mp: 184–186° C.; $^1$H NMR (270 MHz, DMSO-d$_6$) δ ppm: 2.80 (2H, t, J=7.3 Hz), 3.08 (2H, t, J=7.3 Hz), 6.87 (1H, t, J=8.0 Hz), 6.99 (1H, dd, J=1.4, 8.0 Hz), 7.11 (1H, dt, J=1.4, 8.0 Hz), 7.25 (1H, d, J=8.0 Hz), 7.70 (2H, d, J=8.8 Hz), 7.77 (1H, dd, J=5.8, 8.0 Hz), 7.96 (2H, d, J=8.8 Hz), 8.22 (1H, d, J=8.0 Hz), 8.75 (1H, d, J=1.4 Hz), 9.83 (1H, s), 10.25 (1H, s).

Example 113

N-(2-Aminophenyl)-2-chloro-4-[3-(pyridin-3-yl) propanoylamino]benzamide (Table 1: Compound 123)

mp: (amorphous); $^1$H NMR (270 MHz, DMSO-d$_6$) δ ppm: 2.70 (2H, t, J=8.1 Hz), 2.96 (2H, t, J=7.3 Hz), 4.74 (2H, br.s), 6.60 (1H, t, J=6.6 Hz), 6.78 (1H, d, J=6.6 Hz), 6.95 (1H, t, J=6.6 Hz), 7.19 (1H, dd, J=1.5, 7.3 Hz), 7.29 (1H, dd, J=5.1, 7.3 Hz), 7.66 (1H, d, J=8.8 Hz), 7.92 (2H, d, J=8.8 Hz), 8.48 (1H, d, J=2.2 Hz), 9.37 (1H, s), 10.00 (1H, s); IR (KBr)cm$^{-1}$: 3273, 1675, 1519, 1315, 1181, 852, 747.

Example 114

N-(2-Aminophenyl)-4-[[N-(pyridin-3-yl)methyl-N-trifluoroacetylamino]acetylamino]benzamide (Table 1: Compound 107)

mp: 145° C. (dec.); $^1$H NMR (270 MHz, DMSO-d$_6$) δ ppm: 4.18 and 4.42 (total 2H, s), 4.73 and 4.83 (total 2H, s), 4.87 (2H, br.s), 6.60 (1H, dd, J=7.3, 8.1 Hz), 6.78 (1H, d, J=8.1 Hz), 6.96 (H, dd, J=7.3, 7.3 Hz), 7.16 (1H, d, J=8.1 Hz), 7.35–7.45 (1H, m), 7.66 (2H, d, J=5.9 Hz), 7.70–7.80 (1H, m), 7.90–8.00 (2H, m), 8.51–8.55 (1H, m), 8.58 (1H, s), 9.60 (1H, br.s), 10.36 and 10.43 (total 1H, br.s).

Example 115

N-2-Aminophenyl)-4-[[N-(pyridin-3-yl) methylamino]acetylamino]benzamide (Table 1: Compound 105)

mp: 160° C. (dec.); $^1$H NMR (270 MHz, DMSO-d$_6$) δ ppm: 3.30 (2H, s), 3.79 (2H, s), 4.88 (2H, s), 6.60 (1H, dd, J=7.3, 7.3 Hz), 6.78 (1H, d, J=8.1 Hz), 6.97 (1H, dd, J=7.3, 8.1 Hz), 7.16 (1H, d, J=8.1 Hz), 7.74 (2H, d, J=8.8 Hz), 7.80 (1H, d, J=7.3 Hz), 7.95 (2H, d, J=8.1 Hz), 8.46 (1H, d, J=3.7 Hz), 8.57 (1H, s), 9.57 (1H, s), 10.08 (1H, br.s); IR (KBr) cm$^{-1}$: 3298, 1693, 1637, 1602, 1544, 1454, 1262, 848, 762.

Example 116

N-(2-Aminophenyl)-4-[N-(pyridin-3-yl)-methyloxamoylamino]benzamide (Table 1: Compound 104)

mp: (amorphous); $^1$H NMR (270 MHz, DMSO-d$_6$) δ ppm: 4.43 (2H, d, J=6.6 Hz), 4.90 (2H, br.s), 6.60 (1H, dd, J=6.6, 7.3 Hz), 6.78 (1H, d, J=7.3 Hz), 6.97 (1H, ddd, J=1.5, 6.6, 7.3 Hz), 7.16 (1H, d, J=7.3 Hz), 7.37 (1H, dd, J=4.4, 8.1 Hz), 7.73 (1H, d, J=8.1 Hz), 7.96 and 7.96 (4H, AA'BB', J=9.4 Hz), 8.47 (1H, dd, J=1.5, 5.1 Hz), 8.56 (1H, d, J=1.5 Hz), 9.59 (1H, s), 9.67 (1H, t, J=6.6 Hz), 10.92 (1H, br.s); IR (KBr)cm$^{-1}$: 3299, 1644, 1518, 1320, 1119, 748.

Example 117

N-(2-Aminophenyl)-4-[[N-(pyridin-3-yl)methyl-N-nicotinoylamino]acetylamino]benzamide (Table 1: Compound 106)

mp: (amorphous); $^1$H NMR (270 MHz, DMSO-d$_6$) δ ppm: 4.11 (major 2H, s), 4.26 (minor 2H, s), 4.75 (major 2H, s), 4.65 (minor 2H, s), 4.88 (total 2H, br.s), 6.60 (total 1H, dd, J=7.3, 8.1 Hz), 6.78 (total 1H, d, J=7.3 Hz), 6.97 (total 1H, dd, J=7.3, 8.1 Hz), 7.15 (total 1H, d, J=8.1 Hz), 7.41–7.95 (total 8H, m), 8.46–8.52 (total 1H, m), 8.63–8.70 (total 2H, m), 9.59 (total 1H, s), 10.22 (major 1H, br.s), 10.37 (minor 1H, br.s); IR (KBr)cm$^{-1}$: 3269, 1701, 1637, 1603, 1534, 1506, 1312, 1254, 752.

Example 118

N-(2-Aminophenyl)-4-[[4-(pyridin-3-yl)butanoyl] amino]benzamide (Table 1: Compound 70)

mp: 165–167° C. (dec.); $^1$H NMR (270 MHz, DMSO-d$_6$) δ ppm: 1.88–1.99 (2H, m), 2.68 (2H, t, J=7.3 Hz), 2.39 (2H, t, J=7.3 Hz), 6.78–6.81 (1H, m), 6.94–6.99 (1H, m), 7.15–7.18 (1H, m), 7.34–7.39 (1H, m), 7.69–7.72 (1H, m), 7.94 (2H, d, J=8.8 Hz), 8.43–8.48 (2H, m); IR (KBr)cm$^{-1}$: 3291, 1660, 1626, 1308, 1261, 1182, 1027, 825, 747.

Example 119

N-(2-Aminophenyl)-4-[[N-(pyridin-3-yl)methyl-N-methylamino]acetylamino]benzamide (Table 1: Compound 108)

mp: 154–155° C.; $^1$H NMR (270 MHz, DMSO-d$_6$) δ ppm: 2.28 (3H, s), 3.27 (2H, s), 3.71 (2H, s) 4.88 (2H, br.s), 6.60 (1H, dd, J=6.6, 7.3 Hz), 6.78 (1H, d, J=8.1 Hz), 6.97 (1H, dd, J=7.3, 8.1 Hz), 7.16 (1H, d, J=8.1 Hz), 7.38 (1H, dd, J=2.9, 8.1 Hz), 7.77 (2H, d, J=8.8 Hz), 7.75–7.85 (1H, m), 7.95 (2H, d, J=8.8 Hz), 8.47 (1H, d, J=1.5 Hz), 8.49 (1H, s), 9.56 (1H, s), 10.62 (1H, br.s).

Example 120

N-(2-Aminophenyl)-4-[N-(pyridin-3-yl) oxyacetylamino]benzamide (Table 1: Compound 65)

mp: 175–179° C.; $^1$H NMR (270 MHz, DMSO-d$_6$) δ ppm: 4.86 (2H, s), 4.90 (2H, br.s), 6.60 (1H, d, J=7.3, 7.3. Hz), 6.78 (1H, d, J=7.3 Hz), 6.97 (1H, dd, J=6.6, 7.3 Hz), 7.16 (1H, d, J=8.1 Hz), 7.34–7.47 (2H, m), 7.76 (2H, d, J=8.8 Hz), 7.98 (2H, d, J=8.8 Hz), 8.22 (1H, d, J=3.6 Hz), 8.39 (1H, d, J=2.9 Hz), 9.60 (1H, br.s), 10.40 (1H, br.s); IR (KBr)cm$^{-1}$: 3321, 1655, 1530, 1276, 1231, 1068, 757.

Example 121

N-(2-Aminophenyl)-4-[4-(pyridin-3-yl)-1,4-dioxobutylamino]benzamide (Table 1: Compound 99)

mp: 190–194° C.; $^1$H NMR (270 MHz, DMSO-d$_6$) δ ppm: 2.08 (2H, t, J=6.4 Hz), 3.41 (2H, t, J=6.4 Hz), 4.86 (2H, s), 6.59 (1H, t, J=5.6 Hz), 6.78 (1H, d, J=7.9 Hz), 6.96 (1H, t, J=7.4 Hz), 7.15 (1H, d, J=7 Hz), 7.58 (1H, dd, J=4.9, 7.9 Hz), 7.70 (2H, d, J=8.9 Hz), 7.94 (2H, d, J=8.9 Hz), 8.35 (1H, d, J=7.9 Hz), 8.81 (1H, d, J=4 Hz), 9.18 (1H, s), 9.56 (1H, s), 10.32 (1H, s); IR (KBr)cm$^{-1}$: 3317, 1691, 1652, 1601, 1522, 1312, 982, 847, 764, 701.

Example 122

N-(2-Aminophenyl)-4-[3-[N-(pyridin-3-yl)amino]-1,3-dioxopropylamino]benzamide (Table 1: Compound 94)

mp: 196° C. (dec.); $^1$H NMR (270 MHz, DMSO-d$_6$) δ ppm: 3.57 (2H, s), 4.87 (2H, s), 6.57–6.62 (1H, m), 6.76–6.79 (1H, m), 6.94–6.99 (1H, m), 7.14–7.17 (1H, m), 7.33–7.38 (11H, m), 7.73 (2H, d, J=8.8 Hz), 7.97 (2H, d, J=8.8 Hz), 8.05–8.08 (1H, m), 8.27–8.30 (1H, m), 8.75–8.76 (1H, m), 9.59 (1H, s), 10.44 (1H, s), 10.47 (1H, s); IR (KBr)cm$^{-1}$: 3410, 3315, 1685, 1655, 1625, 1536, 1428, 1362, 1263, 1201, 744.

Example 123

N-(2-Aminophenyl)-4-[N-(pyridin-3-yl)methoxyacetylamino]-3-methylbenzamide (Table 1: Compound 102)

mp: 178–181° C. (dec.); $^1$H NMR (270 MHz, DMSO-d$_6$) δ ppm: 2.28 (3H, s), 4.22 (2H, s), 4.71 (2H, s), 4.89 (2H, br.s), 6.60 (1H, dd, J=7.3, 7.3 Hz), 6.78 (1H, d, J=8.1 Hz), 6.97 (1H, dd, J=7.3, 8.1 Hz), 7.16 (1H, d, J=7.3 Hz), 7.43 (1H, dd, J=4.4, 8.1 Hz), 7.71 (1H, d, J=8.1 Hz), 7.79–7.89 (3H, m), 8.54 (1H, dd, J=1.5, 4.4 Hz), 8.66 (1H, d, J=1.5 Hz), 9.36 (1H, br.s), 9.60 (1H, br.s); IR (KBr)cm$^{-1}$: 3394, 3269, 1683, 1630, 1593, 1521, 1460, 1131, 750, 716.

Example 124

N-(2-Aminophenyl)-4-[N-(thiophen-3-yl)methoxyacetylamino]benzamide (Table 1: Compound 204)

mp: 186–189° C.; $^1$H NMR (270 MHz, DMSO-d$_6$) δ ppm: 4.11 (2H, s), 4.63 (2H, s), 4.89 (2H, br.s), 6.60 (1H, dd, J=7.3, 7.3 Hz), 6.78 (1H, d, J=8.1 Hz), 6.97 (1H, dd, J=7.3, 7.3 Hz), 7.12–7.19 (2H, m), 7.53–7.57 (2H, m), 7.78 (2H, d, J=8.8 Hz), 7.95 (2H, d, J=8.8 Hz), 9.58 (1H, br.s), 10.04 (1H, br.s); IR (KBr)cm$^{-1}$: 3341, 3248, 1694, 1631, 1611, 1506, 1314, 1126.

Example 125

N-(2-Aminophenyl)-4-[N-methyl-N-(pyridin-3-yl)methoxyacetylamino]benzamide (Table 1: Compound 103)

mp: 180–183° C. (dec.); $^1$H NMR (270 MHz, DMSO-d$_6$) δ ppm: 3.24 (3H, s), 4.08 (2H, br.s), 4.50 (2H, s), 4.94 (2H, br.s), 6.60 (1H, dd, J=7.3, 7.3 Hz), 6.79 (1H, d, J=8.1 Hz), 6.98 (1H, dd, J=1.3, 8.1 Hz), 8.03 (1H, d, J=8.1 Hz), 8.48–8.50 (2H, m), 9.72 (1H, br.s); IR (KBr)cm$^{-1}$: 3395, 3283, 1683, 1639, 1604, 1506, 1459, 1307, 1124.

Example 126

N-(2-Aminophenyl)-4-[N-(pyridin-2-yl)methoxyacetylamino]benzamide (Table 1: Compound 176)

mp: 171–173° C.; $^1$H NMR (270 MHz, DMSO-d$_6$) δ ppm: 4.26 (2H, s), 4.74 (2H, s), 4.89 (2H, br.s), 6.60 (1H, dd, J=6.6, 8.1 Hz), 6.78 (1H, d, J=7.3 Hz), 6.97 (1H, ddd, J=1.5, 7.3, 8.1 Hz), 7.16 (1H, d, J=7.3 Hz), 7.35 (1H, dd, J=5.1, 6.6 Hz), 7.80 (2H, d, J=8.1 Hz), 7.80–7.89 (1H, m), 7.97 (2H, d, J=8.1 Hz), 8.59 (1H, d, J=4.4 Hz), 9.59 (1H, br.s), 10.30 (1H, br.s); IR (KBr)cm$^{-1}$: 3391, 3258, 1678, 1629, 1593, 1517, 1128, 767, 742.

Example 127

N-(2-Aminophenyl)-4-[N-(N-nicotinoylamino)acetylamino]benzamide (Table 1: Compound 97)

mp: 218–220° C. (dec.); $^1$H NMR (270 MHz, DMSO-d$_6$) δ ppm: 4.13 (2H, d, J=5.9 Hz), 4.89 (2H, s), 6.59 (1H, dd, J=7.3, 7.3 Hz), 6.77 (1H, d, J=8.1 Hz), 6.96 (1H, dd, J=7.3, 8.1 Hz), 7.15 (1H, d, J=7.3 Hz), 7.55 (1H, dd, J=5.1, 8.1 Hz), 7.73 (2H, d, J=8.8 Hz), 7.96 (2H, d, J=8.8 Hz), 8.25 (1H, d, J=8.1 Hz), 8.74 (1H, d, J=5.1 Hz), 9.07 (1H, d, J=1.5 Hz), 9.13 (1H, t-like, J=5.9 Hz), 9.58 (1H, s), 10.36 (1H, s).

Example 128

N-(2-Aminophenyl)-5-[3-(pyridin-3-yl)propionamide]benzofuran-2-carboxyamide (Table 3: Compound 1)

mp: 267–272° C.; $^1$H NMR (270 MHz, DMSO-d$_6$) δ ppm: 2.51 (2H, t, J=7.3 Hz), 2.97 (2H, t, J=7.3 Hz), 6.61 (1H, dd, J=8.1, 8.8 Hz), 6.80 (1H, dd, J=1.5, 8.1 Hz), 6.99 (1H, dd, J=8.1, 8.8 Hz), 7.20 (1H, dd, J=1.5, 8.1 Hz), 7.32 (1H, dd, J=5.2, 8.1 Hz), 7.49 (1H, dd, J=1.5, 8.8 Hz), 7.61 (1H, d, J=8.8 Hz), 7.67 (1H, s), 7.70 (1H, m), 8.15 (1H, d, J=1.5 Hz), 8.40 (1H, dd, J=1.5, 5.2 Hz), 8.51 (1H, d, J=1.5 Hz), 9.84 (1H, s), 10.1 (1H, s); IR (KBr)cm$^{-1}$: 3333, 3272, 1666, 1583, 1561, 1458, 1314, 1247, 1143, 807, 746, 713.

Example 129

Preparation of N-(2-Aminophenyl)-4-[N-[2-(pyridin-3-yl)oxypropionyl]amino]benzamide (Table 4: Compound 2)

(29-1) In 10 mL of dichloromethane were dissolved 0.34 g of the compound from Example 47, the process (47-2) (1.2 mmol) and 0.34 g of the compound from Example 100, the process (100-2) (1.0 mmol), and then 0.5 mL of triethylamine (3.6 mmol). Under ice-cooling, to the solution was added 0.21 g of 2-chloro-1,3-dimethylimidazolidinium chloride (1.24 mmol) in 5 mL of dichloromethane, and the solution was stirred under ice-cooling for 2 hours. After neutralizing with saturated sodium bicarbonate aq., the mixture was diluted with water and extracted with chloroform. The organic layer was washed with saturated brine, dried and evaporated. The residue was purified by column chromatography on silica gel (eluent: ethyl acetate:methanol=10:1) to give 0.68 g of N-[2-(N-tert-butoxycarbonylamino)phenyl]-4-[N-[2-(pyridin-3-yl)

oxypropionyl]amino]benzamide as a mixture with 1,3-dimethyl-2-imidazolinone.

$^1$H NMR (270 MHz, CDCl$_3$) δ ppm: 1.52 (9H, s), 1.70 (3H, d, J=6.6 Hz), 4.84 (1H, q, J=6.6 Hz), 6.89 (1H, br.s), 7.12–7.31 (6H, m), 7.68 (2H, d, J=8.8 Hz), 7.79 (1H, d, J=8.1 Hz), 7.96 (2H, d, J=8.8 Hz), 8.34 (1H, d, J=2.9, 2.9 Hz), 8.43 (1H, d, J=1.5 Hz), 9.25 (1H, br.s).

(129-2) To a solution of 0.68 g of the compound from the process (129-1) in 5 mL of dichloromethane was added 10 mL of 15% (vol/vol) trifluoroacetic. acid/dichloromethane, and the solution was stirred at room temperature for 4.5 hours. After neutralizing the solution with saturated sodium bicarbonate aq., dichloromethane was removed by evaporation. The solution was extracted with ethyl acetate. The organic layer was washed with saturated brine, dried and evaporated. To the residue were added methanol and diisopropyl ether, and the precipitated solid was collected by filtration and dried to give 0.22 g of N-(2-aminophenyl)-4-[N-[2-(pyridin-3-yl)oxypropionyl]amino]benzamide (Yield: 5.8% for the 2 steps) as an opalescent solid.

mp: 193–196° C.; $^1$H NMR (270 MHz, DMSO-d$_6$) δ ppm: 1.60 (3H, d, J=6.6 Hz), 4.88 (2H, br.s), 5.04 (1H, q, J=6.6 Hz), 6.60 (1H, dd, J=6.6, 7.3 Hz), 6.78 (1H, d, J=8.1 Hz), 6.97 (1H, dd, J=7.3, 8.1 Hz), 7.15 (1H, d, J=7.3 Hz), 7.32–7.39 (2H, m), 7.75 (2H, d, J=8.8 Hz), 7.96 (2H, d, J=8.1 Hz), 8.20 (1H, dd, J=1.5, 3.7 Hz), 8.35 (1H, d, J=2.1 Hz), 9.59 (1H, br.s), 10.44 (1H, br.s).

Example 130

Preparation of N-(2-Aminophenyl)-4-[(pyridin-3-yl)methoxyacetylamino]benzamide (Table 1: Compound 101)

(130-1) To a suspension of 4.4 g of sodium hydride (60% oil dispersion; 110 mmol) in 300 mL of THF were added dropwise 10.91 g of 3-pyridinemethanol (100 mmol) in 20 mL of THF at room temperature, and the mixture was stirred at room temperature for 2 hours. The resulting white suspension was ice-cooled, and 19.51 g of tert-butyl bromoacetate (100 mmol) in 20 mL of THF was added dropwise, maintaining the inner temperature within 10 to 12° C. The suspension was warmed to room temperature with stirring for 3 hours, and then left overnight. After adding water and saturated sodium bicarbonate aq., the mixture was extracted with ethyl acetate. The organic layer was washed with saturated brine, dried and evaporated. The residue was purified by column chromatography on silica gel (gradient elution with n-hexane:ethyl acetate=1:1 to ethyl acetate) to give 7.56 g of tert-butyl (pyridin-3-yl)methoxyacetate (33.8%) as a light brown oil.

$^1$H NMR (270 MHz, CDCl$_3$) δ ppm: 1.49 (9H, s), 4.03 (2H, s), 4.64 (2H, s), 7.30 (1H, dd, J=4.9, 7.3 Hz), 7.76 (1H, d, J=7.3 Hz), 8.56 (1H, d, J=4.9 Hz), 8.60 (1H, s).

(130-2) Under ice-cooling, 12 mL of trifluoroacetic acid was added to 3.5 g of the compound from the process (130-1) (15.7 mmol), and the solution was stirred at room temperature for 6 hours. Part of trifluoroacetic acid was removed by evaporation to give a mixture of (pyridin-3-yl)methoxyacetic acid and trifluoroacetic acid (6.5 g). The mixture was dissolved in 70 mL of dichloromethane. To the solution was added 25 mL of pyridine and then, was slowly added dropwise under ice-cooling, 2.37 g of 2-chloro-1,3-dimethylimidazolinium chloride (14.0 mmol) in 20 mL of dichloromethane over 30 min, and the solution was stirred under ice-cooling for additional 5 hours. To the solution was added saturated sodium bicarbonate aq., and stirring was continued until foaming ceased. The mixture was extracted with chloroform. The organic layer was washed with saturated brine, dried and evaporated. The residue was purified by column chromatography on silica gel (gradient elution with ethyl acetate to ethyl acetate:methanol=10:1) to give 4.78 g of N-[2-(N-tert-butoxycarbonyl)aminophenyl]-4-[N-(pyridin-3-yl)methoxyacetylamino]benzamide (Yield: 62%) as a 1:1 (molar ratio) mixture with DMI (1,3-dimethyl-2-imidazolinone).

$^1$H NMR (270 MHz, CDCl$_3$) δ ppm: 1.51 (9H, s), 4.15 (2H, s), 4.70 (2H, s), 6.92 (1H, br.s), 7.15–7.29 (3H, m), 7.37 (1H, dd, J=7.3, 5.1 Hz), 7.67 (2H, d, J=8.8 Hz), 7.71–7.79 (2H, m), 7.96 (2H, d, J=8.8 Hz), 8.41 (1H, s), 8.62–8.66 (2H, m), 9.23 (1H, br.s).

(130-3) To a solution of 2.39 g of the compound from the process (130-2) (4.0 mmol) in 28 mL of dichloromethane was added 55 mL of 15% (vol/vol) trifluoroacetic acid/dichloromethane, and the solution was stirred at room temperature for 7 hours. The solution was neutralized with saturated sodium bicarbonate, and then water was added. The reaction mixture was stirred at room temperature and extracted with a 2:1 mixture of ethyl acetate-methyl ethyl ketone, a 2:1 mixture of ethyl acetate-THF, and ethyl acetate, in sequence. The combined organic layer was washed with saturated brine and dried over anhydrous sodium sulfate. After removing the dehydrating reagent by filtering, the filtrate was concentrated. To the residue thus obtained were added methanol and diisopropyl ether, and the precipitated solid was collected by filtration and dried to give 1.29 g of N-(2-aminophenyl)-4-[N-(pyridin-3-yl)methoxyacetylamino]benzamide (Yield: 85.6%) as a dark brown solid.

$^1$H NMR (270 MHz, DMSO-d$_6$) δ ppm: 4.19 (2H, s), 4.68 (2H, s), 4.90 (2H, br.s), 6.60 (1H, ddd, J=1.5, 7.3, 8.1 Hz), 6.78 (1H, dd, J=1.5, 8.1 Hz), 6.97 (1H, dd, J=7.3, 7.3 Hz), 7.15 (1H, d, J=7.3 Hz), 7.42 (1H, dd, J=4.4, 8.1 Hz), 7.77 (2H, d, J=8.8 Hz), 7.85 (1H, d, J=7.3 Hz), 7.96 (2H, d, J=8.8 Hz), 8.54 (1H, dd, J=1.5, 5.1 Hz), 8.63 (1H, s), 9.58 (1H, s), 10.09 (1H, s); IR (KBr)cm$^{-1}$: 3403, 3341, 3250, 1694, 1630, 1610, 1506, 1314, 1259, 1118, 764.

Example 131

Preparation of N-(2-Aminophenyl)-4-[N-[2-(pyridin-3-yl)methoxypropionyl]amino]benzamide (Table 4: Compound 1)

(131-1) To a suspension of 1.24 g of sodium hydride (60% oil dispersion; 31 mmol) in 90 mL of THF were added dropwise 3.27 g of 3-pyridinemethanol (30 mmol) in 10 mL of dry THF at room temperature over 5 min. The resulting white suspension was stirred at room temperature for an hour, to which was then added dropwise 6.27 g of tert-butyl 2-bromopropionate (30 mmol) in 10 mL of dry THF at room temperature over 5 min. The mixture was stirred at room temperature for 11.5 hours. After adding water, the mixture was extracted with ethyl acetate. The organic layer was washed with saturated brine, dried and evaporated. The residue was purified by column chromatography on silica gel (eluent: n-hexane:ethyl acetate=1:1) to give 4.01 g of tert-butyl (pyridin-3-yl)methoxyacetate (Yield: 56.3%) as a dark brown oil.

$^1$H NMR (270 MHz, CDCl$_3$) δ ppm: 1.42 (3H, d, J=7.3 Hz), 1.50 (9H, s), 3.96 (1H, q, J=6.6 Hz), 4.47, 4.69 (2H, ABq, J=11.0 Hz), 7.29 (1H, dd, J=5.1, 8.1 Hz), 7.75 (1H, d, J=8.1 Hz), 8.5 (1H, d, J=4.4 Hz), 8.60 (1H, s).

(131-2) To a solution of 1.09 g of the compound from the process (131-1) (4.59 mmol) in 5 mL of dichloromethane was added 8 mL of trifluoroacetic acid, and the solution was stirred at room temperature for 9.5 hours. After evaporation, to the residue was added 25 mL of dichloromethane and 3 mL of pyridine. Under ice-cooling, to the solution was added dropwise 0.70 g of 2-chloro-1,3-dimethylimidaolidinium chloride (4.1 mmol) in 8.mL of dichloromethane, and then the mixture was stirred for 30 min. To the solution was slowly added dropwise 0.98 g of the compound from Example 100, the process (100-2) (3.0 mmol) in 20 mL of dichloromethane and 10 mL of pyridine under ice-cooling over 15 min, and the solution was warmed to room temperature with stirring for 8 hours. After adding saturated sodium bicarbonate aq., the mixture was diluted with water and extracted with chloroform. The organic layer was washed with saturated brine, dried and evaporated. The residue was purified by column chromatography on silica gel (eluent: ethyl acetate:methanol=8:1) to give 1.19 g of N-[2-(N-tert-butoxycabonylamino)phenyl]-4-[N-[2-(pyridin-3-yl)methoxypropionyl]amino]benzamide as a 2:3 (molar ratio) mixture with 1,3-dimethyl-2-imidazolinone.

$^1$H NMR (270 MHz, CDCl$_3$) δ ppm: 1.51 (9H, s), 1.54 (3H, d, J=6.6 Hz), 4.13 (1H, q, J=6.6 Hz), 4.65, 4.71 (2H, ABq, J=11.7 Hz), 7.12–7.18 (2H, m), 7.28–7.37 (3H, m), 7.65 (2H, d, J=8.1 Hz), 7.73 (2H, br.d, J=5.9 Hz), 7.96 (2H, d, J=8.8 Hz), 8.59–8.64 (3H, m), 9.39 (1H, br.s).

(131-3) To a solution of 1.19 g of the compound from the process (131-2) (1.8 mmol) in 10 mL of, dichloromethane was added 20 mL of 15% (vol/vol) trifluoroacetic acid in dichloromethane, and the solution was stirred at room temperature for 4.5 hours. The solution was poured into saturated sodium bicarbonate, and dichloromethane was removed by evaporation. The resulting aqueous layer was extracted with ethyl acetate. The organic layer was washed with saturated brine, dried and evaporated. To the residue were added methanol and diisopropyl ether, and the precipitated solid was collected by filtration and dried to give 585 mg of N-(2-aminophenyl)-4-[N-[2-(pyridin-3-yl)methoxypropionyl]amino]benzamide as a light brown solid.

mp: 144–148° C.; $^1$H NMR (270 MHz, DMSO-d$_6$) δ ppm: 1.40 (3H, d, J=6.6 Hz), 4.14 (1H, q, J=6.6 Hz), 4.56 and 4.65 (2H, ABq, J=11.8 Hz), 4.89 (2H, br.s), 6.60 (1H, dd, J=7.3, 7.3 Hz), 6.78 (1H, d, J=8.1 Hz), 6.97 (1H, dd, J=6.6, 7.3 Hz), 7.16 (1H, d, J=7.3 Hz), 7.40 (1H, dd, J=4.4 Hz, 7.3 Hz), 7.78–7.85 (3H, m), 7.97 (2H, d, J=8.8 Hz), 8.52 (1H, dd, J=1.5, 5.1 Hz), 8.61 (1H, d, J=2.1 Hz), 9.60 (1H, s), 10.15 (1H, s).

Example 132

Preparation of N-(2-Aminophenyl)-4-(N-benzylamino)carbonylbenzamide (Table 1: Compound 8)

(132-1) To a suspension of 13.0 g of monomethyl terephthalate (72.2 mmol) in 100 mL of toluene was added dropwise 10 mL of thionyl chloride at room temperature. After stirring at 80° C. for 3 hours, the solvent and an excess amount of thionyl chloride were removed by evaporation. The residue was suspended in 100 mL of dioxane, and 9.98 g of 2-nitroaniline (72.2 mmol) were added to the suspension, followed by refluxing with heating for 4 hours.

After cooling and evaporation, the residue was washed with methanol to give 20.3 g of N-(2-nitrophenyl)-4-methoxycarbonylbenzamide (Yield: 93.7%) as a yellow solid.

$^1$H NMR (270 MHz, DMSO-d$_6$) δ ppm: 3.91 (3H, s), 7.43–7.49 (1H, m), 7.76–7.78 (2H, m), 8.03 (1H, d, J=8.1 Hz), 8.08 (2H, d, J=8.8 Hz), 8.14 (2H, d, J=8.8 Hz), 10.94 (1H, s).

(132-2) To a solution of 4.24 g of the compound from the process (132-1) in 50 mL of THF and 50 mL of methanol was added 0.4 g of 10% Pd/C in a stream of nitrogen, and the mixture was stirred in a stream of hydrogen for 1.5 hours. The catalyst was removed by filtration, and the filtrate was evaporated. The residue was washed with methanol to give 3.4 g of N-(2-aminophenyl)-4-methoxycarbonylbenzamide (Yield: 87.5%) as a light yellow solid.

$^1$H NMR (270 MHz, DMSO-d$_6$) δ ppm: 3.90 (3H, s), 4.95 (2H, s), 6.60 (1H, dd, J=7.3, 8.1 Hz), 6.78 (1H, d, J=7.3 Hz), 6.99 (1H, dd, J=7.3, 7.3 Hz), 7.17 (1H, d, J=7.3 Hz), 8.08 (2H, d, J=8.1 Hz), 8.11 (2H, d, J=8.1 Hz), 9.85 (1H, s).

(132-3) To a solution of 2.71 g of the compound from the process (132-2) (10.0 mmol) in 100 mL of dioxane and 50 mL of water was added 5% sodium hydroxide aq. under ice-cooling, and then were added dropwise 2.62 g of di-tert-butyl dicarbonate (12.0 mmol) in 40 mL of dioxane. The mixture was stirred at room temperature for 4 hours and left overnight. To the mixture were added saturated brine and ethyl acetate, and the two layers were separated. The aqueous layer was extracted with ethyl acetate. The organic layer was washed with saturated brine, dried and evaporated. The residue was washed with methanol to give 3.54 g of N-[2-(N-tert-butoxycarbonyl)aminophenyl]-4-methoxycarbonylbenzamide (Yield: 95.7%) as a light brown solid.

$^1$H NMR (270 MHz, DMSO-d$_6$) δ ppm: 1.44 (9H, s), 3.90 (3H, s), 7.12–7.24 (2H, m), 7.55–7.58 (2H, m), 8.09 (2H, d, J=8.8 Hz), 8.10 (2H, d, J=8.8 Hz), 8.72 (1H, s), 10.00 (1H, s).

(132-4) A suspension of 3.00 g of the compound from the process (132-3) (8.10 mmol) in 50 mL of methanol and 25 mL of 0.5N lithium hydroxide aq. was heated with stirring at 40° C. for 5 hours. After removing methanol by evaporation, to the residue was added 1N hydrochloric acid, and the mixture was extracted with ethyl acetate. The organic layer was washed with a small amount of water and saturated brine, dried and evaporated. The residue was washed with methanol to give 2.24 g of terephthalic mono-2-(N-tert-butoxycarbonyl)aminoanilide (Yield: 77.6%) as a light brown solid.

$^1$H NMR (270 MHz, DMSO-d$_6$) δ ppm: 1.45 (9H, s), 7.12–7.21 (2H, m), 7.53–7.58 (2H, m), 8.06 (2H, d, J=8.8 Hz), 8.10 (2H, d, J=8.8 Hz), 8.71 (1H, s), 9.97 (1H, s).

(132-5) To a suspension of 0.20 g of the compound from the process (132-4) (0.56 mmol) in 4 mL of dichloromethane were added 0.14 g of benzylamine (1.3 mmol) and then 0.21 mL of triethylamine (1.5 mmol). To the solution was added 0.25 g of 2-chloro-1,3-dimethylimidazolium chloride (1.48 mmol) under ice-cooling, and then the mixture was stirred under ice-cooling for an hour and at room temperature for an hour. After diluting with chloroform and adding water, the aqueous layer was extracted with chloroform.

The combined organic layer was washed with saturated brine, dried and evaporated. The residue was purified by column chromatography on silica gel (eluent: chloroform:methanol=10:1). The solid obtained was washed with diethyl ether to give 279 mg of N-(2-tert-butoxycarbonylaminophenyl)-4-(N-benzylamino) carbonylbenzamide (Yield: 62.6%) as a white solid.

$^1$H NMR (270 MHz, DMSO-d$_6$) δ ppm: 1.45 (9H, s), 4.52 (2H, d, J=5.8 Hz), 7.13–7.28 (4H, m), 7.34–7.35 (3H, m), 7.56 (2H, d, J=8.1 Hz), 8.05 (4H, s), 8.71 (1H, br.s), 9.23 (1H, t), 9.94 (1H, s).

(132-6) To 151 mg of the compound from the process (132-5) (0.339 mmol) was added 5 mL of 4N hydrochloric acid-dioxane at room temperature, and the mixture was stirred for 4 hours. After evaporation, the mixture was partitioned between ethyl acetate and saturated sodium bicarbonate aq. After removing the precipitate, the aqueous layer was extracted with ethyl acetate. The combined organic layer was washed with saturated brine, dried and evaporated. To the residue was added diethyl ether, and the precipitate was collected by filtration and dried to give 78 mg of N-(2-aminophenyl)-4-(N-benzylamino) carbonylbenzamide (Yield: 67%) as a white solid.

mp: 239–241° C. (dec.); $^1$H NMR (270 MHz, DMSO-d$_6$) δ ppm: 4.51 (2H, s), 4.93 (2H, br.d), 6.60 (1H, dd, J=7.3, 7.3 Hz), 6.78 (1H, d, J=8.1 Hz), 6.95 (1H, dd, J=7.3, 8.3 Hz), 7.18 (1H, d), 7.23–7.35 (5H, m), 8.01 (2H, d, J=8.8 Hz), 8.07 (2H, d, J=8.8 Hz), 9.22 (1H, br.t), 9.81 (1H, br.s).

As described in Example 132, the compound of Example 133 was prepared, whose melting point (mp), $^1$H NMR data and IR data are shown below.

Example 133

N-(2-Aminophenyl)-4-[N-(2-phenylethyl)amino] carbonylbenzamide (Table 1: Compound 9)

mp: 237–240° C. (dec.); $^1$H NMR (270 MHz, DMSO-d$_6$) δ ppm: 2.87 (2H, t, J=7.3 Hz), 3.51 (2H, dt, J=5.9, 7.3 Hz), 4.94 (2H, br.s), 6.60 (1H, dd, J=7.3, 7.3 Hz), 6.78 (1H, d, J=7.3 Hz), 6.98 (1H, dd, J=7.3, 7.3 Hz), 7.15–7.34 (6H, m), 7.93 (2H, d, J=8.1 Hz), 8.04 (2H, d, J=8.1 Hz), 8.73 (1H, t, J=5.1 Hz), 9.76 (1H, br.s); IR (KBr)cm$^{-1}$: 3396, 3320, 1625, 1602, 1539, 1458, 1313, 699.

Example 134

Preparation of N-(2-Aminophenyl)-4-[N-(4-nitrophenoxyacetyl)amino]benzamide (Table 1: Compound 54)

(134-1) To a solution of 3 g of the compound from Example 100, the process (100-2) (9.2 mmol) and 2.16 g of 4-nitrophenoxyacetic acid (11.0 mmol) in 7 mL of DMF were added 2.82 g of dicyclohexylcarbodiimide (13.8 mmol) in 5 mL of DMF and a catalytic amount of N,N-dimethylaminopyridine, and the mixture was stirred for one day. After completion of the reaction, ethyl acetate was added to the mixture, insolubles were filtered off through celite, and the solvent was removed by evaporation.

The residue was recrystallized from chloroform to give 2.34 g of N-[2-(tert-butoxycarbonylamino)phenyl]-4-[(4-nitrophenoxyacetyl)amino]benzamide (Yield: 50%).

$^1$H NMR (270 MHz, DMSO-d$_6$) δ ppm: 1.45 (9H, s), 4.97 (2H, s), 7.12–7.26 (3H, m), 7.23 (2H, d, J=8.8 Hz), 7.53 (1H, dt, J=2.2, 7.3 Hz), 7.79 (2H, d, J=8.8 Hz), 7.95 (2H, d, J=8.8 Hz), 8.25 (2H, d, J=8.8 Hz), 8.71 (1H, s), 9.79 (1H, s), 10.52 (1H, s).

(134-2) To a solution of 0.7 g of the compound from the process (134-1) (1.38 mmol) in 10 mL of acetonitrile was added 1.26 mL of iodotrimethylsilane (8.85 mmol) at room temperature, and the solution was stirred for 2 hours. After completion of the reaction, the solution was concentrated. Ethyl acetate was added to the residue, the solution was stirred for 20 min, and the precipitated crystals were collected by filtration. The crystals were dissolved in methyl ethyl ketone. The solution was washed with saturated sodium thiosulfate aq. and saturated brine in sequence, dried over anhydrous magnesium sulfate, and evaporated. The residue was washed with ethyl acetate to give 0.22 g of N-(2-aminophenyl)-4-[N-(4-nitrophenoxyacetyl)amino] benzamide (Yield: 39%) as white crystals.

mp: 212–215° C. (dec.); $^1$H NMR (270 MHz, DMSO-d$_6$) δ ppm: 4.97 (2H, s), 6.88 (1H, t, J=7.3 Hz), 6.99 (1H, d, J=7.3 Hz), 7.11 (1H, t, J=7.3 Hz), 7.23 (2H, d, J=8.8 Hz), 7.24 (1H, m), 7.77 (2H, d, J=8.8 Hz), 8.00 (2H, d, J=8.8 Hz), 8.25 (2H, d, J=8.8 Hz), 9.89 (1H, s), 10.52 (1H, s); IR (KBr)cm$^{-1}$: 3382, 3109, 1650, 1591, 1508, 1341.

Example 135

Preparation of N-(2-Aminophenyl)-4-[(4-aminophenoxyacetyl)amino]benzamide (Table 1: Compound 55)

To a solution of 1.41 g of the compound from Example 134, the process (134-1) (2.78 mmol) in 15 mL of methanol and 25 mL of THF was added 10% Pd—C, and the mixture was stirred in an atmosphere of hydrogen, at room temperature for an hour. After completion of the reaction, the catalyst was filtered off and the filtrate was concentrated. The residue was triturated with diisopropyl ether to give 1.1 g of N-[2-(tert-butoxycarbonylamino)phenyl]-4-[(4-aminophenoxyacetyl)amino]benzamide.

The product was dissolved in 15 mL of acetonitrile. To the solution was added 0.74 mL of iodotrimethylsilane (5.20 mmol), and the mixture was stirred at room temperature for 3 hours. After completion of the reaction, the mixture was evaporated. The residue was washed with methyl ethyl ketone to give 0.86 g of N-(2-aminophenyl)-4-[(4-aminophenoxyacetyl)amino]benzamide (Yield: 83%)

mp: (amorphous); $^1$H NMR (270 MHz, DMSO-d$_6$) δ ppm: 4.82 (2H, s), 7.13 (2H, d, J=8.8 Hz), 7.30–7.48 (6H, m), 7.82 (2H, d, J=8.8 Hz), 8.03 (2H, d, J=8.8 Hz), 10.34 (1H, s), 10.46 (1H, s); IR (KBr)cm$^{-1}$: 2873, 2590, 1680, 1602, 1505, 1243.

Example 136

Preparation of N-(2-Aminophenyl)-4-(5-phenoxymethyl-1,3-oxazolin-2-on-3-yl)benzamide (Table 2: Compound 1)

(136-1) To 0.7 g of tert-butyl 4-(N-benzyloxycarbonylamino)benzoate (2.14 mmol) in 10 mL of THF at −78° C. was added dropwise 1.33 mL of n-butyl lithium (2.25 mmol) over 5 min. The mixture was stirred at the same temperature for 1.5 hours. To the mixture was then added 0.31 mL of phenylglycidol (2.29 mmol), and the reaction mixture was then stirred at the same temperature for an hour and left overnight at room temperature. After adding saturated ammonium chloride aq., the mixture was extracted twice with ethyl acetate. The organic layer was dried over anhydrous magnesium sulfate and evaporated. The residue was recrystallized from diethyl ether to give 0.31 g of N-[4-(tert-butoxycarbonyl)phenyl]-5-phenoxymethyl-1,3-oxazolin-2-one (Yield: 39%).

$^1$H NMR (270 MHz, DMSO-d$_6$) δ ppm: 1.53 (9H, s), 3.97 (1H, dd, J=6.0, 8.8 Hz), 4.23–4.34 (3H, m), 5.11 (1H, m), 6.94–7.00 (3H, m), 7.31 (2H, m), 7.71 (2H, d, J=8.8 Hz), 7.93 (2H, d, J=8.8 Hz).

(136-2) To a solution of 0.26 g of the compound from the process (136-1) (0.704 mmol) in 4 mL of acetonitrile was added 0.15 mL of trimethylsilyl iodide (1.05 mmol), and the solution was stirred at room temperature for 2 hours. After completion of the reaction, the solution was concentrated. The concentrate was triturated with ethyl acetate-methyl ethyl ketone to give 0.2 g of N-(4-carboxyphenyl)-5-phenoxymethyl-1,3-oxazolin-2-one (Yield: 91%).

$^1$H NMR (270 MHz, DMSO-d$_6$) δ ppm: 3.98 (1H, dd, J=6.6, 9.6 Hz), 4.23–4.34 (3H, m), 5.10 (1H, m), 6.94–6.99

(3H, m), 7.30 (2H, t, J=8.1 Hz), 7.72 (2H, d, J=8.8 Hz), 7.98 (2H, d, J=8.8 Hz), 12.85 (1H, s).

(136-3) To a solution of 0.15 g of the compound from the process (136-2) (0.479 mmol) in 7 mL of dichloromethane were added a catalytic amount of DMF and 0.12 mL of oxalyl chloride (1.40 mmol), and the solution was stirred at room temperature for 2 hours. The solution was concentrated and the residual solvent was azeotropically removed twice with toluene. To a solution of the residue in 4 mL of dichloromethane were added a solution of 0.105 g of the compound from Example 1, the process (1-2) (0.504 mmol) and 0.12 g of pyridine (1.52 mmol) in 1 mL of dichloromethane under ice-cooling, and the solution was warmed to room temperature and stirred for an hour. After completion of the reaction, water was added. The mixture was extracted twice with chloroform. The organic layer was washed with saturated brine, dried over anhydrous magnesium sulfate and evaporated. The residue was triturated with diisopropyl ether to give 0.25 g of N-[2-(N-tert-butoxycarbonylamino)phenyl]-4-(5-phenoxymethyl-1,3-oxazolin-2-on-3-yl)benzamide (Yield: quantitative).

$^1$H NMR (270 MHz, DMSO-d$_6$) δ ppm: 1.52 (9H, s), 4.11 (1H, dd, J=5.9, 6.6 Hz), 4.21–4.27 (3H, m), 5.01 (1H, m), 6.84 (1H, br.s), 6.91 (2H, d, J=8.8 Hz), 7.01 (1H, t, J=7.4 Hz), 7.12–7.34 (5H, m), 7.68 (2H, d, J=8.8 Hz).

(136-4) To a solution of 0.22 g of the compound from the process (136-3) (0.437 mmol) in 4 mL of acetonitrile was added 0.1 mL of trimethylsilyl iodide (0.703 mmol) at room temperature, and the solution was stirred for 2 hours. After adding saturated sodium thiosulfate aq., the mixture was extracted twice with ethyl acetate. The organic layer was dried over anhydrous magnesium sulfate and evaporated. The residue was recrystallized from methanol to give 0.13 g of N-(2-aminophenyl)-4-(5-phenoxymethyl-1,3-oxazolin-2-on-3y)benzamide (Yield: 74%) as white crystals.

mp: 165–170° C. (dec.); $^1$H NMR (270MHz, DMSO-d$_6$) δ ppm: 4.01 (1H, dd, J=6.6, 9.6 Hz), 4.28–4.34 (3H, m), 5.12 (1H, m), 5.23 (2H, br.s), 6.64 (1H, t, J=7.4 Hz), 6.81 (1H, d, J=8.1 Hz), 6.95–7.00 (3H, m), 7.18 (1H, d, J=6.6 Hz), 7.31 (2H, t, J=8.1 Hz), 7.72 (2H, d, J=8.8 Hz), 8.05 (2H, d, J=8.8 Hz), 9.69 (1H, s); IR (KBr)cm$^{-1}$: 3393, 1740, 1610, 1508, 1253.

As described in Example 136, the compounds of Examples 137 to 143 were prepared, each of whose melting point (mp), $^1$H NMR data and/or IR data are shown below.

Example 137

N-(2-Aminophenyl)-4-[5-(4-nitrophenoxy)methyl-1,3-oxazolin-2-on-3-yl-yl]benzamide (Table 2: Compound 2)

mp: 162–164° C.; $^1$H NMR (270 MHz, DMSO-d$_6$) δ ppm: 3.97 (1H, dd, J=6.6, 9.5 Hz), 4.10 (1H, dd, J=5.1, 11.0 Hz), 4.17 (1H, dd, J=3.7, 11.0 Hz), 4.27 (1H, t, J=8.8 Hz), 6.53–6.80 (6H, m), 6.97 (1H, t, J=8.1 Hz), 7.16 (1H, d, J=6.6 Hz), 7.72 (2H, d, J=8.8 Hz), 8.04 (2H, d, J=8.8 Hz), 9.65 (1H, s); IR (KBr)cm$^{-1}$: 3356, 2365, 1741, 1609, 1510, 1247.

Example 138

N-(2-Aminophenyl)-4-(5-benzyloxymethyl-1,3-oxazolin-2-on-3-yl)benzamide Hydrochloride (Table 2: Hydrochloride of Compound 3)

mp: 181–183° C.; $^1$H NMR (270 MHz, DMSO-d$_6$) δ ppm: 3.69 (1H, dd, J=5.2, 11.0 Hz), 3.76 (1H, dd, J=3.7, 11.0 Hz), 3.91 (1H, dd, J=5.9, 8.8 Hz), 4.59 (2H, s), 4.93 (1H, m), 7.26–7.41 (8H, m), 7.51 (1H, m) 7.74 (2H, d, J=8.8 Hz), 8.15 (2H, d, J=8.8 Hz, 10.42 (1H, s).

Example 139

N-(2-Aminophenyl)-4-[5-(pyridin-3-yl)oxymethyl-1,3-oxazolin-2-on-3-yl]benzamide (Table 2: Compound 4)

mp: 199–201° C.; $^1$H NMR (270 MHz, DMSO-d$_6$) δ ppm: 4.01 (1H, dd, J=6.6, 8.8 Hz), 4.28–4.46 (3H, m), 4.96 (2H, br.s), 5.14 (1H, m), 6.61 (1H, t, J=7.4 Hz), 6.79 (1H, d, J=7.4 Hz), 6.98 (1H, t, J=7.4 Hz), 7.16 (1H, d, J=7.4 Hz), 7.36 (1H, dd, J=4.4, 8.1 Hz), 7.44 (1H, dd, J=1.5, 8.1 Hz); IR (KBr) cm$^{-1}$: 2815, 2631, 2365, 1752, 1610, 1520, 1225.

Example 140

N-(2-Aminophenyl)-4-[5-(pyridin-3-yl)methyloxymethyl-1,3-oxazolin-2-on-3-yl]benzamide (Table 2: Compound 5)

mp: 160–164° C. (dec.); $^1$H NMR (270 MHz, DMSO-d$_6$) δ ppm: 3.73 (1H, dd, J=5.2, 11.7 Hz), 3.79 (1H, dd, J=2.9, 11.7 Hz), 3.91 (1H, dd, J=5.9, 8.8 Hz), 4.21 (1H, t, J=8.8 Hz), 4.62 (2H, s), 4.91 (3H, br.s), 6.60 (1H, t, J=7.4 Hz), 6.78 (1H, d, J=7.4 Hz), 6.98 (1H, t, J=7.4 Hz), 7.16 (1H, d, J=7.4 Hz), 7.38 (1H, dd, J=4.4, 7.4 Hz), 7.69 (2H, d, J=8.8 Hz), 7.71 (1H, m), 8.03 (2H, d, J=8.8 Hz), 8.51 (1H, dd, J=1.5, 4.4 Hz), 8.54 (1H, d, J=1.5 Hz), 9.65 (1H, s); IR (KBr)cm$^{-1}$: 3368, 1742, 1648, 1608, 1492, 1226.

Example 141

N-(2-Aminophenyl)-4-[5-(3-nitrophenoxy)methyl-1,3-oxazolin-2-on-3-yl]benzamide (Table 2: Compound 6)

mp: 230° C. (dec.); $^1$H NMR (270 MHz, DMSO-d$_6$) δ ppm: 4.04 (1H, t, J=8.8 Hz), 4.32 (1H, t, J=8.8 Hz), 4.41–4.53 (2H, m), 4.91 (2H, s), 5.15 (1H, m), 6.61 (1H, t, J=7.4 Hz), 6.79 (1H, d, J=7.4 Hz), 6.98 (1H, t, J=7.4 Hz), 7.16 (1H, d, J=7.4 Hz), 7.46 (1H, dd, J=1.5, 8.1 Hz), 7.61 (1H, t, J=8.1 Hz), 7.71–7.79 (3H, m), 7.87 (1H, d, J=8.1 Hz), 8.06 (2H, d, J=8.8 Hz), 9.66 (1H, s); IR (KBr)cm$^{-1}$: 3363, 3095, 2365, 1741, 1608, 1529.

Example 142

N-(2-Aminophenyl)-4-[5-(pyridin-2-yl)methyloxymethyl-1,3-oxazolin-2-on-3-yl]benzamide (Table 2: Compound 7)

mp: 172–174° C.;

$^1$H NMR (270MHz, DMSO-d$_6$) δ ppm: 3.79 (1H, dd, J=5.2, 11.0 Hz), 3.85 (1H, dd, J=2.9, 11.0 Hz), 3.95 (1H, dd, J=6.6, 9.6 Hz), 4.23 (1H, t, J=9.6 Hz), 4.67 (2H, s), 4.90 (2H, s), 4.95 (1H, m), 6.60 (1H, t, J=7.4 Hz), 6.78 (1H, d, J=7.4 Hz), 6.97 (1H, t, J=7.4 Hz), 7.16 (1H, d, J=7.4 Hz), 7.29 (1H, dd, J=5.2, 6.6 Hz), 7.40 (1H, d, J=6.6 Hz), 7.70 (2H, d, J=8.8 Hz), 7.78 (1H, dt, J=2.2, 7.4 Hz), 8.03 (2H, d, J=8.8 Hz), 8.51 (1H, d, J=4.4 Hz), 9.64 (1H, s); IR (KBr)cm$^{-1}$: 3369, 1743, 1651, 1608, 1492, 1283.

Example 143

N-(2-Aminophenyl)-4-[5-(pyridin-2-yl)oxymethyl-1,3-oxazolin-2-on-3-yl]benzamide (Table 2: Compound 8)

mp: (amorphous); $^1$H NMR (270 MHz, DMSO-d$_6$) δ ppm: 3.96 (1H, dd, J=5.9, 9.6 Hz), 4.21–4.40 (3H, m), 4.90

(2H, s), 5.03 (1H, m), 6.28 (1H, t, J=6.6 Hz), 6.43 (1H, d, J=99.6 Hz), 6.60 (1H, t, J=6.6 Hz), 6.78 (1H, d, J=6.6 Hz), 6.97 (1H, t, J=7.4 Hz), 7.15 (1H, d, J=6.6 Hz), 7.46 (1H, dt, J=7.4, 1.5 Hz), 7.67 (2H, d, J=8.8 Hz), 7.69 (1H, m), 8.03 (2H, d, J=8.8 Hz), 9.64 (1H, s).

Example 144

N-(2-Aminophenyl)-4-[N-[3-[(pyridin-3-yl)methylamino]cyclobuten-1,2-dion-4-yl]aminomethyl]benzamide (Table 2: Compound 9)

(144-1) To a solution of 0.073 g of 3,4-di-n-butoxy-3-cyclobuten-1,2-dione (0.323 mmol) in 2 mL of THF was added 0.1 g of the compound from Example 1, the process (1-4) (0.293 mmol), and the solution was stirred for 4 hours. After adding 0.033 mL of 3-aminomethylpyridine (0.327 mmol), the solution was reacted for a day. After completion of the reaction, water was added to the solution, and the mixture was extracted twice with methyl ethyl ketone. The organic layer was dried over anhydrous magnesium sulfate and evaporated. The residue was triturated with methanol to give 0.12 g of N-[2-(N-tert-butoxycarbonylamino)phenyl]-4-[N-[3-[(pyridin-3-yl)methylamino]cyclobuten-1,2-dion-4-yl]aminomethyl]benzamide (Yield: 78%).

$^1$H NMR (270 MHz, DMSO-$d_6$) δ ppm: 1.44 (9H, s), 4.75–4.81 (4H, m), 7.15 (1H, dt, J=2.2, 7.4 Hz), 7.20 (1H, dt, J=2.2, 7.4 Hz), 7.74 (1H, dd, J=2.2, 7.4 Hz), 7.47 (2H, d, J=8.1 Hz), 7.54 (2H, dd, J=2.2, 7.4 Hz), 7.73 (1H, m), 7.94 (2H, d, J=8.1 Hz), 8.50 (1H, m), 8.55 (1H, d, J=1.5 Hz), 8.67 (1H, s), 9.82 (1H, s).

(144-2) To a solution of 0.1 g of the compound from the process (144-1) (0.19 mmol) in 4 mL of dioxane and 1 mL of methanol was added 4 mL of 4N hydrochloric acid-dioxane, and the mixture was reacted for 2 hours. After completion of the reaction, the mixture was concentrated and neutralized with saturated sodium bicarbonate aq. Methyl ethyl ketone was added to the mixture, and the precipitated crystals were collected by filtration to give 0.04 g of N-(2-aminophenyl)-4-[N-[3-[(pyridin-3-yl)methylamino]cyclobuten-1,2-dion-4-yl]aminomethyl]benzamide (Yield: 49%).

mp: 230° C.; $^1$H NMR (270 MHz, DMSO-$d_6$) δ ppm: 4.76 (2H, s), 4.79 (2H, s), 4.90 (2H, s), 6.60 (1H, t, J=7.4 Hz), 6.78 (1H, d, J=7.4 Hz), 6.97 (1H, t, J=7.4 Hz), 7.16 (1H, d, J=7.4 Hz), 7.39 (1H, m), 7.43 (2H, d, J=8.1 Hz), 7.73 (1H, d, J=8.1 Hz), 7.97 (2H, d, J=8.1 Hz), 7.99 (1H, br.s), 8.51 (1H, d, J=8.1 Hz), 8.55 (1H, s), 9.64 (1H, s).

Example 145

N-(2-Aminophenyl)-4-[3-(pyridin-3-yl)methylimidazolin-2-on-1-yl]methylbenzamide (Table 2: Compound 10)

(145-1) Potassium carbonate (7.88 g; 57 mmol) was added to a solution of 4.92 g of ethylene urea (57 mmol), 5.73 g of methyl 4-bromomethylbenzoate (25 mmol) and 1.85 g of tetra-n-butylammonium iodide (5.0 mmol) in 30 mL of DMF, and the mixture was heated with stirring at 80° C. for 5 hours. After cooling, the solid was collected by filtration and washed with ethyl acetate. The filtrate was concentrated. The residue was purified by column chromatography on silica gel (eluent: ethyl acetate:methanol=10:1). To the light yellow oil obtained was added diisopropyl ether, and the precipitated solid was collected by filtration and dried to give 3.36 g of N-(4-methoxycarbonylphenylmethyl)imidazolin-2-one (Yield: 57.4%) as a light brown solid.

$^1$H NMR (270 MHz, CDCl$_3$) δ ppm: 3.28–3.35 (2H, m), 3.41–3.47 (2H, m), 3.92 (3H, s), 4.42 (2H, s), 4.61 (1H, br.s), 7.35 (2H, d, J=8.1 Hz), 8.01 (2H, d, J=8.1 Hz).

(145-2) Saturated sodium bicarbonate aq. was added to 2.05 g of 3-chloromethylpyridine hydrochloride (12.5 mmol), and the mixture was extracted with ethyl acetate. The organic layer was washed with saturated brine, dried and evaporated. The residual solvent was azeotropically removed from the residue with toluene. To the residue was added 5 mL of DMF and then 0.37 g of tetra-n-butylammonium iodide (1.0 mmol) to prepare a solution of a benzyl halide in DMF. To a suspension of 0.30 g of sodium hydride (60% oil dispersion) (7.5 mmol) in 5 mL of DMF was slowly added dropwise a solution of 1.17 g of the compound from the process (145-1) (5.0 mmol) in 10 mL of DMF, and the solution was stirred at room temperature for 30 min. After adding the above solution of the benzyl halide, the resulting solution was heated with stirring at 80° C. for 7 hours, and then left at room temperature overnight. After removing DMF, the residue was partitioned between ethyl acetate and water. The aqueous layer was extracted with ethyl acetate-methyl ethyl ketone (2:1). The combined organic layer was washed with saturated brine, dried and evaporated. The residue was purified by column chromatography on silica gel (eluent: ethyl acetate:methanol=10:1) to give 1.17 g of N-(4-methoxycarbonylphenylmethyl)-N'-(pyridin-3-yl)methylimidazolin-2-one (Yield: 72.3%) as a brown oil.

$^1$H NMR (270MHz, CDCl$_3$) δ ppm: 3.20 (4H, s), 3.92 (3H, s), 4.44 (2H, s), 4.46 (2H, s), 7.27–7.36 (3H, m), 7.64–7.69 (1H, m), 8.01 (2H, d, J=8.1 Hz), 8.53–8.56 (2H, m).

(145-3) To a solution of 0.55 g of the compound from the process (145-2) (1.7 mmol) in 8 mL of methanol and 8 mL of water were added 110 mg of lithium hydroxide monohydrate (1.7 mmol) at room temperature, and the solution was heated with stirring at 50° C. for 1.5 hours. Additional lithium hydroxide monohydrate (0.05 g; 1.2 mmol) was added, and the solution was stirred at –50° C. for additional 1.5 hours. The solution was acidified to pH 3–4) with 10% hydrochloric acid. Saturated brine was added, and the mixture was extracted twice with ethyl acetate and once with ethyl acetate-methyl ethyl ketone (1:1). The organic layer was dried over anhydrous sodium sulfate and evaporated. The residue was dried to give 0.32 g of 4-[3-(pyridin-3-yl)methylimidazolin-2-on-1-yl]methylbenzoic acid (Yield: 61%) as a brown oil.

$^1$H NMR (270 MHz, DMSO-$d_6$) δ ppm: 3.17 (2H, s), 3.20 (2H, s), 4.36 (2H, s), 4.38 (2H, s), 7.35–7.42 (3H, m), 7.68 (1H, dd, J=6.6 Hz), 7.92 (2H, d, J=8.1 Hz), 8.51 (2H, m).

(145-4) To a solution of 0.31 g of the compound from the process (145-3) (1.0 mmol) in 12 mL of dichloromethane was added dropwise 0.3 mL of oxalyl chloride (3.5 mmol) at room temperature, and the solution was stirred at room temperature for 30 min and then at 40° C. for 1.5 hours. After evaporation, the residual solvent was azeotropically removed with toluene, and the residue was suspended in 10 mL of dichloromethane. To the suspension under ice-cooling was added dropwise 0.21 g of the compound from Example 1, the process (1-2) (1.0 mmol) in 2 mL of dichloromethane and 2 mL of pyridine. The mixture was warmed with stirring to room temperature and left at room temperature overnight. After adding saturated sodium bicarbonate aq., the mixture was extracted with chloroform. The organic layer was washed with saturated brine, dried and evaporated. The residue was purified by column chromatography on silica gel (eluent: ethyl acetate:methanol=20:1) to give 0.10 g of N-(2-tert-butoxycarbonylaminophenyl)-4-[3-(pyridin-3-ylmethyl)imidazolin-2-on-1-yl]methylbenzamide (Yield: 20%) as a brown oil.

$^1$H NMR (270 MHz, CDCl$_3$) δ ppm: 1.52 (9H, s), 3.20 (4H, s), 4.45 (2H, s), 4.48 (2H, s), 6.75 (1H, br.s), 7.15–7.40 (5H, m), 7.65–7.70 (2H, m), 7.83 (1H, d, J=7.3 Hz), 7.94 (2H, d, J=8.1 Hz), 8.50–8.60 (3H, br.m).

(145-5) To a solution of 100 mg of the compound from the process (145-4) (0.20 mmol) in 2 mL of dioxane was added 2 mL of 4N hydrochloric acid-dioxane and then 0.5 mL of methanol to make the mixture homogenous. After stirring for 2 hours, the solution was neutralized with saturated sodium bicarbonate and extracted with ethyl acetate. The organic layer was washed with saturated brine, dried and evaporated. The residue was dried under reduced pressure to give 47 mg of N-(2-aminophenyl)-4-[3-(pyridin-3-yl)methylimixazolin-2-on-1-yl]methylbenzamide (Yield: 58%) as a brown oil.

mp: (amorphous); $^1$H NMR (270 MHz, DMSO-d$_6$) δ ppm: 3.20 (4H, s), 4.37 (2H, s), 4.39 (2H, s), 4.87 (2H, br.s), 6.60 (1H, dd, J=7.3, 7.3 Hz), 6.78 (1H, d, J=8.1 Hz), 6.97 (1H, dd, J=6.6, 7.3 Hz), 7.16 (1H, d, J=7.3 Hz), 7.35–7.41 (3H, m), 7.68 (1H, d, J=8.1 Hz), 7.90–8.00 (2H, m), 8.50 (2H, br.s), 9.63 (1H, br.s).

Example 146

Preparation of N-(2-Aminophenyl)-4-[N-(pyridin-3-yl)methoxycarbonylaminomethyl]benzamide 0.5 Fumarate (Table 1: Fumarate of Compound 82)

To 10 mL of methanol were added 310 mg of the compound from Example 48, and the mixture was heated to dissolve the solid. To the solution was added 96 mg of fumaric acid in methanol, and the solution was cooled. The precipitated crystals were collected by filtration and recrystallized from 5 mL of methanol to give 200 mg of the desired product (Yield: 56%).

mp:. 166–167° C.; $^1$H NMR (270 MHz, DMSO-d$_6$) δ ppm: 4.28 (2H, d, J=6.6 Hz), 5.10 (2H, s), 6.60 (1H, t, J=8.0 Hz), 6.63 (1H, s), 6.78 (1H, d, J=8.0 Hz), 6.90–7.50 (5H, m), 7.70–8.00 (4H, m), 8.53 (1H, d, J=3.6 Hz), 8.60 (1H, s), 9.63 (1H, s); IR (KBr)cm$^{-1}$: 3332, 1715, 1665, 1505, 1283, 1136, 1044, 983, 760, 712; Elementary analysis for C$_{21}$H$_{20}$N$_4$O$_3$+1/2C$_4$H$_4$O$_4$.

|  | C | H | N |
|---|---|---|---|
| Calculated: | 63.59 | 5.10 | 12.90 |
| Observed: | 63.56 | 5.22 | 12.97 |

As described in Example 146, the compounds of Examples 147 to 149 are prepared, each of whose melting point (mp), $^1$H NMR data, IR data and/or elementary analysis data are shown below.

Example 147

N-(2-Aminophenyl)-4-[N-(pyridin-3-yl)methoxycarbonylaminomethyl]benzamide Maleate (Table 1: Maleate of Compound 82)

mp: 123–124° C.; $^1$H NMR (270 MHz, DMSO-d$_6$) δ ppm: 4.28 (2H, d, J=6.6 Hz), 5.11 (2H, s), 6.24 (2H, s), 6.66 (1H, t, J=8.0 Hz), 6.83 (1H, d, J=8.0 Hz), 6.90–8.00 (9H, m), 8.56 (1H, d, J=3.6 Hz), 8.62 (1H, s), 9.69 (1H, s); IR (KBr)cm$^{-1}$: 3298, 1719, 1546, 1365, 1313, 1250, 1194, 1149, 1044, 993, 862, 751; Elementary analysis for C$_{21}$H$_{20}$N$_4$O$_3$+C$_4$H$_4$O$_4$+0.3H$_2$O.

|  | C | H | N |
|---|---|---|---|
| Calculated: | 60.31 | 4.98 | 11.25 |
| Observed: | 60.52 | 5.12 | 11.03 |

Example 148

N-(2-Aminophenyl)-4-[N-(pyridin-3-yl)methoxycarbonylaminomethyl]benzamide Hydrochloride (Table 1: Hydrochloride of Compound 82)

mp: 140 (dec.) ° C.; $^1$H NMR (270 MHz, DMSO-d$_6$) δ ppm: 4.31 (2H, d, J=5.8 Hz), 5.24 (2H, s), 7.10–7.60 (6H, m), 7.90–8.50 (5H, m), 8.70–8.90 (2H, m), 10.46 (1H, s); IR (KBr)cm$^{-1}$: 2553, 1715, 1628, 1556, 1486, 1254, 1049, 778, 687.

Example 149

N-(2-Aminophenyl)-4-[N-(pyridin-3-yl)oxyacetylaminomethyl]benzamide 0.7 Fumarate (Table 1: Fumarate of Compound 61)

As described in Example 146, the title compound was prepared from the compound of Example 46.

mp: 154–155° C.; $^1$H NMR (270 MHz, DMSO-d$_6$) δ ppm: 4.42 (2H, d, J=5.9 Hz), 4.69 (2H, s), 6.60 (1H, t, J=8.0 Hz), 6.63 (0.7H, s), 6.78 (1H, d, J=8.0 Hz), 6.90–7.50 (6H, m), 7.93 (2H, d, J=8.0 Hz), 8.20–8.40 (2H, m), 8.82 (1H, br.s), 9.63 (1H, s); IR (KBr)cm$^{-1}$: 3324, 1709, 1631, 1521, 1457 ,1428, 1260, 1064, 806, 698; Elementary analysis for C$_{21}$H$_{20}$N$_4$O$_3$+0.7C$_4$H$_4$O$_4$+0.7H$_2$O.

|  | C | H | N |
|---|---|---|---|
| Calculated: | 60.79 | 5.19 | 11.91 |
| Observed: | 60.95 | 5.20 | 11.75 |

Comparative Example 1

N-(3-Aminophenyl)-4-[N-(pyridin-3-yl)methoxycarbonylaminomethyl]benzamide

As described in Example 48, the title compound was prepared.

mp: 156° C.; $^1$H NMR (270 MHz, DMSO-d$_6$) δ ppm: 4.27 (2H, d, J=6.6 Hz), 5.06 (2H, s), 5.10 (2H, s), 6.20–6.40 (1H, m), 6.80–7.10 (3H, m), 7.30–7.50 (3H, m), 7.70–8.00 (4H, m), 8.53 (1H, d, J=3.6 Hz), 8.59 (1H, s), 9.88 (1H, s); IR (KBr)cm$^{-1}$: 3327, 3218, 1708, 1639, 1536, 1279, 1147, 1050, 859, 788.

Comparative Example 2

N-(4-aminophenyl)-4-[N-(pyridin-3-yl)methoxycarbonylaminomethyl]benzamide

As described in Example 48, the title compound was prepared.

mp: 204–205° C.; $^1$H NMR (270 MHz, DMSO-d$_6$) δ ppm: 4.27 (2H, d, J=6.6 Hz), 4.91 (2H, s), 5.10 (2H, s), 6.52 (2H, d, J=8.8 Hz), 7.30–7.50 (5H, m), 7.70–8.00 (4H, m), 8.50–8.60 (2H, m), 9.80 (1H, s); IR (KBr)cm$^{-1}$: 3336, 3224, 1706, 1638, 1530, 1279, 1145, 1050, 1005, 827.

Pharmacological Test Example 1
Test for Induction of Differentiation in A2780 Cells Increase of alkaline phosphatase (ALP) activity is known as an indicator for differentiation of human colon cancer cells. For example, it is known that sodium butylate may increase ALP activity (Young et al., Cancer Res., 45, 2976 (1985); Morita et al., Cancer Res., 42, 4540 (1982)). Thus, differentiation inducing action was evaluated using ALP activity as an indicator.

Experimental Procedure

To each well of a 96-well plate was placed 0.1 mL of A2780 cells (15,000 cells/well) and the next day was added 0.1 mL of a sequential dilute of test solution with the medium. After incubation for 3 days, the cells on the plate were washed twice with a TBS buffer (20 mM Tris, 137 mM NaCl, pH 7.6). Then, to each well was added 0.05 mL of 0.6 mg/mL p-nitrophenylphosphate (9.6% diethanolamine, 0.5 mM $MgCl_2$ (pH 9.6)) solution; and the plate was incubated at room temperature for 30 min. The reaction was quenched with 0.05 mL/well of 3N sodium hydroxide aq. For each well, an absorbance at 405 nm was measured to determine the minimum concentration of the drug inducing increase of ALP activity (ALPmin).

Results

The results are shown in Table 5.

TABLE 5

| Differentiation-inducing action to A2780 cells | |
| --- | --- |
| Test Compound | ALPmin ($\mu$M) |
| Example 1 | 1 |
| Example 2 | 3 |
| Example 3 | 3 |
| Example 4 | 1 |
| Example 5 | 1 |
| Example 6 | 1 |
| Example 7 | 1 |
| Example 8 | 1 |
| Example 9 | 1 |
| Example 10 | 3 |
| Example 11 | 1 |
| Example 13 | 1 |
| Example 15 | 3 |
| Example 16 | 3 |
| Example 17 | 3 |
| Example 18 | 3 |
| Example 23 | 1 |
| Example 24 | 1 |
| Example 25 | 3 |
| Example 26 | 1 |
| Example 27 | 10 |
| Example 28 | 10 |
| Example 29 | 10 |
| Example 30 | 0.1 |
| Example 31 | 10 |
| Example 32 | 3 |
| Example 33 | 0.3 |
| Example 34 | 0.1 |
| Example 35 | 0.3 |
| Example 36 | 10 |
| Example 37 | 1 |
| Example 38 | 3 |
| Example 39 | 0.1 |
| Example 40 | 10 |
| Example 41 | 0.3 |
| Example 42 | 10 |
| Example 43 | 3 |
| Example 44 | 0.01 |
| Example 45 | 0.003 |
| Example 46 | 0.1 |
| Example 48 | 0.1 |
| Example 49 | 1 |

TABLE 5-continued

| Differentiation-inducing action to A2780 cells | |
| --- | --- |
| Test Compound | ALPmin ($\mu$M) |
| Example 50 | 1 |
| Example 51 | 1 |
| Example 52 | 1 |
| Example 53 | 3 |
| Example 54 | 1 |
| Example 55 | 1 |
| Example 56 | 3 |
| Example 57 | 3 |
| Example 58 | 3 |
| Example 59 | 3 |
| Example 60 | 3 |
| Example 63 | 3 |
| Example 64 | 3 |
| Example 65 | 3 |
| Example 66 | 3 |
| Example 67 | 3 |
| Example 68 | 3 |
| Example 70 | 0.1 |
| Example 71 | 10 |
| Example 72 | 10 |
| Example 73 | 3 |
| Example 74 | 10 |
| Example 76 | 1 |
| Example 77 | 3 |
| Example 79 | 0.1 |
| Example 80 | 0.1 |
| Example 81 | 10 |
| Example 82 | 1 |
| Example 85 | 3 |
| Example 86 | 0.3 |
| Example 87 | 0.1 |
| Example 88 | 0.1 |
| Example 89 | 0.3 |
| Example 90 | 3 |
| Example 91 | 0.1 |
| Example 92 | 3 |
| Example 93 | 3 |
| Example 94 | 3 |
| Example 95 | 3 |
| Example 96 | 10 |
| Example 97 | 0.1 |
| Example 98 | 0.1 |
| Example 99 | 3 |
| Example 100 | 1 |
| Example 101 | 3 |
| Example 102 | 3 |
| Example 103 | 1 |
| Example 104 | 1 |
| Example 105 | 1 |
| Example 106 | 1 |
| Example 107 | 1 |
| Example 108 | 3 |
| Example 109 | 1 |
| Example 110 | 3 |
| Example 111 | 3 |
| Example 112 | 0.1 |
| Example 113 | 0.3 |
| Example 114 | 3 |
| Example 115 | 0.01 |

TABLE 5-continued

Differentiation-inducing action to A2780 cells

| Test Compound | ALPmin ($\mu$M) |
|---|---|
| Example 116 | 0.01 |
| Example 119 | 3 |
| Example 120 | 0.3 |
| Example 121 | 3 |
| Example 122 | 0.03 |
| Example 123 | 3 |
| Example 124 | 3 |
| Example 125 | 0.1 |
| Example 126 | 3 |
| Example 127 | 0.3 |
| Example 128 | 0.1 |
| Example 129 | 1 |
| Example 130 | 0.03 |
| Example 131 | 0.3 |
| Example 132 | 10 |
| Example 133 | 3 |
| Example 134 | 3 |
| Example 135 | 3 |
| Example 136 | 1 |
| Example 137 | 1 |
| Example 138 | 1 |
| Example 139 | 0.3 |
| Example 140 | 0.3 |
| Example 141 | 1 |
| Example 142 | 0.1 |
| Example 143 | 3 |
| Example 145 | 3 |
| Comp. Ex. 1 | >100 |
| Comp. Ex. 2 | >100 |

Pharmacological Test Example 2

Antitumor Test Procedure

Murine myeloid leukemia cells WEHI-3 (1 to 3×10⁶ cells) were intraperitoneally inoculated to a Balb/C mouse, and administration of a test compound was initiated on the next day. The day was Day 1 and subsequently the drug was orally administered once a day in Day 1 to 4 and in Day 7 to 11. Survival days after inoculation were observed, which were used to calculate the ratio of the survival days for the test compound group to those for the control group (T/C, %). The ratio was used to evaluate a life prolongation effect.

Results

The results are shown in Table 6.

TABLE 6

Antitumor action to WEHI-3 cells

| Test compound | Dose ($\mu$mol/kg) | T/C (%) |
|---|---|---|
| Example 45 | 16 | 138 |
| Example 46 | 32 | 141 |
| Example 48 | 130 | 190 |
| Example 130 | 130 | 189 |

Pharmacological Test Example 3

Antitumor Action Test

Experimental Procedure

To a nude mouse was inoculated tumor cells subcutaneously subcultured in a nude mouse (HT-29, KB-3-1). When the volume became about 20 to 100 mm³ and take was confirmed, administration of a drug was initiated. This day was Day 1, and subsequently the drug was orally administered in Day 1 to 5, in Day 8 to 12, Day 15 to 19 and in Day 22 to 26.

The volume of the tumor was determined from the following equation:

(Volume of a tumor)=½×(major axis)×(minor axis)²

Results

The results for the compound of Example 48 (dose: 66 $\mu$mol/kg) against HT-29 are shown in FIG. 1.

The results for the compound of Example 48 (dose: 66 $\mu$mol/kg) against KB-3-1 are shown in FIG. 2.

Calculation Example

Model Construction of Superposition Using High Activity Compounds

Three dimensional structure was superimposed using the compounds of Examples 45, 46 and 48 which exhibit a high differentiation-inducing activity, to extract information on spatial configurations of atomic groups necessary for expression of their activity.

For this purpose, any of commercially available program packages, e.g., CATALYST(MSI), Cerius2/QSAR+(MSI) and SYBYL/DISCO(Tripos), may be used to perform a similar level of analysis. Here, SYBYL/DISCO(Tripos) was used for construction of a superimposed structure and analyses.

For the compound of Example 48, a three-dimensional structure was generated using the sketch function of SYBYL, a point charge was allocated on each atom by Gasteiger-Huckel method, and the structure was optimized using Tripos force field. A dummy atom was placed at sites possibly interacting with a biomolecule in order to determine the sites where such an interaction may occur and which may be important for an interaction between a drug and a biomolecule, e.g., a hydrophobic-interaction site (e.g., an aromatic ring and an aliphatic side chain) and a hydrogen-bonding site (e.g., a carbonyl oxygen, hydroxyl and amino). The interactions were categorized in order to identify the types of interaction, e.g., hydrophobic interaction, hydrogen bond and electrostatic interaction, and a different type of dummy atom was allocated to each of the interactions. Furthermore, conformers were generated by rotating the molecule at a rotatable bond to retain a conformation in which there was a change of the distance between dummy atoms allocated at the possible interaction sites, in a conformation file as a candidate conformation. For the compounds of Examples 45 and 46, three dimensional structures were constructed and conformations were generated as described for the compound of Example 48.

Using the compound of Example 48 as a template, for each of its conformations a superimposed structure was constructed so that the dummy atoms showing the same type of interaction were superimposed for both conformations of Examples 45 and 46.

For the superimposed structures, the optimal superimposed structure was selected according to the analysis results of the three dimensional QSAR using the number of the dummy atoms used in the superimposition (the number of common interactions), the degree of steric superimposition (volume of superimposition) and the activity values.

It was found that in the superimposed structure obtained, the centroid of ring B (W1), the centroid of ring A (W2) and hydrogen bond acceptor (e.g., carbonyl oxygen)(W3) in formula (13) are positioned in a manner that there are the following relationships between them; W1–W2=8.34 Å, W1–W3=3.80 Å and W2–W3=5.55 Å.

Calculation Example 1: the Compound of Example 130

Appropriate 7 atoms were selected from the possible interaction sites and the constituent atoms of the benzamide structure of the compound of Example 130, and optimization was performed by applying restrained potential to the compound of Example 130, using the compounds of Examples 45, 46 and 48 used in the above superimposition as target structures. Then, optimization was performed without restrained potential to obtain an active conformation of the compound of Example 130. For this active conformation, the centroid of the benzene ring in the benzamide (W1), the centroid of the pyridine ring (W2) and the carbonyl carbon (W3) were determined to extract the parameters on its spatial configuration.

All conformations were generated for the rotatable bonds, and for each of the conformations, an energy level was calculated to determine the most stable structure. The energy level of the most stable structure was calculated to determine the difference from the active conformation. As a result, it was found that the structure obtained may have a configuration in which W1–W2=8.43 Å, W1–W3=3.82 Å and W2–W3=5.88 Å (energy difference from the most stable structure=2.86 kcal/mol).

With analysis using the dummy atoms obtained in the construction of the above superimposed structure model, the same results were obtained.

Results

The results of the calculation are shown in Table 7.

TABLE 7

| Calculation results of the parameters on the spatial configurations | | | |
|---|---|---|---|
| Compound | W1-W2 (Å) | W1-W3 (Å) | W2-W3 (Å) |
| Example 39 | 8.20 | 3.95 | 5.49 |
| Example 45 | 8.54 | 3.85 | 5.55 |
| Example 46 | 7.42 | 3.97 | 5.93 |
| Example 47 | 8.52 | 3.88 | 5.96 |
| Example 48 | 8.43 | 3.94 | 5.51 |
| Example 79 | 7.09 | 5.20 | 5.48 |
| Example 80 | 8.59 | 4.37 | 5.51 |

TABLE 7-continued

| Calculation results of the parameters on the spatial configurations | | | |
|---|---|---|---|
| Compound | W1-W2 (Å) | W1-W3 (Å) | W2-W3 (Å) |
| Example 87 | 6.80 | 3.80 | 3.63 |
| Example 88 | 8.67 | 3.50 | 6.22 |
| Example 124 | 8.29 | 3.75 | 6.42 |
| Example 128 | 8.64 | 3.76 | 5.90 |
| Example 130 | 8.43 | 3.82 | 5.88 |
| Example 131 | 8.59 | 4.88 | 5.47 |
| Example 136 | 7.59 | 3.94 | 7.27 |
| Example 137 | 7.58 | 3.94 | 7.27 |
| Example 138 | 9.07 | 3.94 | 7.47 |
| Example 139 | 7.64 | 3.94 | 7.29 |
| Example 140 | 9.11 | 3.94 | 7.50 |
| Example 141 | 7.60 | 3.94 | 7.28 |
| Example 142 | 9.02 | 3.94 | 7.44 |
| Example 143 | 7.62 | 3.94 | 7.29 |
| Example 145 | 8.48 | 4.40 | 5.69 |

What is claimed is:

1. An anilide compound having the structure represented by formula (13):

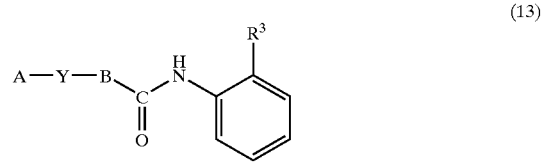

(13)

wherein A is an optionally substituted phenyl group or an optionally substituted heterocyclic group selected from the group consisting of pyridine, pyrazine, pyrimidine, pyridazine, thiophene, furan, pyrrole, isoxazole, isothiazole, imidazole, thiazole, oxazole, tetrahydrofuran, piperidine, piperazine, quinuclidine, quinoline, benzofuran, benzothiophene, indole, furopyridine, thienopyridine and pyrrolopyridine, wherein the substituent(s) for the phenyl group or the heterocyclic group is (are) 1 to 3 substituents selected from a nitro group or a cyano group or 1 to 4 substituents selected from the group consisting of a halogen atom, a hydroxyl group, an amino group, an alkyl group having 1 to 4 carbons, an alkoxy group having 1 to 4 carbons, an aminoalkyl group having 1 to 4 carbons, an alkylamino group having 1 to 4 carbons, an acyl group having 1 to 4 carbons, an acylamino group having 1 to 4 carbons, an alkylthio group having 1 to 4 carbons, a perfluoroalkyl group having 1 to 4 carbons, a perfluoroalkyloxy group having 1 to 4 carbons, a carboxyl group, an alkoxycarbonyl group having 1 to 4 carbons, a phenyl group and a heterocyclic group;

B is an optionally substituted phenyl group or an optionally substituted heterocyclic group selected from the group consisting of thiophene, benzofuran and benzothiophene, wherein the substituent(s) for the phenyl group or the heterocyclic group is (are) 1 to 3 substituents selected from a nitro group or a cyano group or 1 to 4 substituents selected from the group consisting of a halogen atom, a hydroxyl group, an amino group, an alkyl group having 1 to 4 carbons, an alkoxy group having 1 to 4 carbons, an aminoalkyl group having 1 to 4 carbons, an alkylamino group having 1 to 4 carbons, an acyl group having 1 to 4 carbons, an acylamino group having 1 to 4 carbons, an alkylthio group having 1 to 4 carbons, a perfluoroalkyl group having 1 to 4 carbons, a perfluoroalkyloxy group having 1 to 4 carbons, a carboxyl group, an alkoxycarbonyl group having 1 to 4 carbons, a phenyl group and a heterocyclic group;

Y, which links A and B is represented by formula (27):

-T1-T2-T3- (27)

wherein
T1 is —O—CH$_2$—, —CH$_2$—O—CH$_2$—, —CH$_2$—NH—, —CH$_2$—or —O—;
T3 is —NH—CH$_2$—, —CH$_2$—, —CO—NH—, —CO— or a direct bond;
when T3 is —NH—CH$_2$—, —CH$_2$—, or a direct bond, T2 is a cyclic moiety having —CO— or —CS—, said cyclic moiety consisting of one selected from the group consisting of an oxazolidine ring, an imidazolidine ring, a piperazine ring, a pyrrolidine ring or a cyclobutene ring, wherein one or two of said —CO— or —CS— is formulated by combining O or S with one or two carbon atoms of the cyclic moiety; or
when T3 is —CO—NH— or —CO—, T2 is a cyclic moiety consisting of a pyrrolidine ring;

$R^3$ is a hydroxy or amino group;

or a pharmaceutically acceptable salt thereof.

2. An anilide compound or a pharmaceutically acceptable salt thereof as claimed in claim 1, wherein A is an optionally substituted heterocycle; $R^3$ is an amino group; and Y is a moiety having —CO— which is cyclic and links A and B.

3. An anilide compound or a pharmaceutically acceptable salt thereof as claimed in claim 1, wherein B is an optionally substituted phenyl.

4. The anilide compound or a pharmaceutically acceptable salt thereof as claimed in claim 1, wherein T2 as the cyclic moiety having —CO— or —CS— is one of the groups illustrated in formula (5)

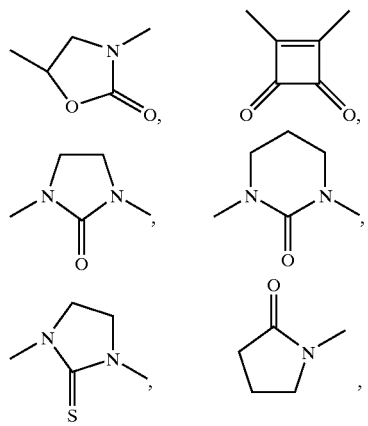

and T2 as the pyrrolidine ring is:

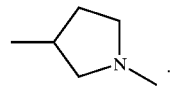

5. The anilide compound or a pharmaceutically acceptable salt thereof as claimed in claim 1, wherein Y is one of the groups illustrated in formula (6):

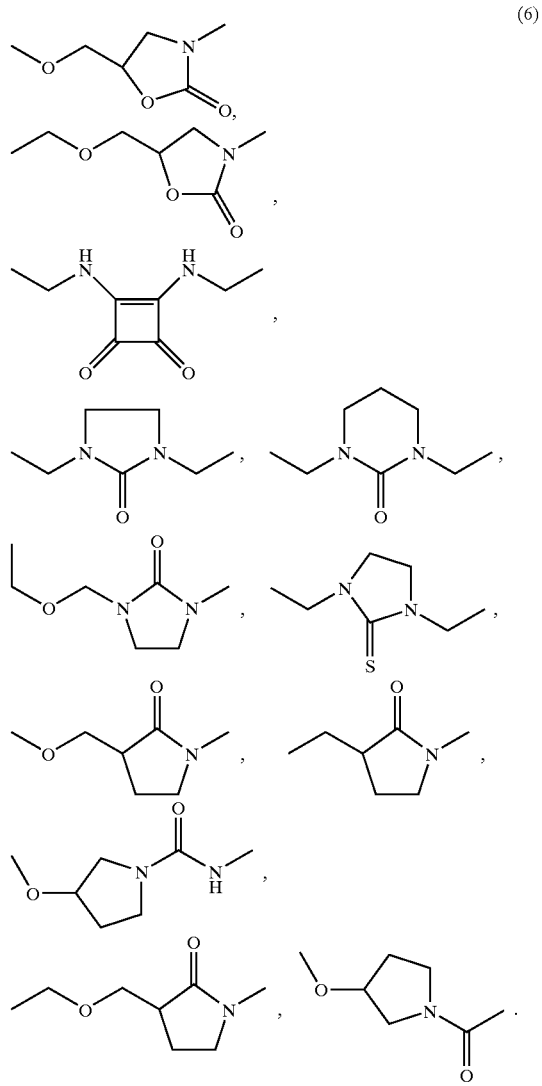

6. An anilide compound having the structure represented by formula (13):

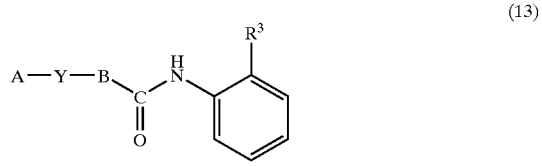

wherein A is an optionally substituted phenyl group or an optionally substituted heterocyclic group selected from the group consisting of pyridine, pyrazine, pyrimidine, pyridazine, thiophene, furan, pyrrole, isoxazole, isothiazole, imidazole, thiazole, oxazole, tetrahydrofuran, piperidine, piperazine, quinuclidine, quinoline, benzofuran, benzothiophene, indole, furopyridine, thienopyridine and pyrrolopyridine, wherein the substituent(s) for the phenyl group or the heterocyclic group is (are) 1 to 3 substituents selected from a nitro group or a cyano group or 1 to 4 substituents selected from the group consisting of a halogen atom, a hydroxyl group, an amino group, an alkyl group having 1 to 4 carbons, an alkoxy group having 1 to 4 carbons, an aminoalkyl group having 1 to 4 carbons, an alkylamino group having 1 to 4 carbons, an acyl group having 1 to 4 carbons, an acylamino group having 1 to 4 carbons, an alkylthio group having 1 to 4 carbons, a perfluoroalkyl group having 1 to 4 carbons, a perfluoroalkyloxy group having 1 to 4 carbons, a carboxyl group, an alkoxycarbonyl group having 1 to 4 carbons, a phenyl group and a heterocyclic group:

B is an optionally substituted heterocyclic group selected from the group consisting of thiophene, benzofuran and benzothiophene, wherein the substituent(s) for the heterocyclic group is (are)1 to 3 substituents selected from a nitro group or a cyano group or 1 to 4 substituents selected from the group consisting of a halogen atom, a hydroxyl group, an amino group, an alkyl group having 1 to 4 carbons, an alkoxy group having 1 to 4 carbons, an aminoalkyl group having 1 to 4 carbons, an alkylamino group having 1 to 4 carbons, an acyl group having 1 to 4 carbons, an acylamino group having 1 to 4 carbons, an alkylthio group having 1 to 4 carbons, a perfluoroalkyl group having 1 to 4 carbons, a perfluoroalkyloxy group having 1 to 4 carbons, a carboxyl group, an alkoxycarbonyl group having 1 to 4 carbons, a phenyl group and a heterocyclic group;

Y, which links A and B, is —X—Q—(CH$_2$)$_n$— wherein X is a direct bond or a moiety having a structure selected from those in formula (2):

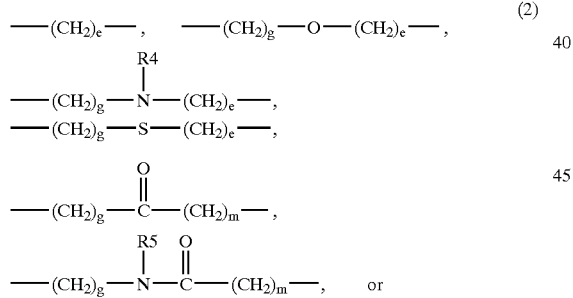

(2)

-continued

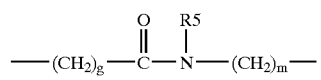

wherein e is an integer of 1 to 4; g and m are independently an integer of 0 to 4; R4 is a hydrogen atom or an optionally substituted alkyl group having 1 to 4 carbons, or the acyl group represented by formula (3)

(3)

wherein R6 is an optionally substituted alkyl group having 1 to 4 carbons, a perfluoroalkyl group having 1 to 4 carbons, a phenyl group or a heterocyclic group; R5 is a hydrogen atom or an optionally substituted alkyl group having 1 to 4 carbons;

n is an integer of 0 to 4, provided that when X is a direct bond, n is not zero;

Q is a moiety having a structure selected from those in formula (4):

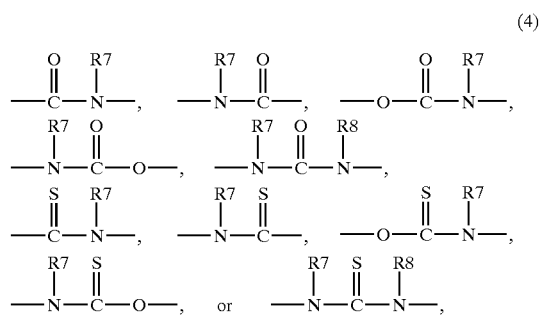

(4)

wherein R7 and R8 are independently a hydrogen atom or an optionally substituted alkyl group having 1 to 4 carbons;

R3 is a hydroxy or amino group.

* * * * *